US010809180B2

(12) United States Patent
Kelley et al.

(10) Patent No.: US 10,809,180 B2
(45) Date of Patent: Oct. 20, 2020

(54) DEVICE FOR MAGNETIC PROFILING OF PARTICLES IN A FLOW

(71) Applicant: THE GOVERNING COUNCIL OF THE UNIVERSITY OF TORONTO, Toronto (CA)

(72) Inventors: Shana Kelley, Toronto (CA); Edward Sargent, Toronto (CA); Mahla Poudineh, Toronto (CA); Reza Mohamadi, Toronto (CA); Peter Aldridge, Toronto (CA)

(*) Notice: Subject to any disclaimer, the term of this patent is extended or adjusted under 35 U.S.C. 154(b) by 55 days.

(21) Appl. No.: 15/764,030

(22) PCT Filed: Sep. 27, 2016

(86) PCT No.: PCT/CA2016/051128
§ 371 (c)(1),
(2) Date: Mar. 28, 2018

(87) PCT Pub. No.: WO2017/054075
PCT Pub. Date: Apr. 6, 2017

(65) Prior Publication Data
US 2018/0292305 A1    Oct. 11, 2018

Related U.S. Application Data

(60) Provisional application No. 62/233,648, filed on Sep. 28, 2015.

(51) Int. Cl.
*G01N 15/14* (2006.01)
*B01L 3/00* (2006.01)
(Continued)

(52) U.S. Cl.
CPC .... *G01N 15/1484* (2013.01); *B01L 3/502746* (2013.01); *B01L 3/502761* (2013.01);
(Continued)

(58) Field of Classification Search
CPC ............ G01N 15/1484; G01N 33/491; G01N 33/57492; G01N 15/1475;
(Continued)

(56) References Cited

U.S. PATENT DOCUMENTS

2006/0252054 A1    11/2006 Lin et al.
2008/0302732 A1    12/2008 Sph et al.
(Continued)

FOREIGN PATENT DOCUMENTS

WO    2010138391 A2    12/2010
WO    2014150928 A1     9/2014
WO    2014166000 A1    10/2014

OTHER PUBLICATIONS

Kang et al., A combined micromagnetic-microfluidic device for rapid capture and culture of rare circulating tumor cells, Lab on a Chip, vol. 12, pp. 2175-2181. (Year: 2012).*
(Continued)

*Primary Examiner* — Melanie Brown
(74) *Attorney, Agent, or Firm* — Ridout & Maybee LLP

(57) ABSTRACT

Methods and devices for magnetic profiling of target particles in a flow. There are a plurality of flow rate-reducing structures in a flow chamber. Each flow rate-reducing structure is provided with a localized magnetic attractive force, the magnetic attractive force defining a capture zone in the vicinity of the flow rate-reducing structure. The size of capture zones may be variable for different locations within the device. The magnetic attractive force, in the capture zone, is sufficiently high to overcome the drag force on a given subset of the target particles to promote capture of any particles belonging to the subset of the target particles in the capture zone. Different target particles having different magnetic susceptibility are captured in different capture zones.

15 Claims, 55 Drawing Sheets

(51) Int. Cl.
| | |
|---|---|
| B03C 1/033 | (2006.01) |
| B03C 1/28 | (2006.01) |
| B03C 1/30 | (2006.01) |
| G01N 33/49 | (2006.01) |
| G01N 33/574 | (2006.01) |
| G01N 15/10 | (2006.01) |

(52) U.S. Cl.
CPC ............ *B03C 1/0332* (2013.01); *B03C 1/288* (2013.01); *B03C 1/30* (2013.01); *G01N 15/1475* (2013.01); *G01N 33/491* (2013.01); *G01N 33/57492* (2013.01); *B01L 2200/0668* (2013.01); *B01L 2300/0816* (2013.01); *B01L 2400/043* (2013.01); *B01L 2400/0487* (2013.01); *B01L 2400/086* (2013.01); *B03C 2201/18* (2013.01); *B03C 2201/26* (2013.01); *G01N 2015/1006* (2013.01); *G01N 2015/149* (2013.01)

(58) Field of Classification Search
CPC ......... B01L 3/502746; B01L 3/502761; B03C 1/0332; B03C 1/288; B03C 1/30
See application file for complete search history.

(56) References Cited

U.S. PATENT DOCUMENTS

| | | | |
|---|---|---|---|
| 2009/0053799 | A1 | 2/2009 | Chang-Yen et al. |
| 2011/0003303 | A1* | 1/2011 | Pagano ............. B01L 3/502776 435/6.19 |
| 2011/0059468 | A1* | 3/2011 | Earhart .................. C12N 13/00 435/7.21 |
| 2011/0212440 | A1 | 9/2011 | Viovy et al. |
| 2013/0017538 | A1* | 1/2013 | Ionescu-Zanetti ...... B03C 1/288 435/6.11 |
| 2014/0154703 | A1* | 6/2014 | Skelley ............. B01L 3/502761 435/7.23 |
| 2014/0295426 | A1 | 10/2014 | Albelda et al. |
| 2015/0336096 | A1* | 11/2015 | Smith ..................... B03C 1/288 435/309.1 |

OTHER PUBLICATIONS

Chen et al., On-chip magnetic field modulation for distributed immunomagnetic detection of circulating tumor cells, Transducers, Barcelona, Spain, 16-20, pp. 1202-1205. (Year: 2013).*

Chen et al., Immunomagnetic CTCs detection at small scale: multiphysical modeling, thin-film magnets and cancer screening, Dissertation, pp. 1-145. (Year: 2014).*

B.P. Casavant et al., A negative selection methodology using a microfluidic platform for the isolation and enumeration of circulating tumor cells. methods 64, 137-143(2013).

C.L. Chaffer, R.A. Weinberg, A perspective on cancer cell metastasis. Science 331, 1559-1564(2011).

W. Zhao et al., Bioinspired multivalent DNA network for capture and release of cells. proc. natl. Acad. Sci., U.S.A, 109, 19626-19631 (2012).

C. Alix-Panabieres, K. Pantel, Challenges in circulating tumor cell research. Nat. Rev. Cancer 14, 623-631 (2014).

M. Yu et al. Circulating breast tumor cells exhibit dynamic changes in epithelial and mesenchymal composition. Science 339, 580-584 (2013).

V. Plaks, C.D. Koopman, Z. Werb, Cancer. Circulating tumor cells. Science 341, 1186-1188 (2013).

J.M. Lang, B. P. Casavant, D.J. Beebe, Circulating tumor cells: getting more from less. Sci. Transl. Med. 4, 141ps113 (2012).

I.Y. Wong et al., Collective and individual migration following the epithelial-mesenchymal transition. Nat. Mater. 13, 1063-1071(2014).

Hoshino et al. 'Microchip-based Immunomagnetic Detection of Circulating Tumor Cell'. Lab Chip. Oct. 21, 2011; 11(20):3449-3457.

E. Ozkumur et al., Inertial focusing for tumor antigen-dependent and -independent sorting or rare circulating tumor cells. Sci. Transl. Med. 5, 179ra147(2013).

A.H. Talasaz et al., isolating highly enriched populations of circulating epithelial cells and other rare cells from blood using a magnetic sweeper device. Proc. Natl. acad. sci., USA, 106, 3970-3975(2009).

S.L. Stott et al., Isolation of circulating tumor cells using a microvortex-generating herringbone-chip. Proc. Natl. Acad. Sci., U.S.A. 107, 18392-18397(2010).

S. Nagrath et. al., Isolation of rare circulating tumor cells in cancer patients by microchip technology. Nature 450, 1235-1239 (2007).

X.Hu et al., Marker-specific sorting of rare cells using dielectrophoresis. Proc. Natl. Acad.Sci., USA. 102, 15757-15761 (2005).

P. Chen et al., Microscale Magnetic Field Modulation for Enhanced Capture and Distribution of Rare Circulating Tumor Cells. Sci. Rep. 5, 8745-8753(2015).

R.M. Mohamadi et al., Nanoparticle-mediated binning and profiling of heterogeneous circulating tumor cell subpopulations. Angew. Chem. Intl. Ed. Engl. 54, 139-143 (2015).

T.L. Halo et al., Nanoflares for the detection, isolation, and culture of live tumor cells from human blood. Proc. Natl., Acad. Sci., U.S.A. 111, 17104-17109 (2014).

A. A. Adams et al., Highly efficient circulating tumor cell isolation from whole blood and label free enumeration using polymer-based microfluids with an integrated conductivity sensor. J.Am. Chem. Soc. 130, 8633-8641(2008).

Y.B. Zhang et al., The effects of $CoCl_2$ on HIF-1a protein under experimental conditions of autoprogressive hypoxia using mouse models. Int. J. Mol. Sci. 15, 10910-1012(2014).

E. Reategui et al., Tunable nanostructured coating for the capture and selective release of viable circulating tumor cells. Adv. Mater. 27, 1593-1599(2015).

P.G. Shiro et al. Sensitive and high-thoroughput isolation of rare cells from peripheral blood with ensemble-decision aliquot ranking. Angew. chem. Intl. Ed. 51, 4618-4622 (2012).

H.J. Yoon et al., Sensitive capture of circulating tumor cells by functionalized graphene oxide nanosheets. Nat. Nanotechnol. 8, 734-741 (2013).

S.C. Bendall et al., Single-cell mass cytometry of differential immune and drug responses across a human hematopoietic continuum. science 332, 687-696 (2011).

E. Sollier et al., size-selective collection of circulating tumor cells using vortex technology. Lab chip 14, 63-77 (2014).

D.L. Jaye et al. , Translational applications of flow cytometry in clinical practice. J. Immunol. 188, 4715-4719(2012).

Wei et al. "Trapping and Dynamic Manipulation of Magnetic Contrast Agent Targeted Cancer Cells in Photoacoustic Imaging:Phantom Study". Ultrasonics Symposium (IUS), 2011 IEEE International, Date of Conference: Oct. 18-21, 2011. Whole Document.

D. Issadore et al., Ultrasensitive clinical enumeration of rare cells ex vivo using a micro-hall detector. Sci. Transl. Med. 4, 141ra192 (2012).

J.D. Besant et al., Velocity valleys enable efficient capture and spatial sorting of nanoparticle-bound cancer cells. nanoscale 7, 6278-6285(2015).

Z. Wang, J.M. Belovich, A simple apparatus for measuring cell settling velocity. Biotechnol. Prog. 26, 1361-1366 (2010).

S. Wang et al., Highly efficient capture of circulating tumor cells by using nanostructured silicon substrates with integrated chaotic micromixers. Angew. Chem. Intl. Ed. 50, 3084-3088(2011).

Wei et al. "Magnetic trapping and photoacoustic detection of rare circulating tumor cells". Ultrasonics symposium (IUS), 2012 IEEE International, Issue Date:Oct. 7-10, 2012. Whole Document.

* cited by examiner

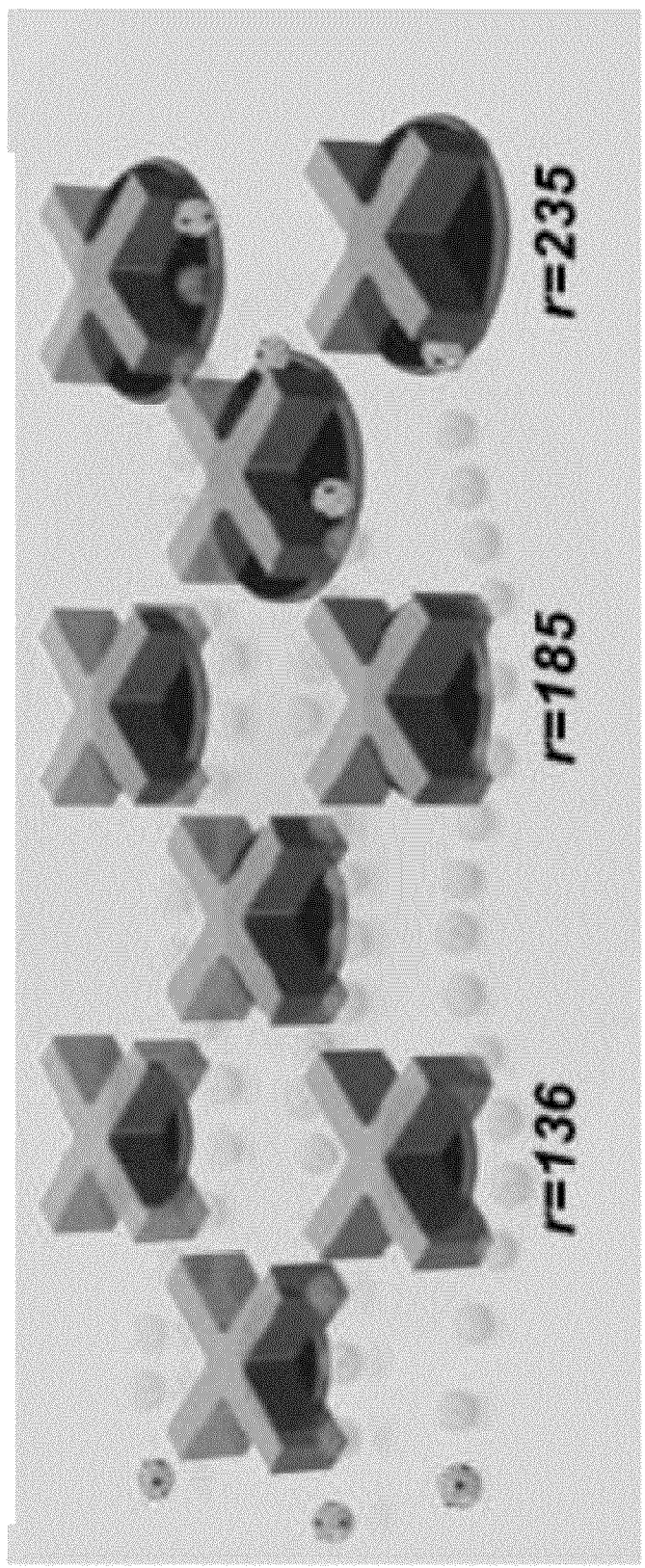
FIG. 1Dii

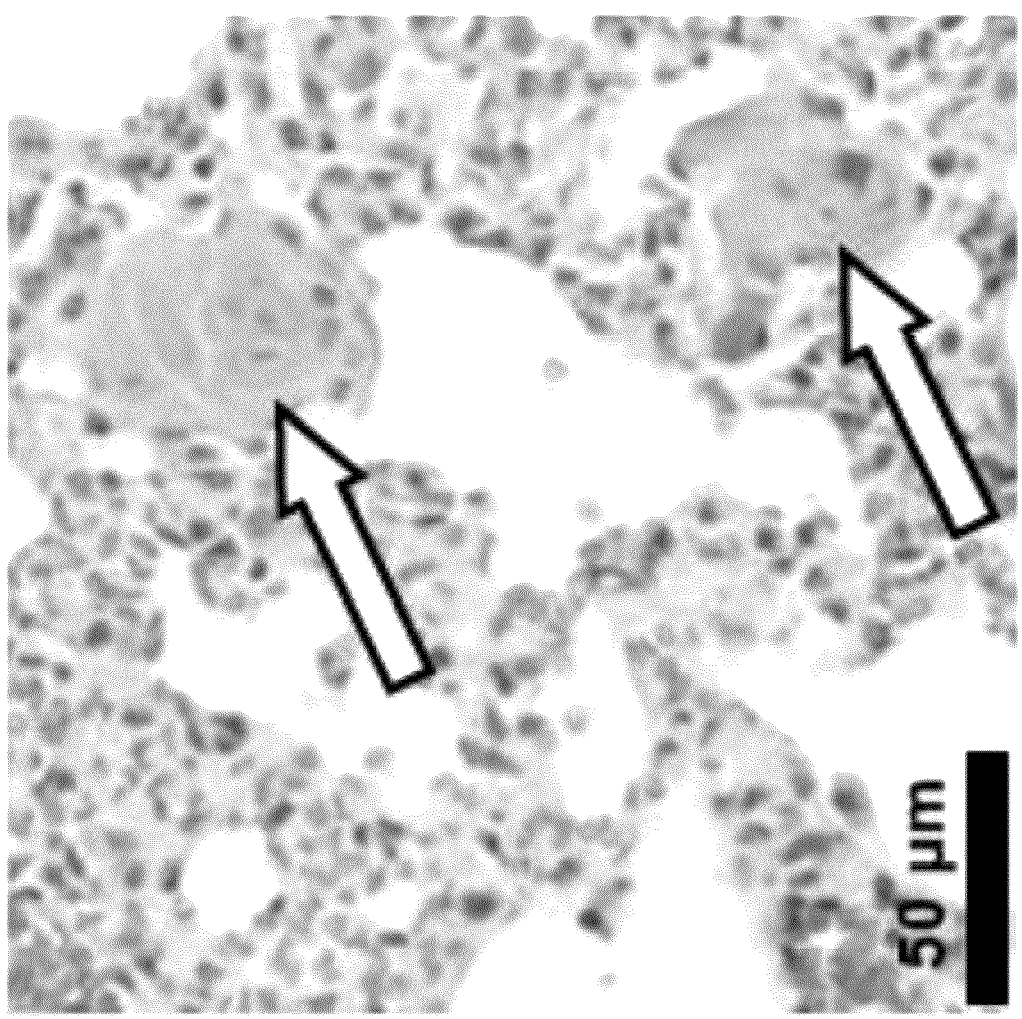

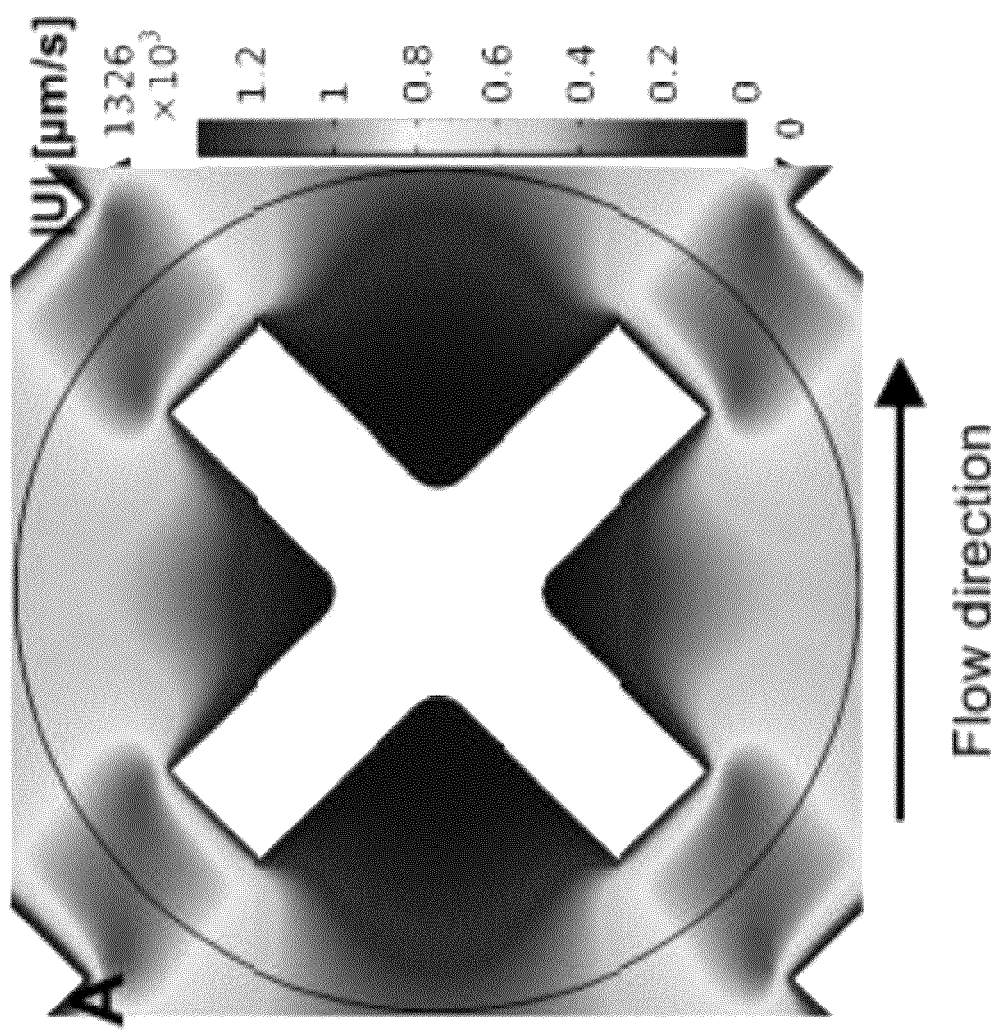

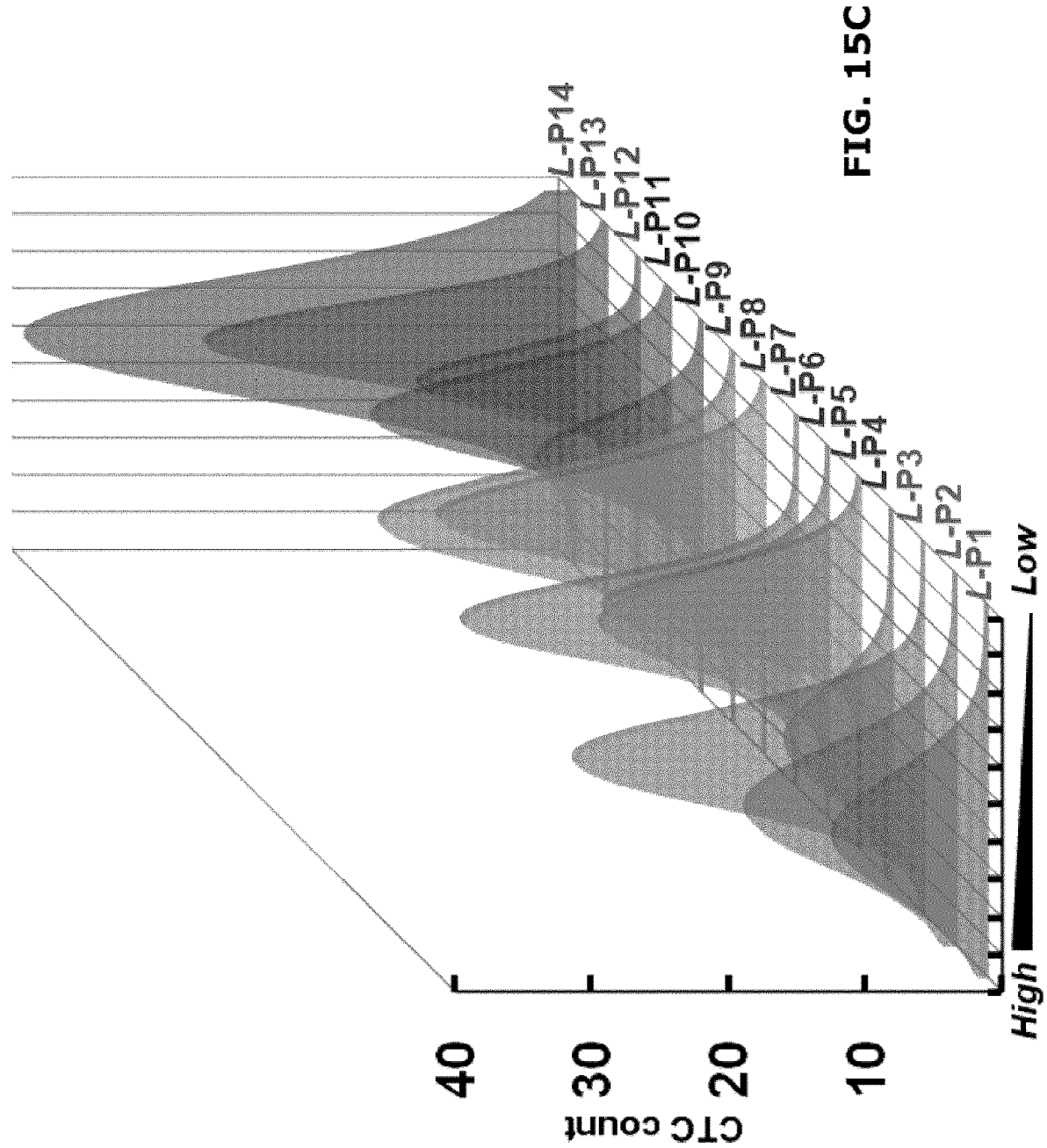

DEVICE FOR MAGNETIC PROFILING OF PARTICLES IN A FLOW

CROSS-REFERENCE TO RELATED APPLICATION

The present disclosure claims priority from U.S. provisional patent application No. 62/233,648, filed Sep. 28, 2015, the entirety of which is hereby incorporated by reference.

FIELD

The present disclosure relates generally to devices for profiling particles, such as rare cells, in a flow. In particular, the present disclosure relates to devices that use magnetism for profiling particles in a flow chamber.

BACKGROUND

The metastasis of cancerous tumors relies on the release of circulating cells that migrate to distant sites and form secondary tumors (1, 2). Profiling phenotypes of rare circulating tumor cells (CTCs) in whole blood is critical for unraveling the complex and dynamic properties of these clinically-important markers. CTCs possess heterogeneous phenotypes that may change as they enter the bloodstream: and while some CTCs possess benign properties, others exhibit much higher metastatic potential. The factors that determine the invasiveness of these CTCs remain poorly defined, and it is not currently possible to distinguish CTCs having high versus low metastatic potential. Studying CTCs directly collected from unprocessed blood samples is a challenge given their rarity in the bloodstream (3, 4). Moreover, these cells are highly heterogeneous given that multiple cell phenotypes can exist within a given tumor, and that their properties evolve dynamically once they leave a tumor and enter the bloodstream (1). The epithelial-to-mesenchymal transition (EMT) in particular is a dynamic process in CTCs and appears to be linked to invasiveness (5, 6), but it remains unknown how EMT status relates to the metastatic potential of these cells.

Recent advances in rare cell capture technology (7-19) have made it possible to isolate CTCs with a high level of sensitivity and specificity. Advanced CTC analysis methods (20, 21) and rare cell profiling tools (22) enable fingerprinting of the genomic or proteomic properties of these cells; however, even the most advanced techniques cannot directly analyze the low numbers of cells found in clinical samples. Profiling CTCs to reveal their phenotypic properties, and in particular their heterogeneity as a function of the status of a tumor, is therefore typically conducted using offline molecular analysis technologies to profile individual cells.

SUMMARY

In some examples, the present disclosure describes a device for magnetic profiling of target particles in a flow. The device may include: a flow chamber; and a plurality of flow rate-reducing structures in the flow chamber, each structure comprising a trapping surface shaped to reduce flow rate in a vicinity of the trapping surface; each flow rate-reducing structure being provided with a localized magnetic attractive force (e.g., provided with a circular nickel micro-magnet that induces the localized magnetic attractive force), the magnetic attractive force defining a capture zone in the vicinity of the flow rate-reducing structure; wherein the magnetic attractive force in the capture zone, is sufficiently high to overcome drag force on a given subset of the target particles to promote capture of any particles belonging to the subset of the target particles in the capture zone; and wherein different target particles having different magnetic susceptibility are captured in different capture zones.

In some examples, the present disclosure describes a device for distinguishing between at least two types of target particles in a flow, a first type having a first magnetic susceptibility, a second type having a second magnetic susceptibility. The device may include: a flow chamber; a plurality of flow rate-reducing structures in the flow chamber, each structure comprising a trapping surface shaped to reduce flow rate in a vicinity of the trapping surface; a plurality of magnetic-force-shaping elements in the flow chamber, the magnetic-force-shaping elements defining a magnetic attractive force in the vicinity of respective flow rate-reducing structures; where the flow chamber includes at least: a first region including flow rate-reducing structures having a first size, and associated with a first magnetic field profile; a second region including flow rate-reducing structures having a second size, and associated with a second magnetic field profile; wherein, in the first region, the first type of target particles is substantially captured as a result of the magnetic attractive force of the first magnetic field profile exceeding the drag force on the first type of particles in the first region; wherein, in the first region, the second type of target particles is substantially flowed through the first region as a result of the magnetic attractive force of the first magnetic field profile being lower than the drag force on the second type of particles in the second region (that is, the capture zone in the first region is not large enough to capture the second type of particles); and wherein, in the second region, the second type of target particles is substantially captured as a result of the magnetic attractive force of the second magnetic field profile exceeding the drag force on the second type of particles in the second region (that is, the capture zone in the second region is sufficient to capture the second type of particles).

In some examples, the present disclosure describes a method for magnetic profiling of target particles in a flow. The method may include: introducing the sample containing the target particles to an example of the devices described herein, the target particles being susceptible to a magnetic attraction force; washing the device of any uncaptured particles; and obtaining an image of captured particles within the device.

BRIEF DESCRIPTION OF THE DRAWINGS

Reference will now be made, by way of example, to the accompanying drawings which show example embodiments of the present application, and in which:

FIG. 4H is an example histopathology image of a lung section of a mouse in the estrogen positive group, confirming the presence of micrometastases;

FIG. 7A illustrates an example velocity field around an example flow rate-reducing structure;

FIGS. 15B and 15C show EpCAM profiles for CTCs captured from samples from patients with metastatic and localized prostate cancer, respectively;

Similar reference numerals may have been used in different figures to denote similar components.

DESCRIPTION OF EXAMPLE EMBODIMENTS

In various examples, the present disclosure describes devices and methods for magnetic profiling of particles, in particular rare cells, in a flow. The example methods may be referred to as Magnetic Ranking Cytometry (MagRC), or more generally as magnetic profiling in a flow. Although the present disclosure provides examples where magnetic profiling is performed on rare cells, specifically CTCs in blood, the disclosed methods and devices may be suitable for magnetic profiling of other cells or other particles in various mediums, with modification as appropriate.

In examples described herein, a microfluidic chip may be used to profile CTCs based on the surface marker expression phenotype of the CTCs, and may be used to do so directly from whole blood. Examples of the present disclosure have been found to have relatively high sensitivity compared to conventional approaches, and have been found to be able to classify CTCs with single-cell resolution according to their expression of phenotypic surface markers. In example studies described here, the disclosed devices and methods were used to reveal the dynamic phenotypes of CTCs in unprocessed blood from mice as a function of tumor growth and aggressiveness.

The present disclosure describes examples of devices that can be used to, in a single measurement, determine the profile of phenotypic properties in a small collection of CTCs isolated from whole blood. This may facilitate the study of how the dynamic changes in these cells relate to tumor growth and metastasis. A high level of sensitivity and resolution would be useful for this purpose.

Figure 1A:
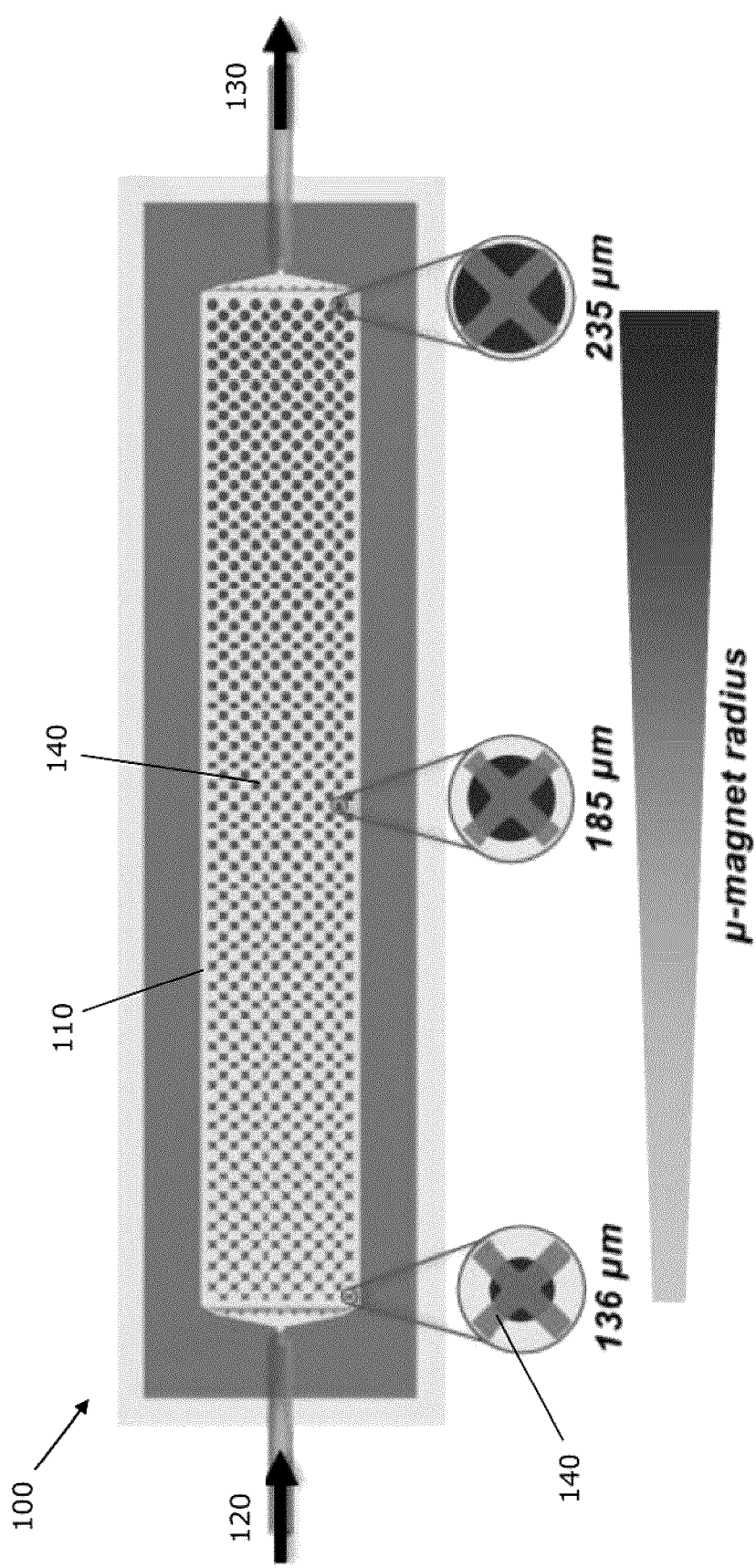
FIG. 1A illustrates an example device for magnetic profiling of particles in a flow.
Figure 1B:
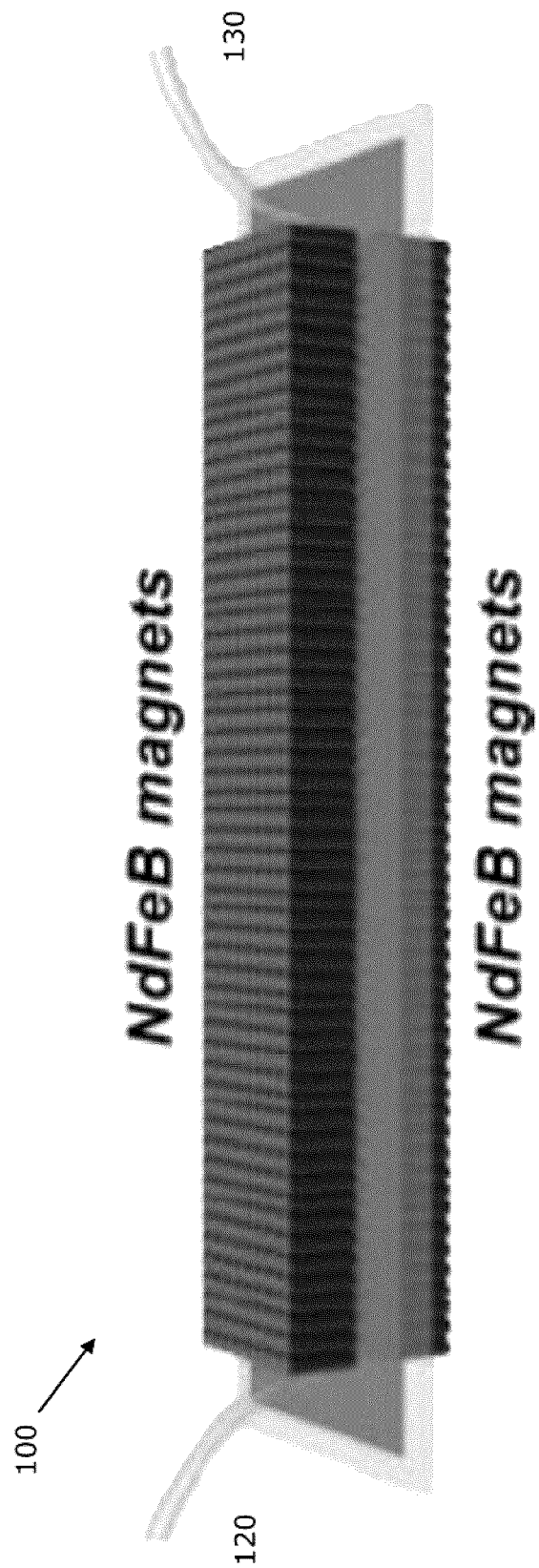
FIG. 1B illustrates an example arrangement of external magnets suitable for use with the example device of FIG. 1A.
Figure 1C:
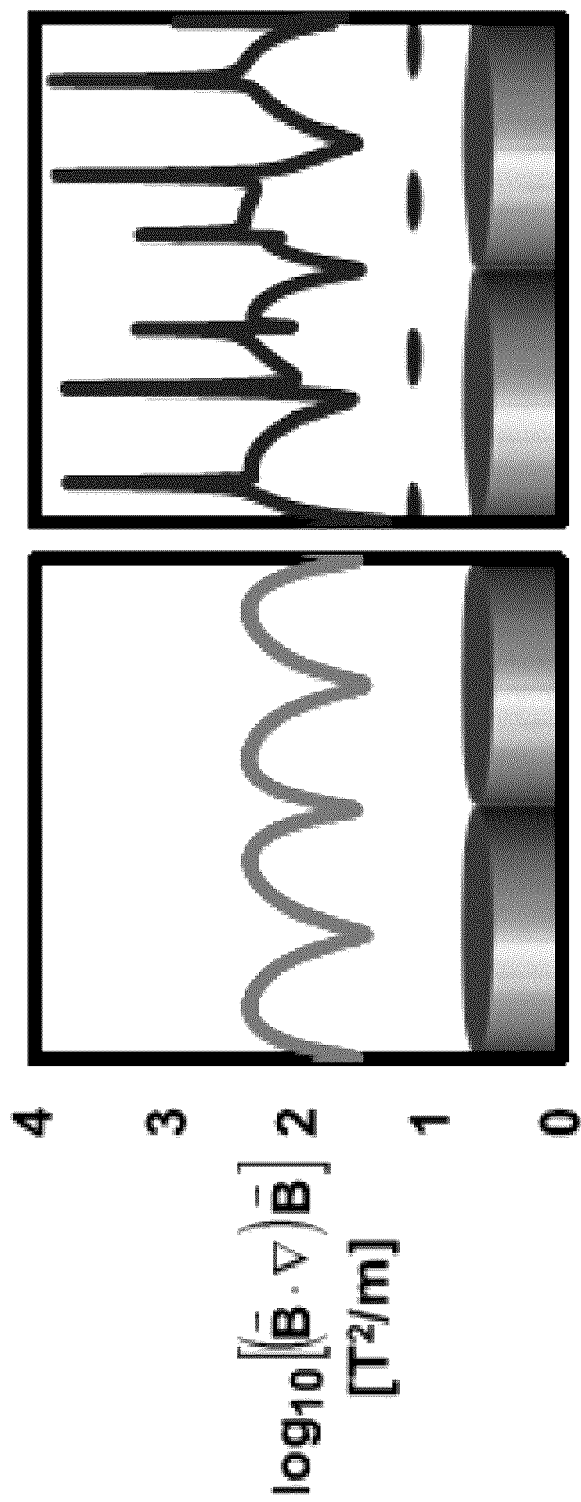
FIG. 1C shows charts representing example external (left) and local (right) magnetic forces experienced by particles in an example device for magnetic profiling.

FIG. 1A shows an example device suitable for magnetic profiling of particles in a flow. The example device 100 may be in the form of a microfluidics-based chip. The device 100 may be used for profiling of surface protein expression in a collection of CTCs, which may be labeled with magnetic nanoparticles. The example device 100 may include a flow chamber 110 in fluid communication with a flow inlet 120 for receiving a sample (e.g., a medium carrying particles for analysis, such as a blood sample containing CTCs as well as other cells) and a flow outlet 130. There may be a plurality of flow rate-reducing structures 140 (in the example shown, X-shaped structures) in the flow chamber 110, which may be similar to the flow rate-reducing structures described in PCT patent application no. PCT/CA2014/050371, the entirety of which is hereby incorporated by reference. The flow rate-reducing structures 140 may serve to locally slow the flow of the sample in the flow chamber 110, to facilitate capture of cells (23, 24). There may be an external magnetic arrangement, for example a set of external NdFeB magnets (see FIG. 1B) positioned on either side of the device 100, which may include one or more magnets, for applying a general (e.g., substantially constant) external magnetic field to the flow chamber 110. Inside the microfluidic channel, magnetically labeled cells are subjected to both the external magnetic field and high-field gradient amplifications generated by the micro-magnets (e.g., nickel micro-magnets). FIG. 1C show charts representing example magnetic fields gradients experienced by magnetically labeled cells due to the external magnetic field (left) and due to high-field gradient amplifications generated by the micro-magnets (right).

Each flow rate-reducing structure 140 may be associated with a respective micro-magnet (e.g., a nickel micro-magnet), which varies the local magnetic force (and hence the capture zone, discussed further below) within the device 100. More generally, there may be magnetic-force-shaping elements that define local magnetic attractive force in the vicinity of each flow rate-reducing structure 140. In FIG. 1A, example flow rate-reducing structures 140 with nickel micro-magnets having radii of 136 µm, 185 µm and 235 µm are illustrated. As the size of the micro-magnets increases, a larger area of the device may be impacted by the heightened magnetic forces acting near the micro-magnet. As magnetically-susceptible particles (e.g., magnetically labeled cells) pass through the flow chamber 110, they may be captured only when they enter into a volume exhibiting a magnetic force that exceeds a threshold for capture. The relative size of the capture volumes exhibiting favorable capture dynamics along the length of the device depends on the magnetic susceptibility of each particle. In the case of magnetically labeled cells, the magnetic susceptibility of a particle is related to the number of bound magnetic nanoparticles; since the number of bound magnetic nanoparticles reflect the surface protein expression level of a cell, the position at which a given cell is captured along the device may be representative of the protein expression level of the cell.

Each of the flow rate-reducing structures 140 associated with a micro-magnet may define a capture zone 145. In the example of FIG. 1A, there may be 100 discrete capture zones 145. Antibody-functionalized magnetic nanoparticles may be introduced into a blood sample to label cells of interest. The labeled blood sample may be introduced into the device 100 and the labeled cells may then be sorted into one of the capture zones 145. This sorting may be achieved according to levels of bound nanoparticles that in turn report on surface expression. As the size of nickel micro-magnets increases (and hence as the local magnetic force increases) along the flow chamber 110, the capture zones 145 increase in size (25). In the example device of FIG. 1A, the radii of the nickel micro-magnets increase linearly by a step size of 1 µm along the length of the flow chamber 110. Decreasing the step size from one micro-magnet to the next may increase the sorting resolution of the device 100, while increasing the step size or varying the size in a non-linear manner may lead to increased specificity in the captured subpopulations. As particles pass through the flow chamber 110, they may be captured when they enter into the volume of the capture zone 145 exhibiting high magnetic field strength and sharp field gradients.

By "capture", it is meant that the particle is deflected from its flow path and held in place within the capture zone 145. Typically, a particle may be captured when the magnetic force of a capture zone 145 is comparable or greater than the drag forces experienced by the particle due to the flow. The amount of deflection depends on the number of bound magnetic nanoparticles on the cell, which reflect the surface protein expression level of a cell.

Cells that are captured in different zones 145 of the device 100 may be imaged by obtaining an image of the device 100 (e.g., using fluorescence imaging) after the sample has been passed through. A profile of the sample may be compiled from the distribution of the cells within the device 100, which reflects phenotypic properties of the cells.

Figure 1D:
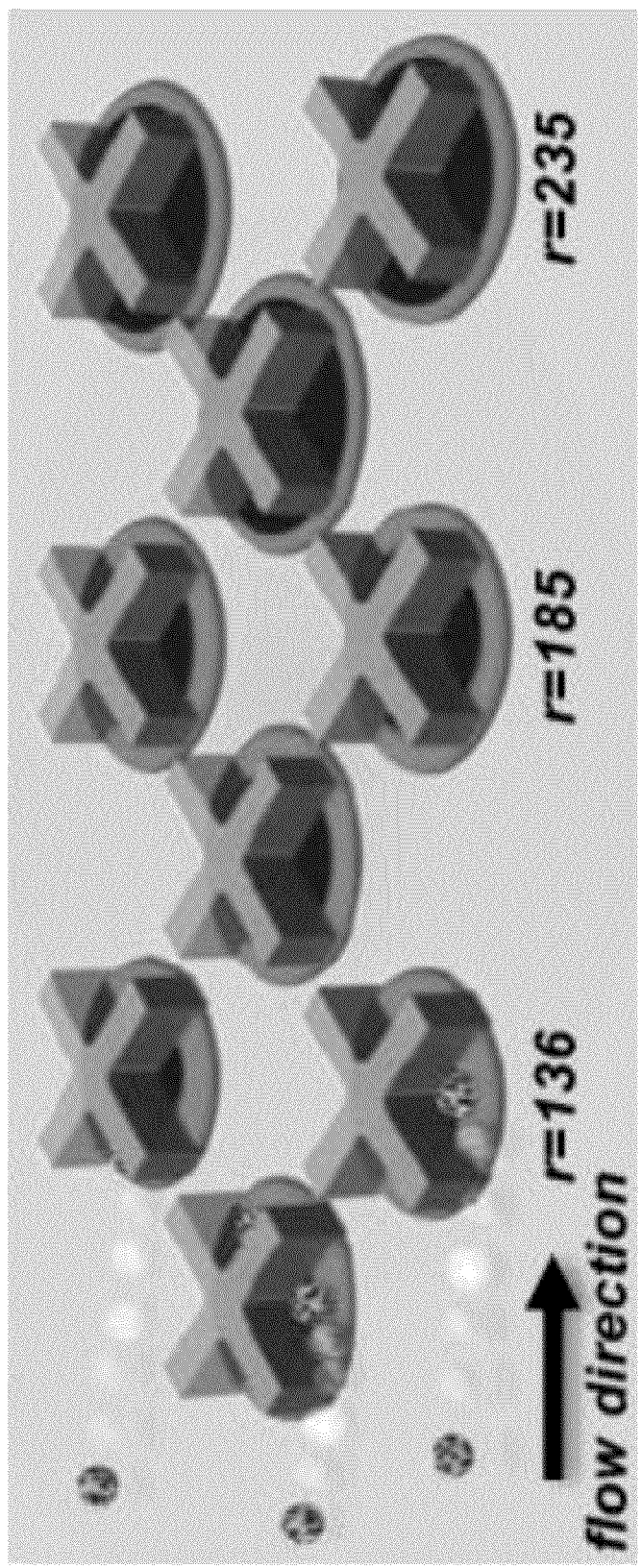
FIGS. 1Di and 1Dii are schematic diagrams representing example capture zones of different particles in an example device for magnetic profiling.
Figure 1E:
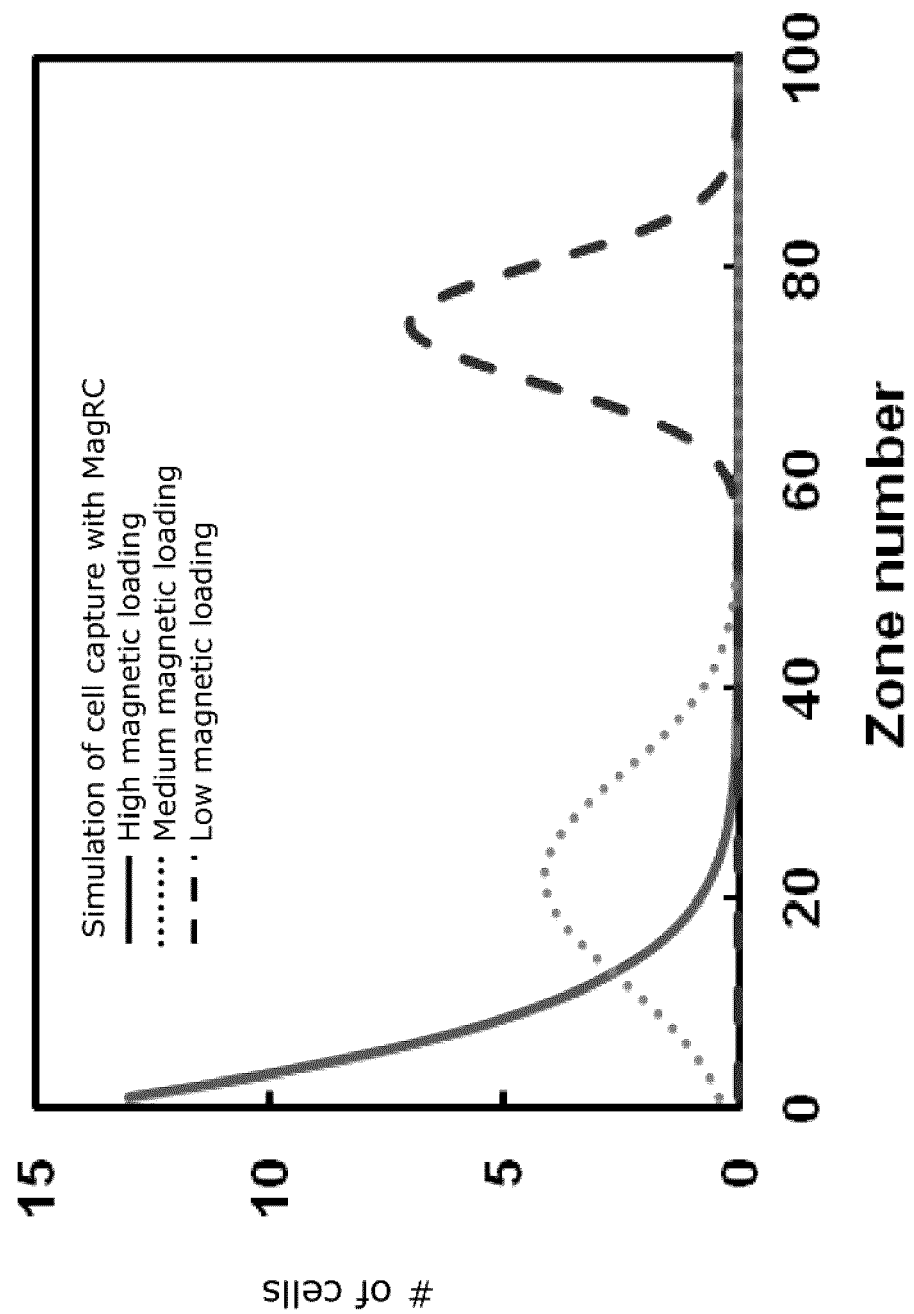
FIG. 1E is a chart illustrating a parametric model for predicting the capture zone where different particles are expected to be captured.
Figure 1F:
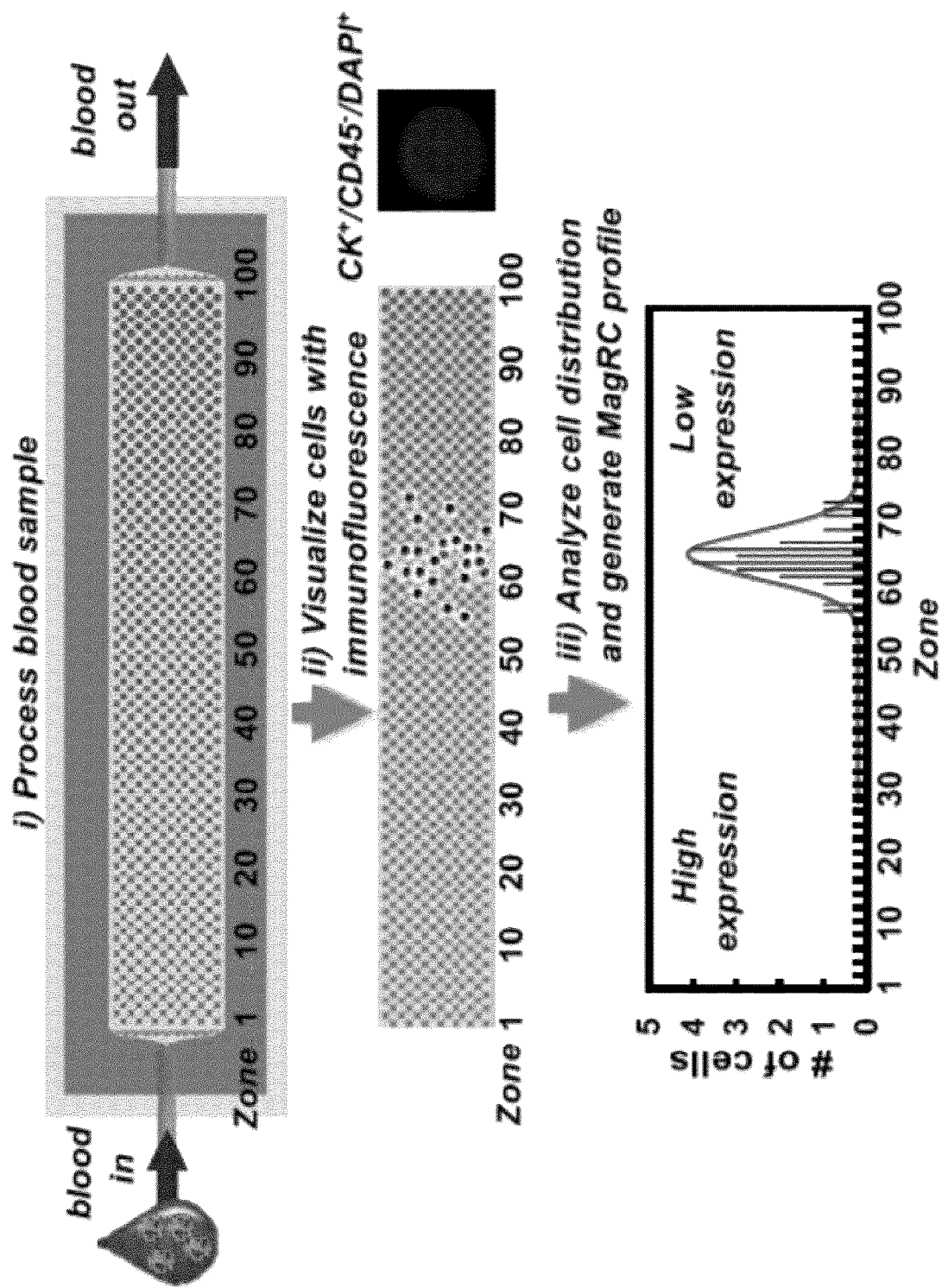
FIG. 1F is a diagrammatic overview of an example method for magnetic profiling of particles in a blood sample.

FIG. 1F illustrates a general overview of an example method for magnetic profiling of particles in a flow. First, a sample (e.g., whole, unprocessed blood) is introduced into the device. Once the sample has been processed through the device, magnetically labeled particles (e.g., CTCs) are expected to be captured by different capture zones, depending on the magnetic attraction as discussed below. Then, the device is washed with buffer. Immunostaining is then used to identify captured CTCs and their distribution within the device. The number of captured cells in each zone is then tabulated and used to generate a profile that reflects levels of protein expression for the cells as a collective.

Computational Modeling

Computational modeling of the example device was pursued to confirm that cells with varied expression levels would generate profiles representative of their individual phenotypes.

A capture zone or volume may be defined as a region in which the magnitudes of the magnetic and drag forces experienced by a given cell are comparable, with the result that given cell passing through the capture zone is expected to be captured. In examples disclosed herein, the capture regions increase in size with increasing radius of the nickel micro-magnet.

A cell with a high level of surface expression would be expected to be labeled with a high number of bound magnetic nanoparticles. For a cell with a high level of bound magnetic nanoparticles, the capture zone generated by even the smallest micro-magnets may be sufficient to ensure capture in the upstream zones (in examples where the strengths of micro-magnets increase along the flow stream) of the device. Therefore, cells with higher expressions may be expected to be captured in the upstream zones of the device, where the micro-magnets are smaller. However, lower expression cells (which are expected to be labeled with a lower number of bound magnetic nanoparticles) may be deflected and captured only if they are close to the edges of the micro-magnets, where the magnetic force acting on the bound nanoparticles is highest. For these lower expression cells, larger micro-magnets may be required to generate a large enough capture zone, leading to capture in downstream zones of the device. This is illustrated by FIGS. 1Di and 1Dii.

In these FIGS. 1Di and 1Dii, the micro-magnets associated with the flow rate-reducing structures increase in size in the downstream direction. The green annuli represent capture regions where cells with varied levels of bound magnetic nanoparticles are predicted to be captured efficiently. CTCs with higher levels of surface marker expression (and hence greater labeling by magnetic nanoparticles) experience larger effective capture regions as they flow through the device, since they require less field amplification to generate comparable magnetic forces. Cells with higher levels of surface marker expression (and thus high magnetic loading) are expected to be captured in the earliest zones where the micro-magnets are small (see FIG. 1Di), while for lower expression cells, the larger micro-magnets found further downstream in the device may be required to generate a sufficiently large capture region (see FIG. 1Dii).

In the example device, each micro-magnet may be positioned substantially in the center of the flow rate-reducing structure. In the case where the flow rate-reducing structure is rotationally symmetrical (e.g., an X-shaped structure), the regions in exhibiting the highest magnetic forces and field gradients may also be the regions subjected to the slowest flows. This may result in creation of localized regions with favorable capture dynamics (i.e., low drag and high magnetic forces), while also contributing to the high-resolution sorting capabilities of the device. Modeling results (see FIG. 1E) show the predicted capture locations for three types of cells having high, medium and low levels of magnetic loading, respectively. Details of an example computer simulation are discussed below.

In order for cells to be captured in the example device, the magnetic forces acting on the cells must be large enough to induce a significant transverse velocity, drawing the cells across the flow streamlines and towards the walls of the device. Once cells are brought into contact with the walls, capture will occur if the combination of magnetic, friction, adhesion and normal forces acting on the cells is large enough to balance the drag force generated by the flow.

To determine where capture will occur in the device for cell lines having high, medium and low levels of magnetic loading, magnetic and flow field simulations were carried out in COMSOL Multiphysics®, with the goal of comparing the magnitude of the flow velocity at each point in the device with the magnitude of the velocity expected to be generated by the magnetic force acting on the cells at that point. In this simulation, the magnetically induced velocity was determined from Stokes law, $$V_m = \left(\frac{F_m}{6\pi\mu r}\right).$$

Figure 5:
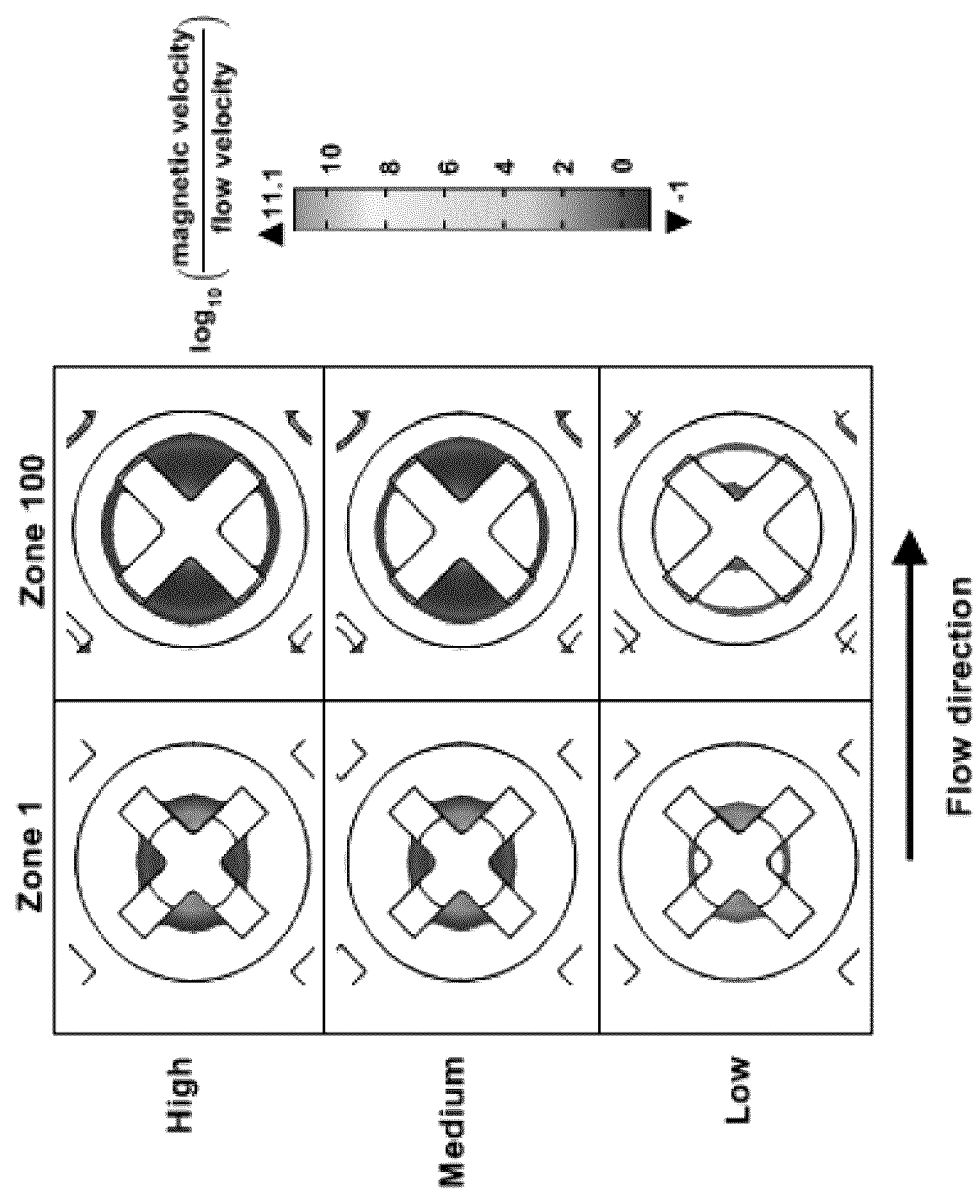
FIG. 5 illustrates capture zones in an example device for magnetic profiling of particles in a flow.

Since the height of the device is very small compared to its length and width, even a moderate deflection induced by magnetic forces in the path of a cell will result in that cell being brought into contact with the walls of the device. As a result, any region where the magnitude of the magnetically induced velocity comparable to (or greater than) the flow velocity was deemed in the simulation to be a "capture region". Capture regions for different cell lines in zones 1 & 100 at a height of 10 µm are highlighted in FIG. 5. FIG. 5 shows example analysis of capture regions for cell lines with varied expression levels and nanoparticle loading in the first (i.e., most upstream) and last (i.e., most downstream) zones of the example device at a height of 10 µm from the bottom of the device. Capture radius was evaluated at heights ranging from 5 µm to 45 µm.

Two characteristics may be observed in FIG. 5; first, the capture regions were found to increase in size with increasing micro-magnet radius, and second, the radius of each capture region was found to extend further from the front and back (i.e., the upstream and downstream directions) of the flow rate-reducing structures, in the example where the flow rate-reducing structures are X-shaped structures, than from the sides (where the front, back and sides of the flow rate-reducing structures are defined by their orientation in the flow—that is, "front" corresponds to the upstream direction and "back" corresponds to the downstream direction). The asymmetry in the extent of the capture region is caused by asymmetry in the flow profile around the flow rate-reducing structures, with stagnation points generated at the front and back of the flow rate-reducing structures. FIG. 7A illustrates the velocity field around an example X-shaped flow rate-reducing structure at a height of 25 µm (mid-plane) in the device, showing the stagnation points at the front and back of the flow rate-reducing structure.

Figure 6:
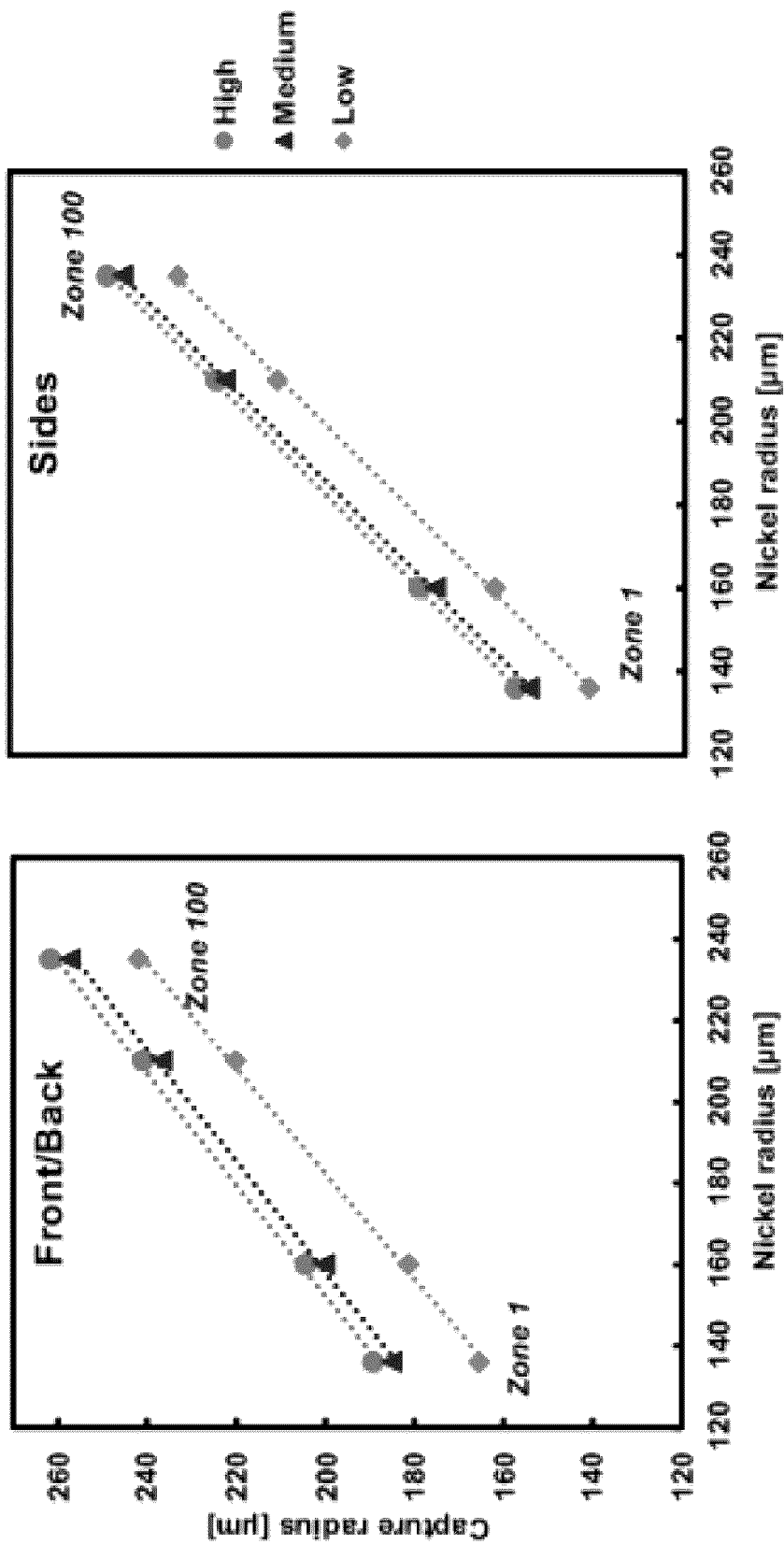
FIG. 6 shows charts illustrating calculations of the capture radius for different micro-magnets in an example device for magnetic profiling of particles in a flow.

In order to determine the size of a capture region for the three model cell lines in each zone of the chip at every vertical position, the radius (measured from the center of the flow rate-reducing structures) of the capture region for both the front/back and sides of the flow rate-reducing structures was measured at 5 µm height increments (from 5 µm to 45 µm) at multiple zones along the length of the device. Linear functions were then fitted to the capture radius data at each vertical position in the device; a sample of these linear functions, plotted against micro-magnet radius, is shown in FIG. 6. Linear interpolation was used to determine the radius of a capture region for any height between the measured 5 µm height increments. FIG. 6 illustrates calculation of the capture radius versus nickel micro-magnet radius for the front/back and the sides of the X-shaped flow rate-reducing structures (left and right charts, respectively) at a height of 10 µm. The dotted lines represent linear functions fitted to the data for each model cell line.

Figure 7B:
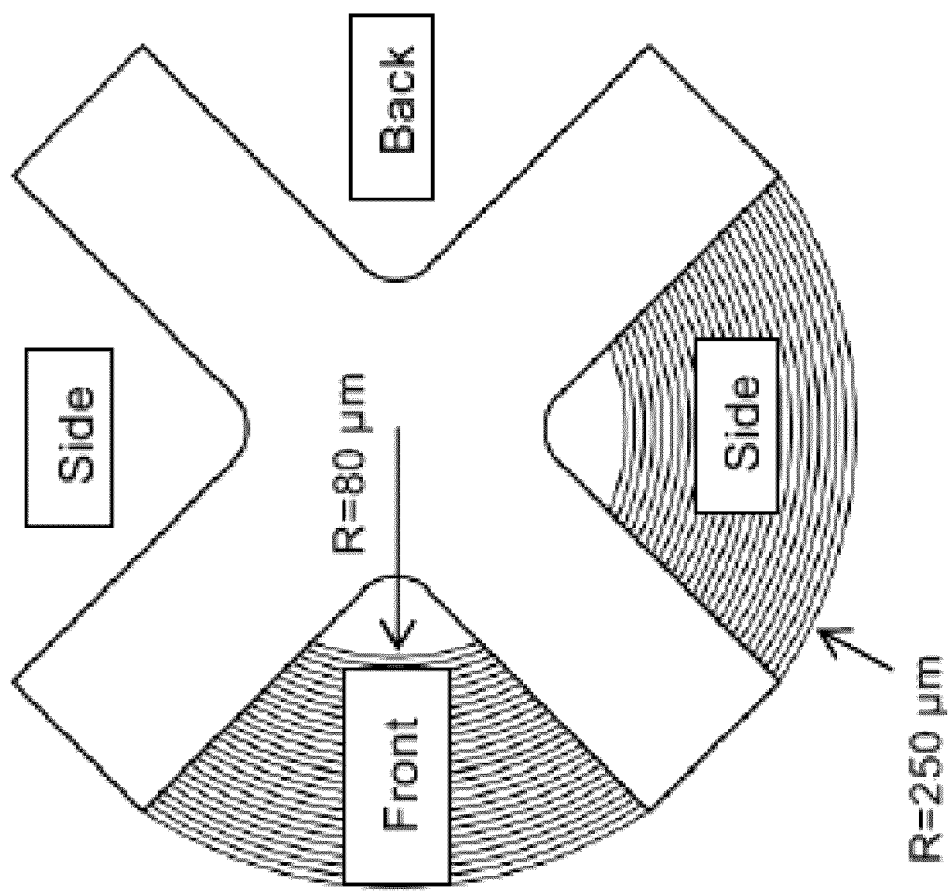
FIG. 7B illustrates control surfaces for volume flux calculations in an example flow rate-reducing structure.
Figure 7C:
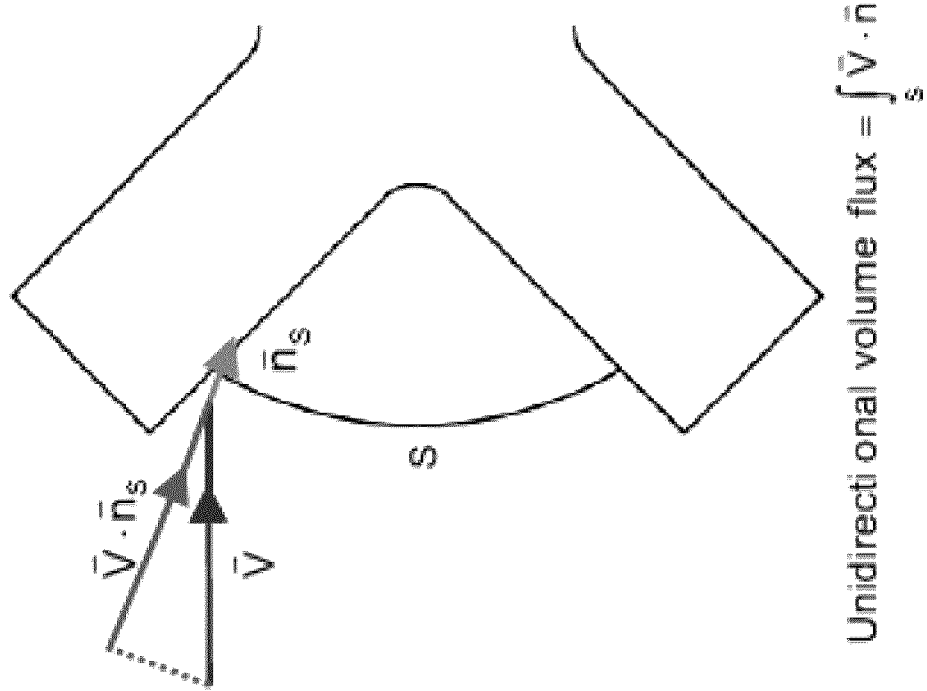
FIG. 7C illustrates surface integral calculation of volume flux in an example flow rate-reducing structure.
Figure 7D:
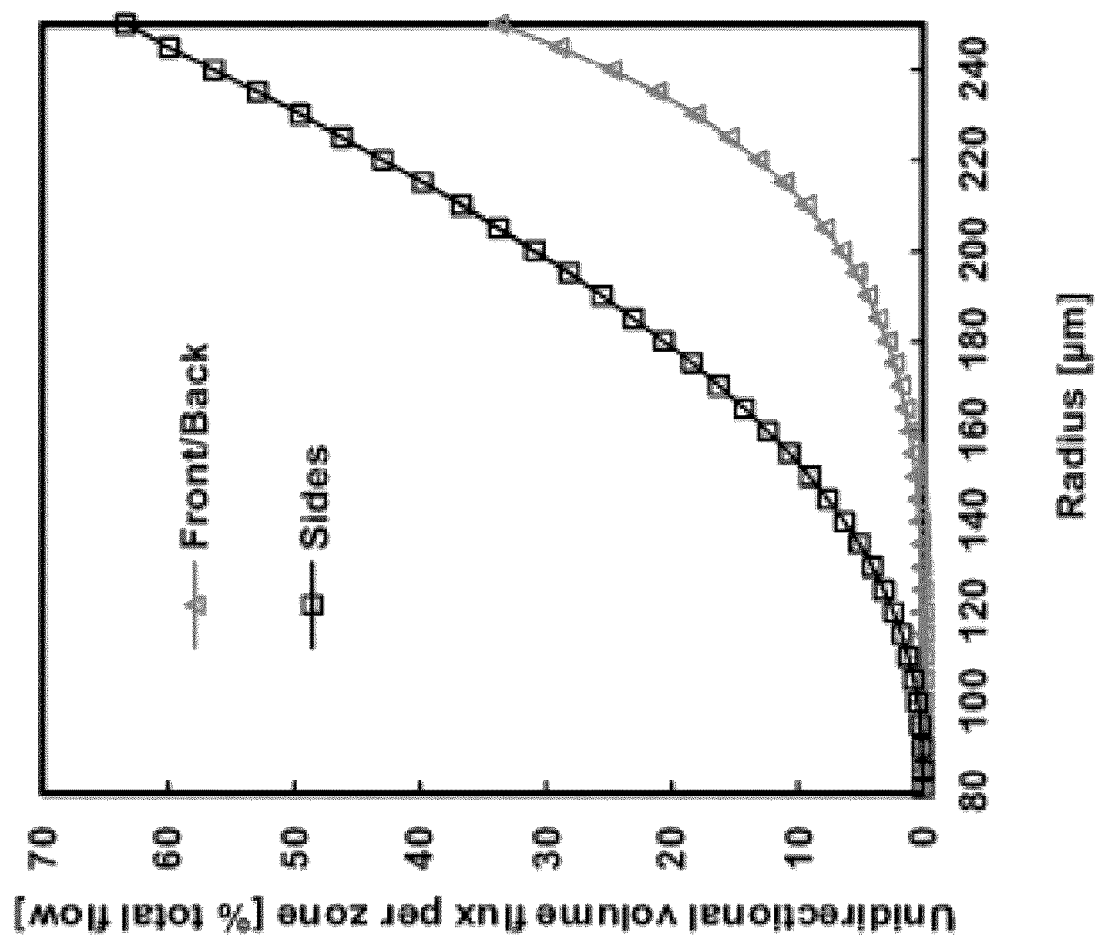
FIG. 7D is a chart illustrating unidirectional volume flux in an example flow rate-reducing structure.

To quantify the likelihood that a cell flowing through the MagRC device will encounter a capture region, the flow field around a flow rate-reducing structure was modeled using COMSOL Multiphysics®. An example result is illustrated in FIG. 7A. A series of concentric control surfaces were defined every 5 µm from the innermost to the outermost radial positions from the center of the flow rate-reducing structures (see FIG. 7B). The volume flux crossing each control surface was determined by integrating the dot product of the velocity vector at the surface with the surface unit normal vector over the control surface area (see FIG. 7C). Since the intersection of each arm of each flow rate-reducing structure is a dead end, the net volume flux across each control surface was necessarily zero; however, by evaluating only the positive contributions to the volume flux, the unidirectional volume flux may be determined, essentially the amount of fluid changeover at a given radial position from the center of a flow rate-reducing structures. The unidirectional volume flux at different radial positions is plotted in FIG. 7D (as a percentage of the total flow rate).

Figure 8:
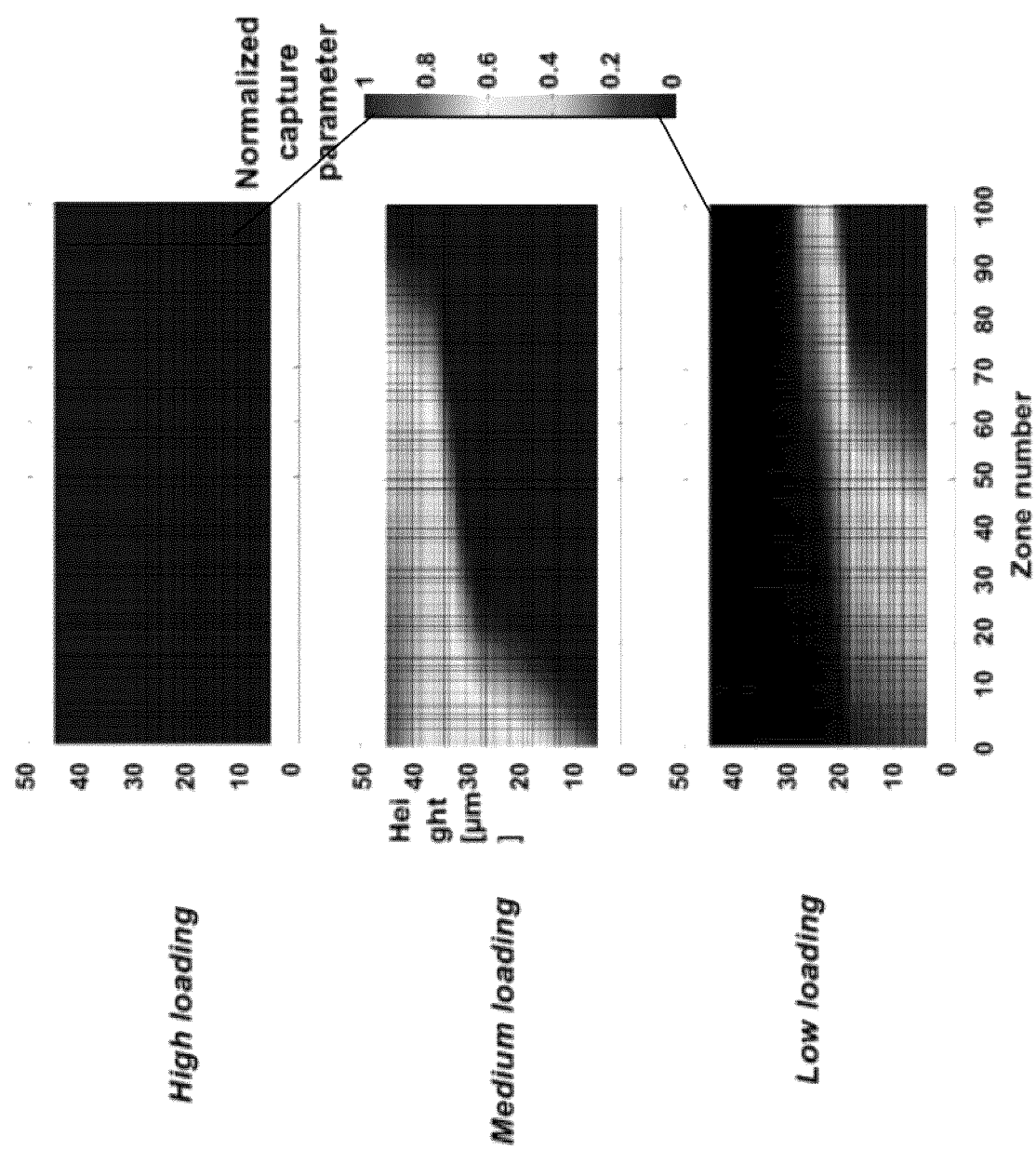
FIG. 8 shows charts illustrating normalized capture parameters for different model cell lines in an example simulation.

A parametric model incorporating the above capture region and flow analysis was developed and implemented in MATLAB® to identify the likely capture location of a cell in the example device. Thousands of model cells were simulated, each having a randomly assigned initial height ranging from 5 µm to 45 µm at the inlet of the device. For each cell in each zone, the percentage chance of that cell encountering a capture region was calculated and reported as the capture parameter (with the size of the capture region calculated using the cell's vertical position and zone number). Cells with a capture parameter of 25% or greater in a given zone were deemed to be eligible for capture. Once a cell's capture parameter was above the 25% threshold, a random number generator was used to determine whether that cell would be captured in the given zone (with the chance of capture directly proportional to the capture parameter). Introducing an element of chance into the parametric model was useful and helped to mimic variabilities in cell magnetization within cell lines, inconsistencies in the flow field, and cell-cell collisions. The capture parameter within the example device for the three model cell lines (normalized so that the 25% threshold for capture is equal to unity) is presented in FIG. 8.

Figure 9:
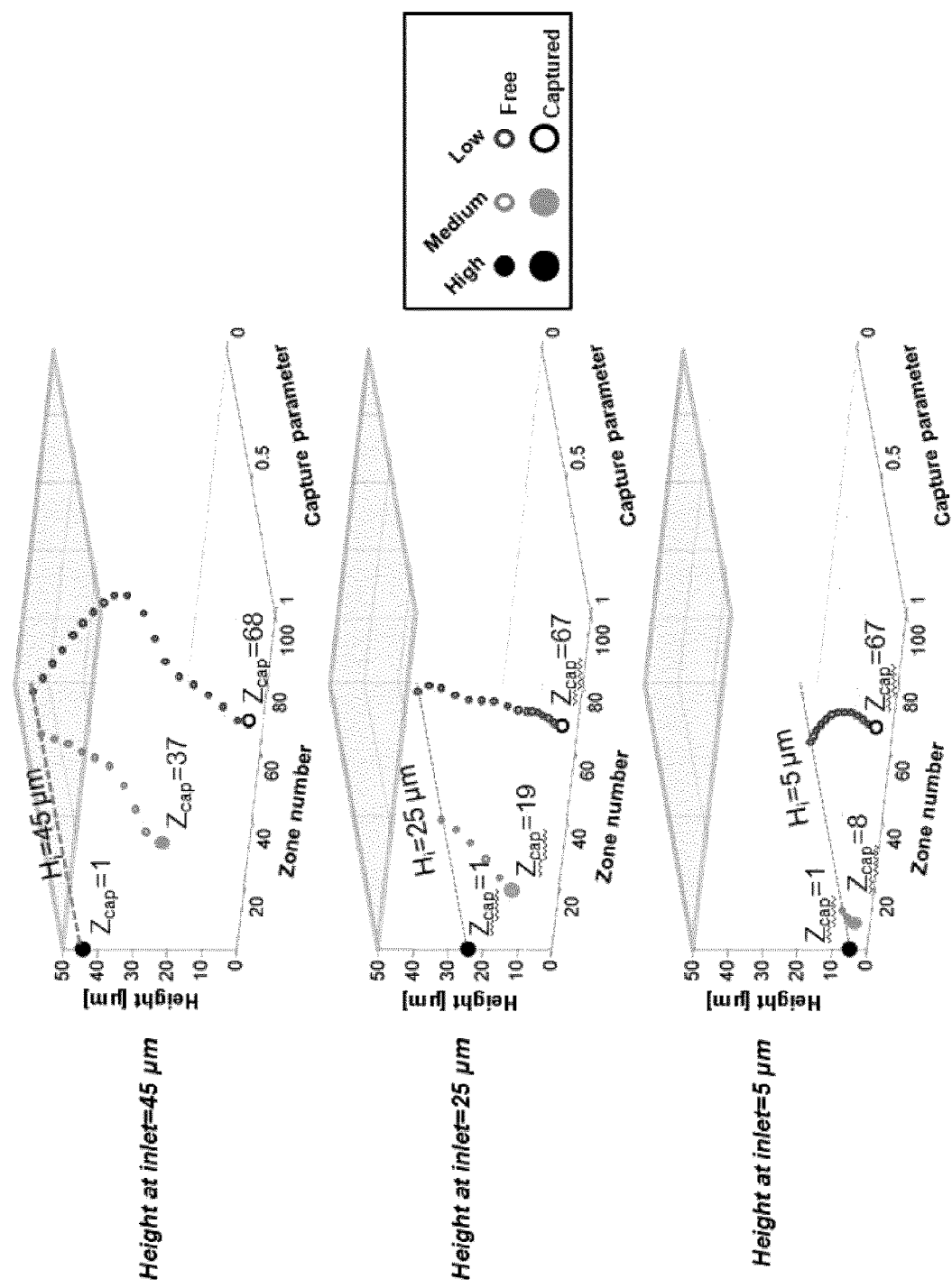
FIG. 9 shows charts illustrating normalized capture parameters as a function of height and capture zone in an example simulation.

Since the micro-magnets generate amplified magnetic fields near the bottom of the microfluidic channel, the capture parameter of the cells within the device was found to be strongly dependent on their vertical position. Additionally, the long length of the device relative to its height (in this example, 8.75 cm vs. 50 µm, respectively) leads to long residence times and the potential for cells to settle towards the bottom of the device. To account for gravitational settling, a linear settling function was incorporated which imposed a 0.5 µm/zone drop in height for uncaptured cells (28). The vertical dependency of the parametric model is illustrated in FIG. 9, for three different inlet heights.

Example Fabrication Method

An example fabrication method of an example of the disclosed device is now described.

In this example, glass substrates obtained from EMF-Corp (Ithaca, N.Y.) were used to fabricate the example device. A 1.5 µm Ni layer was sputtered onto the glass slides. The micro-magnet structures (in this case, nickel micro-magnets) were patterned using standard contact lithography processes. First, a positive photoresist layer (S1811) was spin-coated onto the Ni coated glass. The photoresist was exposed to UV light for 10 seconds before being developed in photoresist developer. This was followed by Ni wet etching to reveal micro-magnets, after which the remaining photoresist was stripped away. To pattern the flow rate-reducing structures (in this example, X-shaped structures) on top of Ni micro-magnets, a thick negative photoresist, SU-8 3050 (Microchem, Newton, Mass.) was spin-coated on top of the nickel coated glass substrates followed by 30 minutes soft-baking. The final thickness of SU-8, and thus the height of channel, was 50 µm. After exposing for 20 seconds, the SU-8 layer was developed using SU-8 developer. Once the micro-magnets and channel structures were completed, the channel was topped with a flat layer of cured polydimethylsiloxane (PDMS). Holes were punched in the PDMS layer, and Teflon tubing was inserted to act as inlet and outlet ports.

Example Studies on Cancer Cell Lines

The example device, fabricated as described above, was used in several example studies with cancer cell lines.

MDA-MB-231, SKBR3 and VCaP cell lines were obtained from American Type Culture Collection (ATCC). MDA-MB-231 cells were cultured in Leibovitz's L-15 medium (ATCC), SKBR3 cells were cultured in McCoy's 5a Medium Modified (ATCC) and VCaP cells were cultured in DMEM (ATCC). All of the media were supplemented with 10% fetal bovine serum (FBS). MCF-7/Luc human breast cancer cells were purchased from Cell Biolabs Inc. and grown in DMEM (High Glucose) supplemented with 10% FBS, 0.1 mM MEM Non-Essential Amino Acids (NEAA) and 2 mM L-glutamine.

Fresh blood was collected from healthy volunteers, and immediately used for experiments. Different numbers of SKBR3 cells were spiked into whole blood. After this step, some samples underwent an additional RBC lysis step; 1 mL of RBC lysis buffer was used, and this was followed by two washing steps with PBS. Lastly, both whole and RBC-lysed blood samples were run through the MagRC chip and analysed via flow cytometry.

SKBR3 cells were seeded in 6-well plates ($4 \times 10^5$ cells/well). After 24 hours, cells were treated with $CoCl_2$ solution at the final concentration of 150 µM. Cells were incubated for 72 hours in a conventional incubator (37° C.; 5% $CO_2$). After this period, cells were harvested using trypsin.

All animal experiments were carried out in accordance with the protocol approved by the University of Toronto Animal Care Committee. 6- to 8-week-old female SCID-beige mice were purchased from Charles River and maintained at the University of Toronto animal facility. 2 days prior to tumor implantation, a subset of mice received a subcutaneous pellet of 60-d sustained release 17-β-estradiol (0.72 mg/pellet; Innovative Research of America). Tumor xenografts were generated by injecting $5 \times 10^6$ cells suspended in 50 µl of Matrigel (BD Biosciences) orthotopically into the 4th left inguinal mammary fat pad. Mice were anaesthetized by isoflurane before injection. Tumor growth was measured both by caliper and by imaging using a Xenogen IVIS Spectrum imaging system (Caliper Life Sciences). Prior to imaging, mice were injected intraperitoneally with 100 µl of phosphate-buffered saline containing D-Luciferin substrate (PerkinElmer). At the end of the experiment, animals were euthanized and selected tissues were analyzed by ex-vivo imaging for micro-metastasis detection.

For intermediate CTC capture from tumor bearing mice, 50-100 µl of blood was collected from the saphenous vein and for the terminal studies 0.5 ml-1 ml blood was collected from each mouse by cardiac puncture. All blood samples were collected in K2EDTA tubes (Microvette, Sarstedt).

Collected mouse blood was diluted with PBS-EDTA (100 µL of PBS-EDTA was added to 50 µL of blood). This was followed by adding 10 µL of anti-EpCAM Nano-Beads (MACS) to 150 µL of diluted blood. After 30 minutes incubation with the magnetic beads, blood was pumped through the example device at a flow rate of 500 µL/h. Next, 200 µL PBS-EDTA was introduced to flush away any non-magnetically captured non-target cells. Captured cells were then fixed with 4% paraformaldehyde, and then permeabilized with 0.2% Triton X-100 (Sigma-Aldrich) in PBS. Anti-CK-APC (GeneTex) antibody was used to stain CTCs, and mouse cells were marked by anti-mouse-H-2K-FITC antibody to distinguish with CTCs. All antibodies were prepared in 100 μL of PBS and pumped through the device at a flow rate of 50 μL/hr for 2 hrs. After immunostaining, the devices were washed using 0.1% Tween 20 in PBS. Cell nuclei were stained with 100 μl DAPI ProLong Gold reagent (Invitrogen, CA) at 500 μL/h. After completion of staining, all devices were washed with PBS and stored at 4° C. before scanning.

After terminal blood collection, animals were euthanized and lungs, liver, lymphnodes were extracted and fixed in 10% buffered formalin. Fixed tissues were then embedded in paraffin for histological examination with hematoxylin and eosin (H&E) staining.

After immunostaining, devices were scanned using a Nikon microscope under 10× objective, and images were acquired with NIS-Elements AR software. Bright field, red (APC channel), green (FITC channel) and blue fluorescence images were recorded. The captured images were then analysed and target and non-target cells were counted.

Discussion of Example Studies

As a first suite of experiments to challenge the performance of the disclosed device, the profiling capabilities of an example of the disclosed device was investigated with three cancer cell lines. As an initial profiling marker, EpCAM was selected; EpCAM is a well-characterized marker present on the surface of many different types of cancer cells and that has levels that are known to vary during EMT (5). Three different cell lines, VCaP (a human prostate cancer cell line), SKBR3 (a breast adenocarcinoma cell line), and MDA-MB-231 (a breast cancer cell line with mesenchymal characteristics), were incubated with anti-EpCAM functionalized magnetic nanoparticles and analyzed with the example device. One hundred cells in buffered solution were introduced into the device, captured, and stained with a nuclear marker. The cells present in different capture zones were then enumerated using fluorescent microscopy.

Figure 2A:
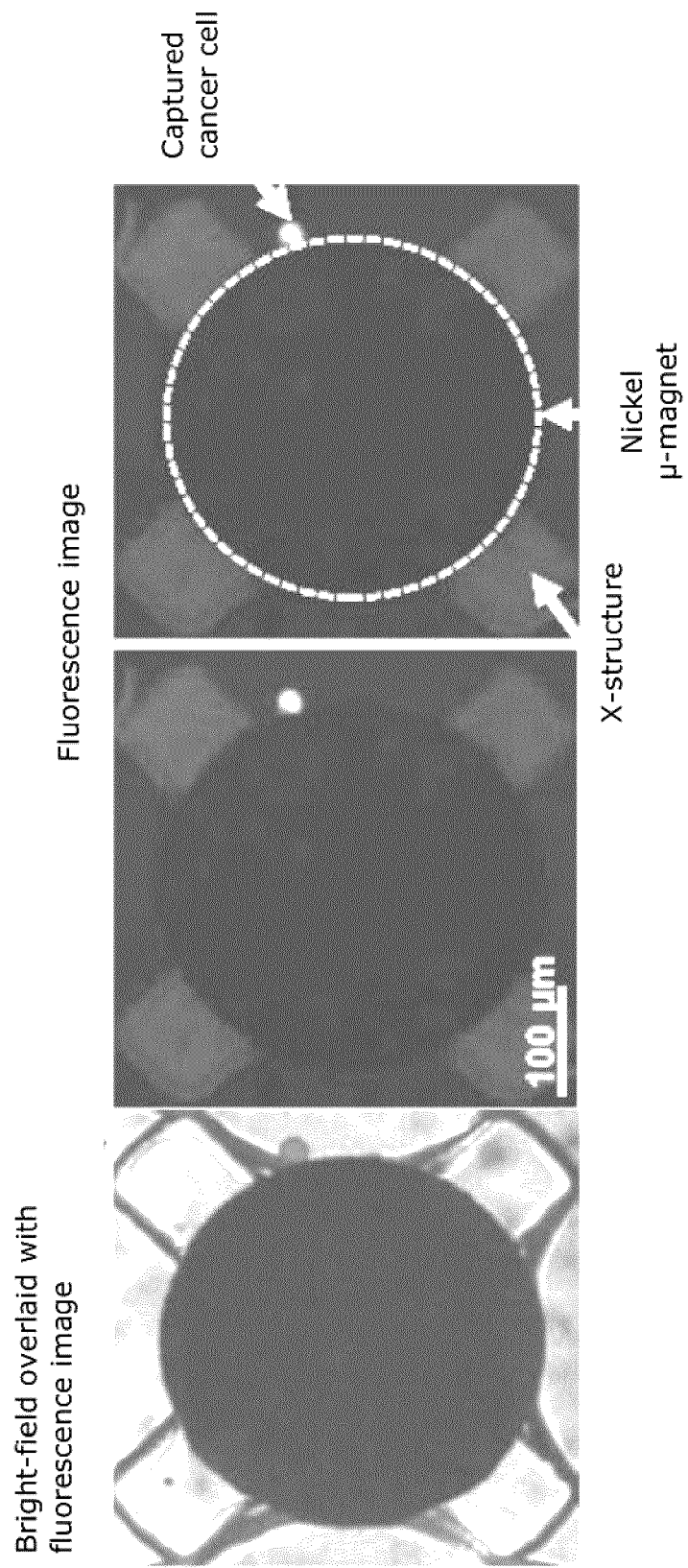
FIG. 2A shows bright-field and fluorescent microscope images of an example captured cancer cell.

FIG. 2A shows example bright field (left) and fluorescent (right) microscope images of a SKBR3 cell captured at the edge of a nickel micro-magnet (where the magnetic field and field gradients are at a maximum). The three different cell lines exhibited distinctly different and highly reproducible profiles of distribution within the device.

Figure 2B:
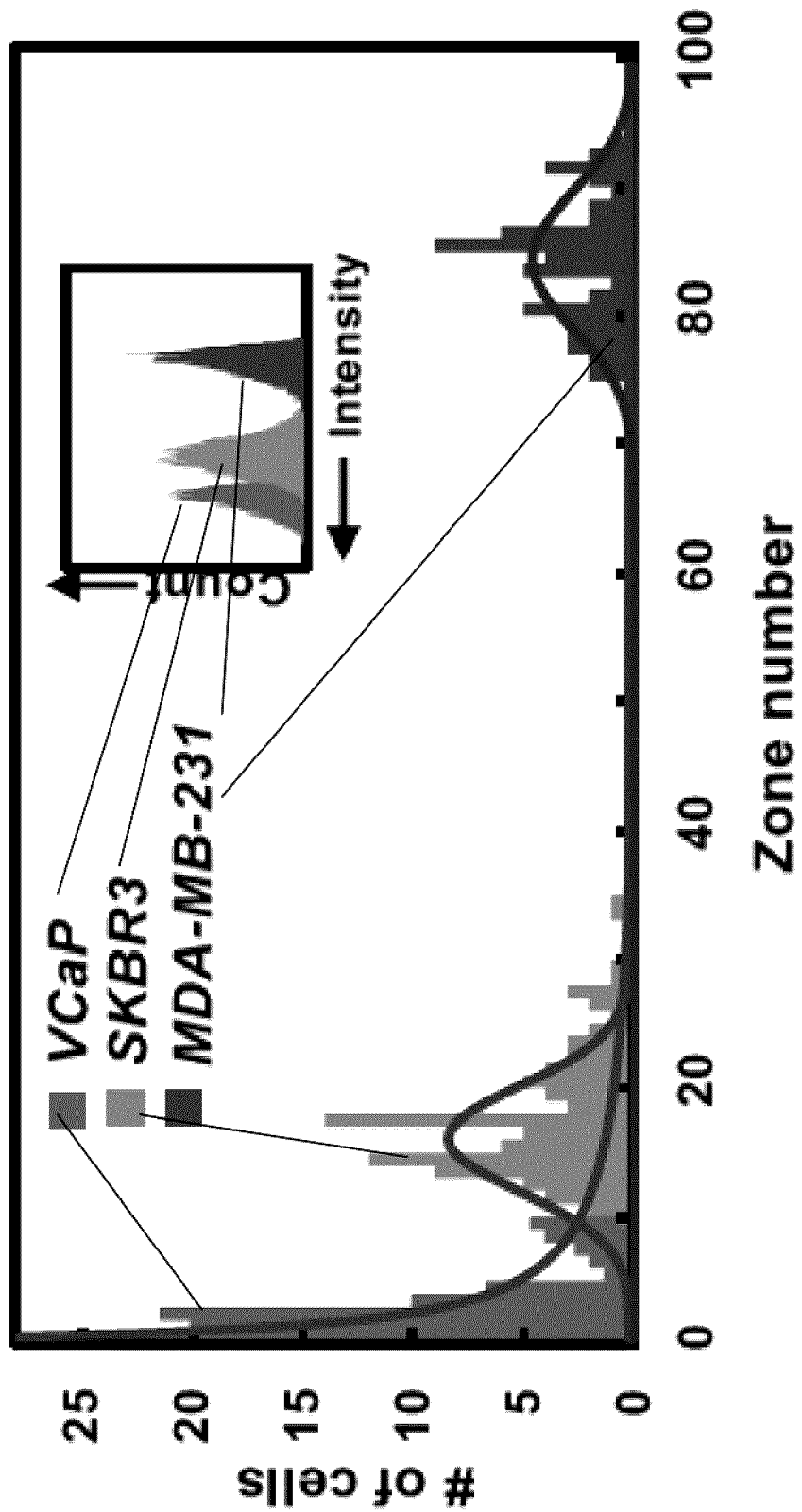
FIG. 2B is a chart illustrating resulting distribution of different cancer cells in an example application of magnetic profiling.

FIG. 2B shows example distributions of VCaP, SKBR3, and MDA-MB-231 cells in the example device; EpCAM was used as the profiling marker. 100 cells suspended in 100 μl of buffer were used in these trials. For comparison, the inset figure shows EpCAM expression measured by flow cytometry for the three cell lines. The profiles that were collected using the example device were found to mirror those collected using conventional flow cytometry as a readout.

VCaP cells, which possess the highest level of EpCAM expression, were found primarily in the first 10 zones of the device (in the example where the earlier or more upstream capture zones have smaller micro-magnets than later or more downstream capture zones). SKBR3 cells, which exhibit an approximately 10-fold lower level of EpCAM expression than VCaP (23) and hence retain a lower number of bound magnetic tags, were captured mainly after zone 10. MDA-MB-231 cells, which had the lowest level of EpCAM expression, were found generally after zone 70 in the region of the device where the micro-magnets are largest. In sum, magnetic ranking cytometry was found to successfully sort cells according to their expression level of surface markers. Importantly, high recoveries of the cells injected into the example device were found to be achieved (VCaP 96±4%, SKBR3 93±4%, MDA-MB-231 94±5%).

Figure 10:
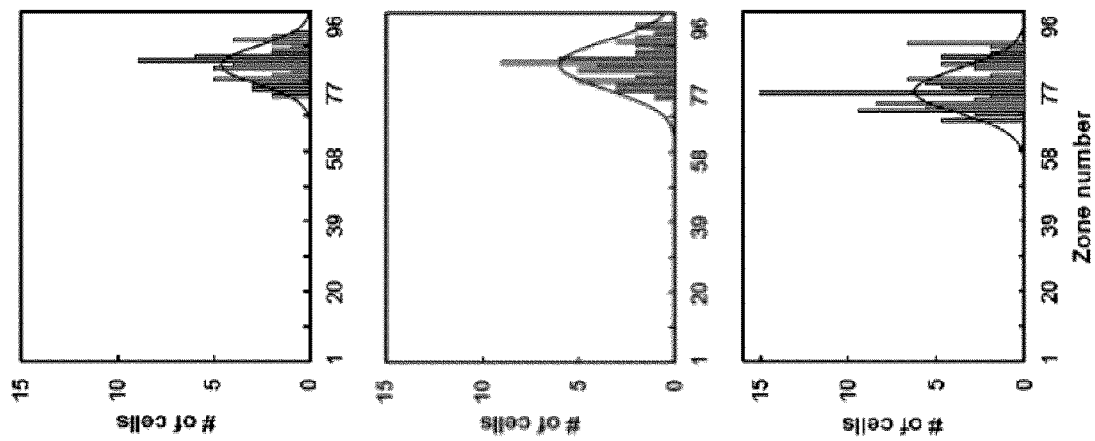
FIG. 10 shows charts demonstrating reproducibility of magnetic profiling tested experimentally.
Figure 10:
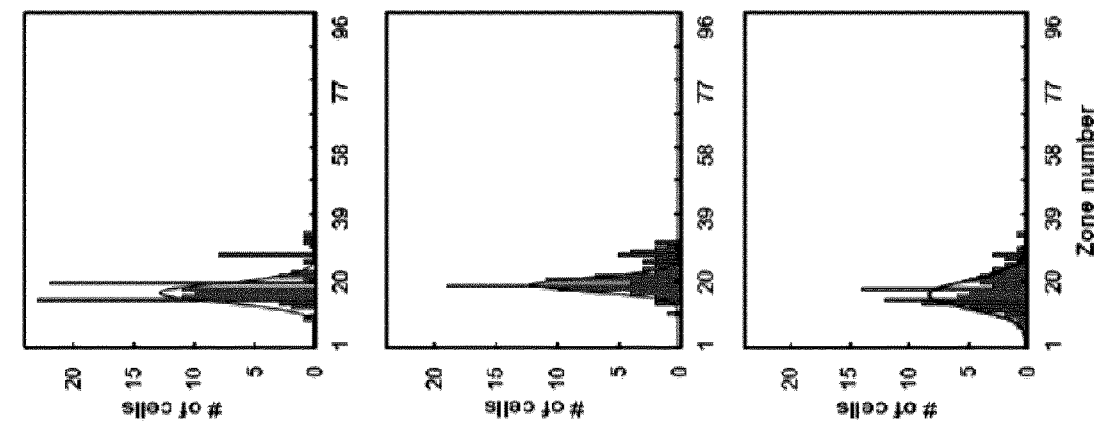
Figure 10:
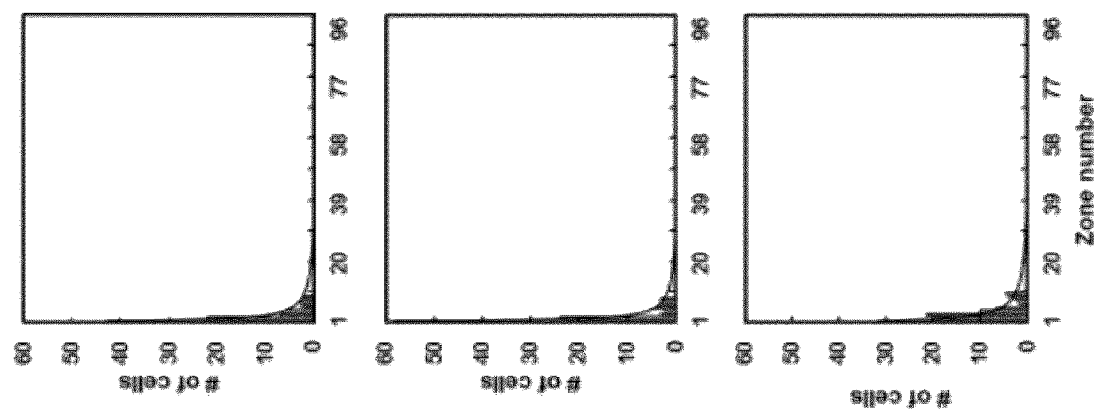
Figure 11:
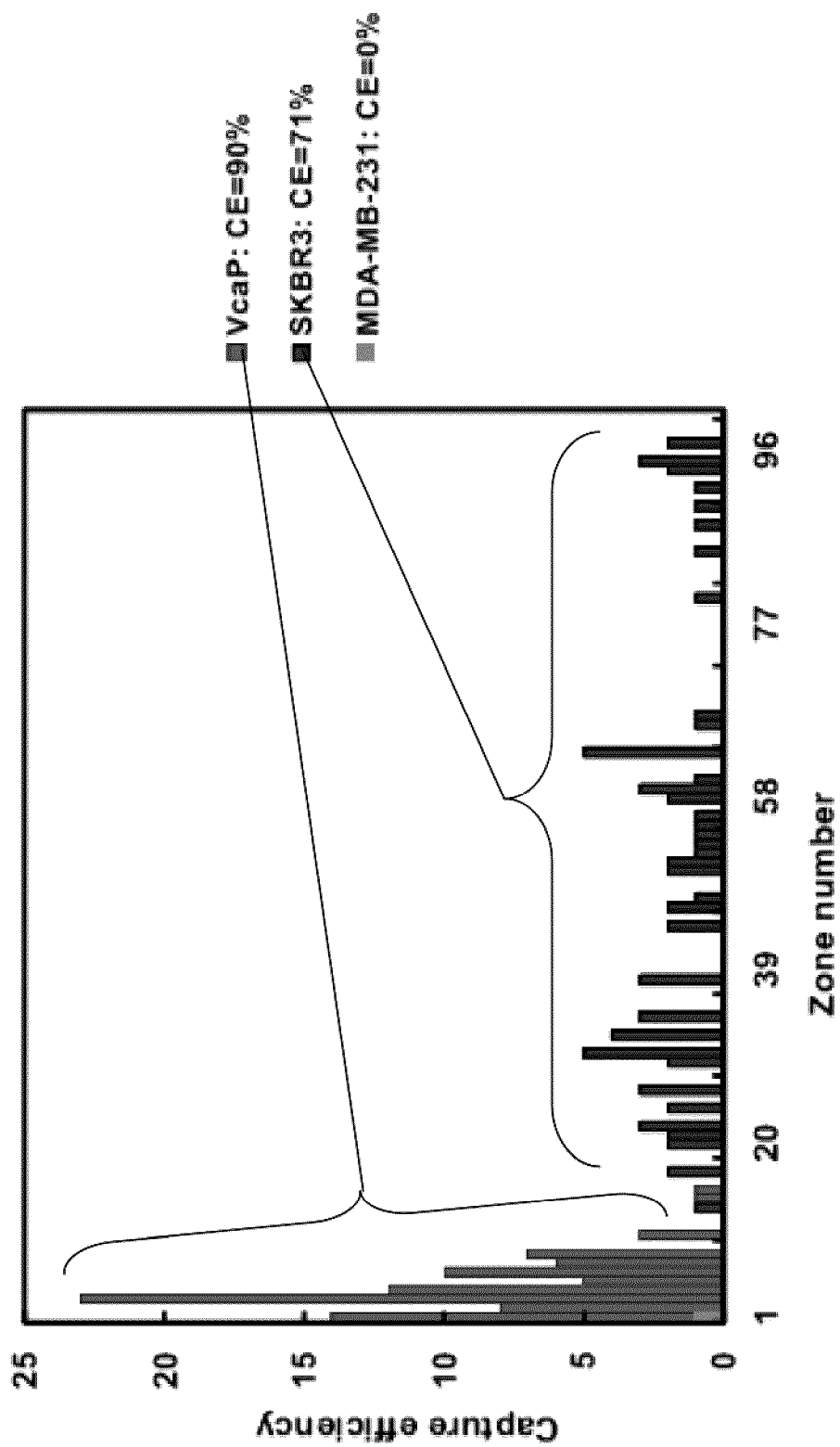
FIG. 11 is a chart showing the results of example control experiments.

FIG. 10 shows charts illustrating the reproducibility of using the example magnetic profiling device, verified using model cell lines. Three runs using the same cell line produced a similar pattern of capture in the example magnetic profiling device. In each trial, buffer solution were spiked with hundreds of VCaP cells (A), SKBR3 cells (B), and MDA-MB-231 cells. For comparison control experiments were carried out using a microfluidic chip lacking nickel micro-magnets. Results of capture experiments without micro-magnets, examples of which are shown in FIG. 11, illustrate that VCaP cells that have highest level of magnetic loading were captured at initial zones regardless of using micro-magnets. However, SKBR3 (medium magnetic loading) cells were distributed randomly along the control device and capture efficiency of MAD-MB-231 cells that have lowest level of EpCAM expression was zero without incorporating micro-magnets. Thus, the control device was found to yield little useful profiling information, highlighting the role of the micro-magnets.

The magnetic ranking cytometry approach may be amenable to the use of any surface antigen for profiling. The SKBR3 cell line was profiled using three different surface markers that are often over-expressed in epithelial cancer cells: human epidermal growth factor receptor 2 (HER2)/neu, EpCAM, and N-Cadherin.

Figure 2C:
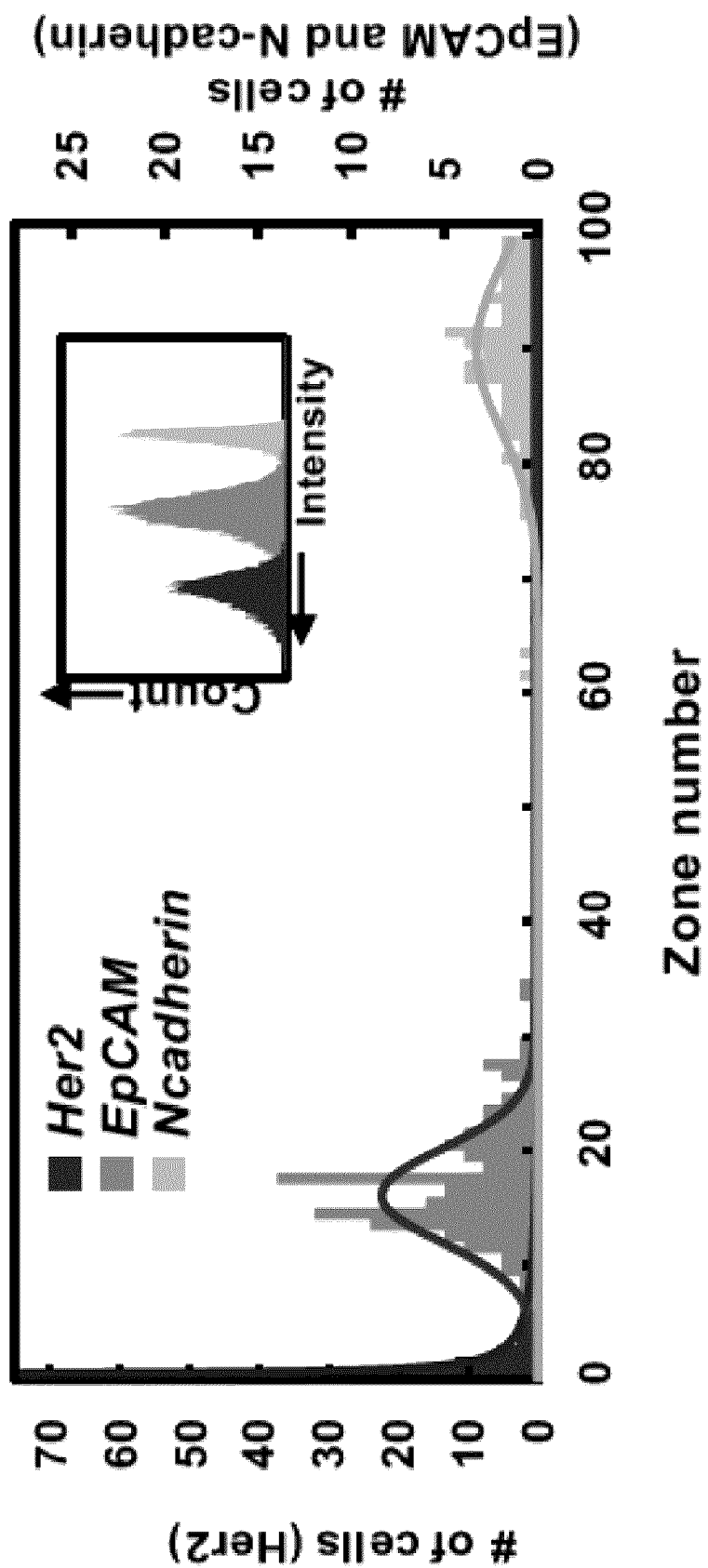
FIG. 2C is a chart illustrating resulting distribution of a breast cancer cell line magnetically profiled for different cancer biomarkers.

Example results are illustrated in FIG. 2C. The inset in FIG. 2C shows the level of these three surface markers in example SKBR3 cells measured by conventional flow cytometry. As HER2 is over-expressed in this cell line, experiments with magnetic nanoparticles coated with anti-HER2 was found to result in cells being captured in the earlier capture zones. However, capture with anti-N-Cadherin coated nanoparticles showed most cells being captured in the later capture zones of the device. EpCAM levels are intermediate on these cells as reflected in the profile obtained using the device.

Figure 2D:
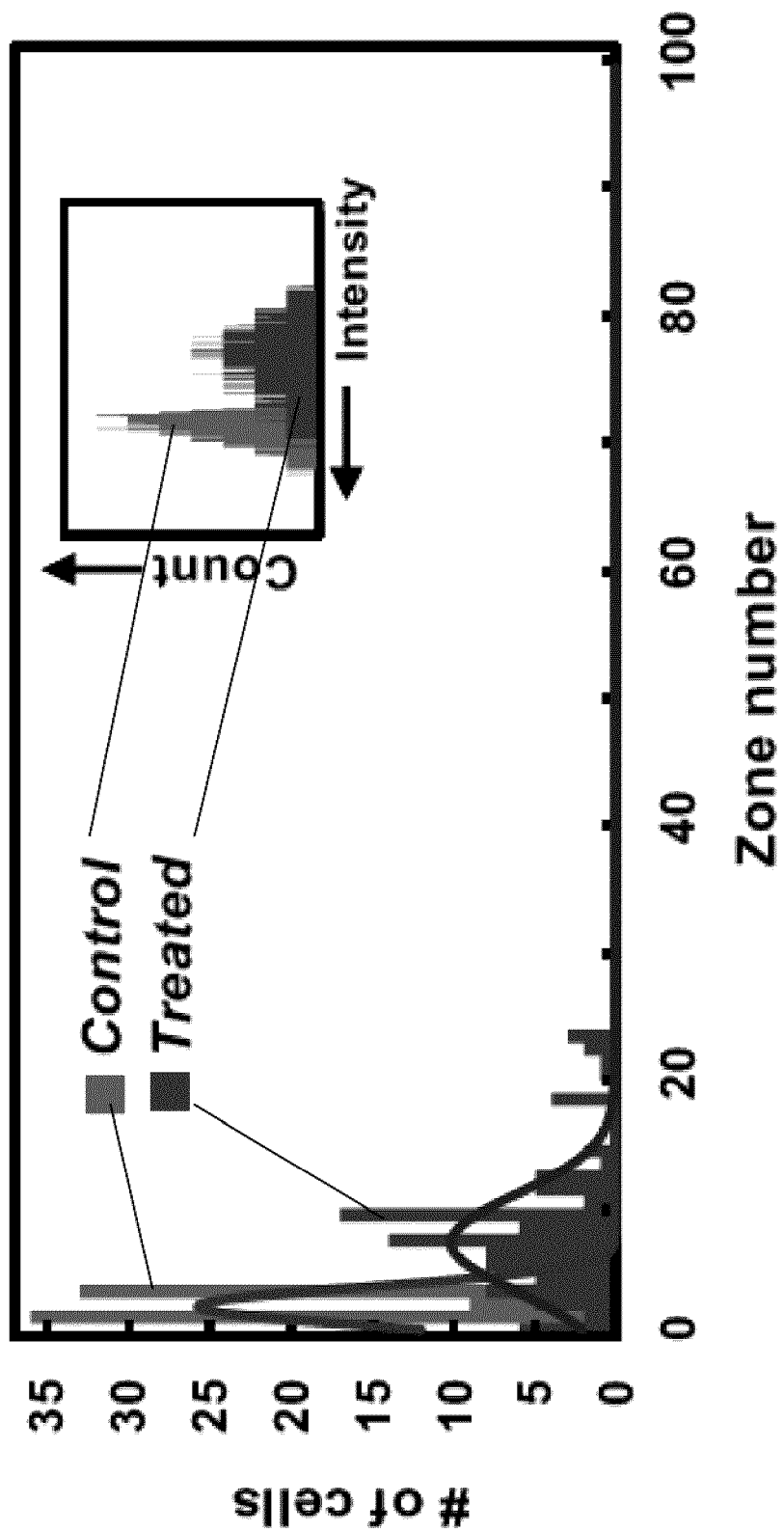
FIG. 2D is a chart illustrating analysis of cells representing an example in vitro EMT model.

Magnetic ranking cytometry using the disclosed device was also investigated for using in monitoring dynamic phenotypes in cancer cells, and in particular changes induced by EMT. Using an in vitro model for EMT—$CoCl_2$ induced hypoxia (26)—SKBR3 cells that were untreated versus those where EMT had been induced were studied. After 72 hours of $CoCl_2$ treatment, the example device was used to assess control and treated samples using EpCAM as a profiling marker. Example results are shown in FIG. 2D. The shift observed for treated cells sorted in the example device also confirms EpCAM down regulation. The inset in FIG. 2D shows the down regulation of EpCAM in treated samples detected by conventional flow cytometry.

Figure 2E:
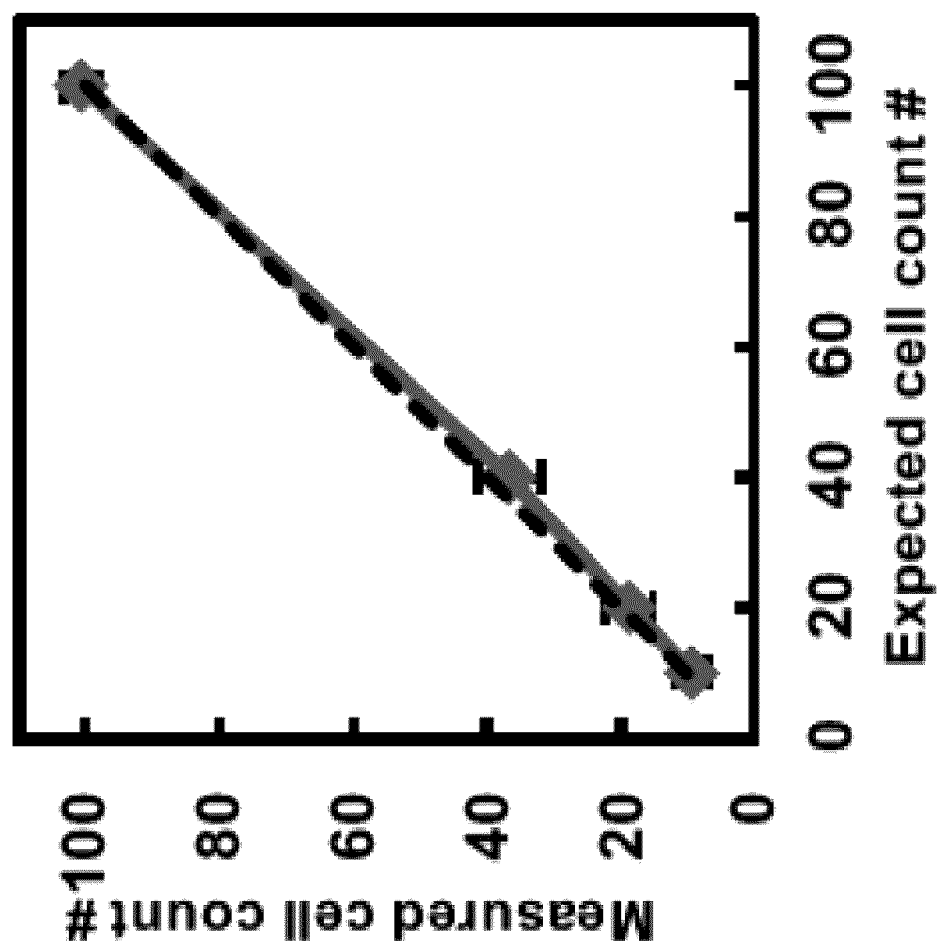
FIG. 2E is a chart illustrating the sensitivity of an example application of magnetic profiling.

The data presented in these example studies indicate that magnetic ranking cytometry using the disclosed device can produce profiles that are comparable to those reported by flow cytometry (FCM). FCM is a powerful and robust approach that is very useful in analyzing protein expression and heterogeneity in living cells. It is limited in its sensitivity, however, and requires cell numbers of $10^4$ or higher for accurate results (27). FIG. 2E shows the results of testing the example device by spiking different numbers of SKBR3 cells in buffer solution and counting them using immunofluorescence after capture in the example device. A low number of cells (n=10) spiked into a volume of 100 μl can be visualized. Error bars show standard deviations, n=3. As shown in FIG. 2E, the example disclosed device and method offers much higher sensitivity and a high level of linearity when challenged with 10-100 SKBR3 cells in buffered solutions.

Figure 3A:
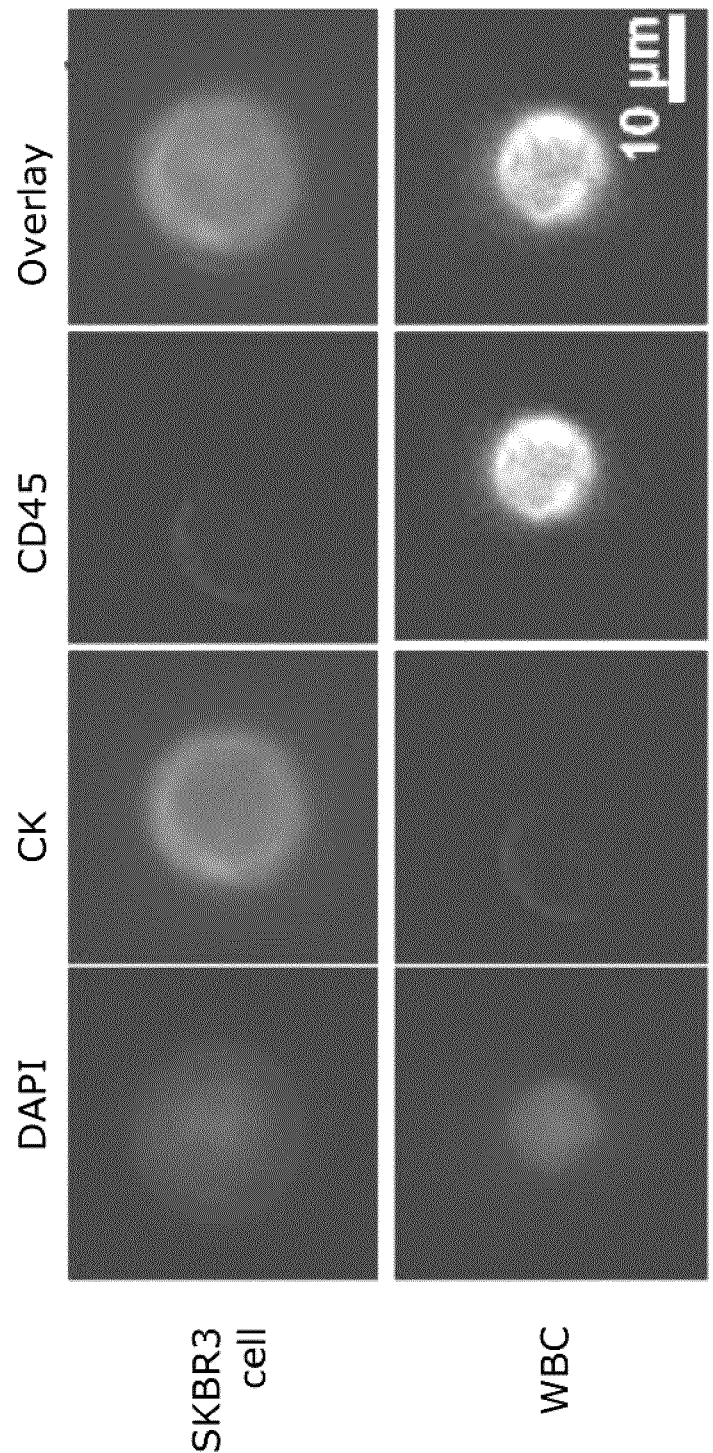
FIG. 3A shows images of immunostaining of an example captured cancer cell (top) and an example non-specifically captured white blood cell (bottom)
Figure 3B:
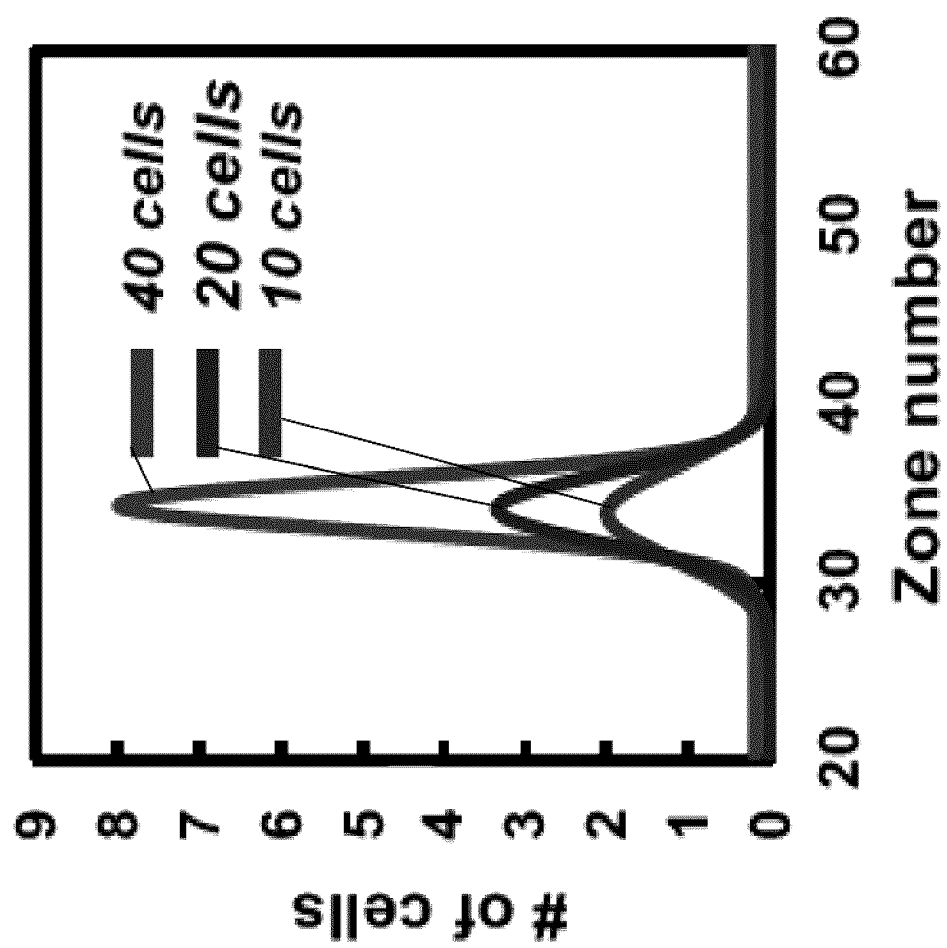
FIG. 3B is a chart illustrating magnetic profiling of example spiked samples.

When challenged with unprocessed whole blood samples, the example device was found to retain its sensitivity and profiling capability. When whole blood samples (1 ml) containing between 10 and 40 cells were profiled using EpCAM as a target marker, highly reproducible profiles were obtained independent of the number of cells present in the sample (see FIG. 3B). FIG. 3A shows example images from specific immunostaining of cancer cells. After capture, cancer cells were stained for DAPI, CK, and CD45. SKBR3 cells were identified as DAPI$^+$/CK$^+$/CD45$^-$ and white blood cells were identified as DAPI$^+$/CK$^-$/CD45$^+$.

Figure 3C:
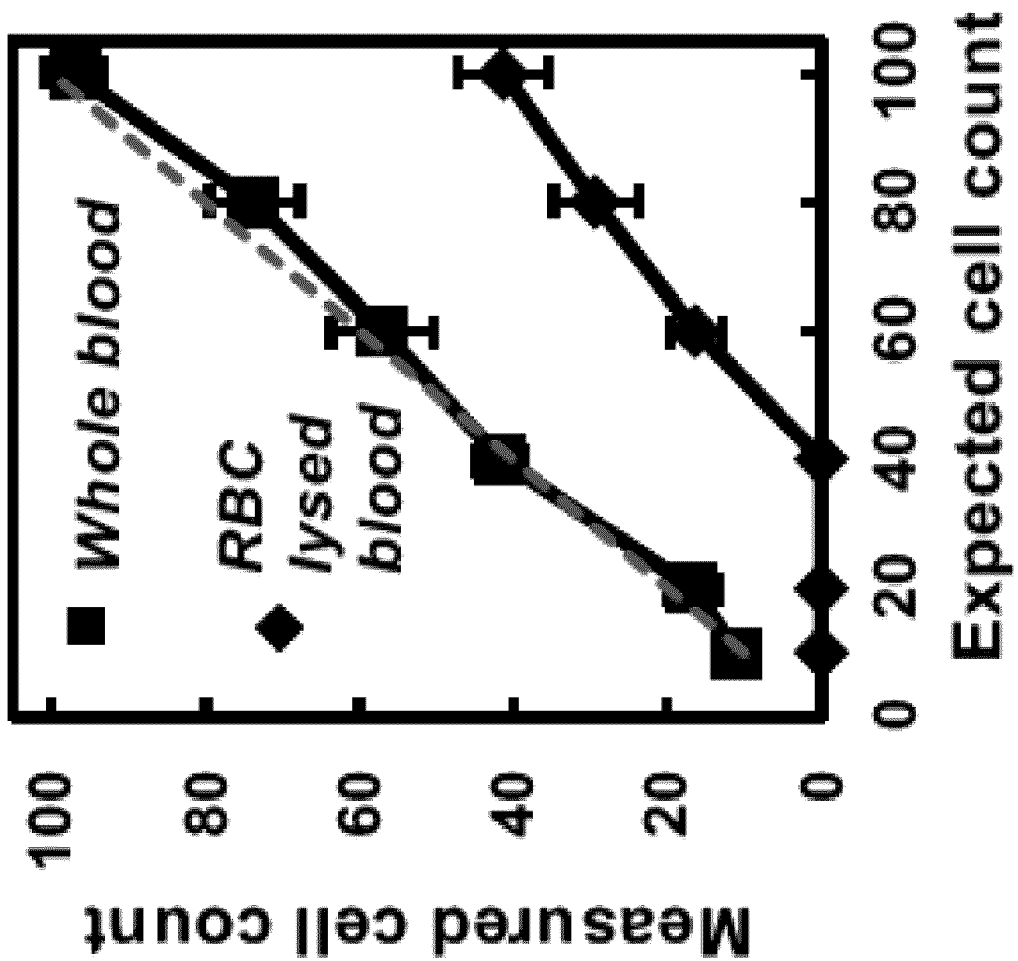
FIG. 3C is a chart illustrating an example use of magnetic profiling to count rare cells in whole blood samples and RBC-lysed samples.
Figure 3D:
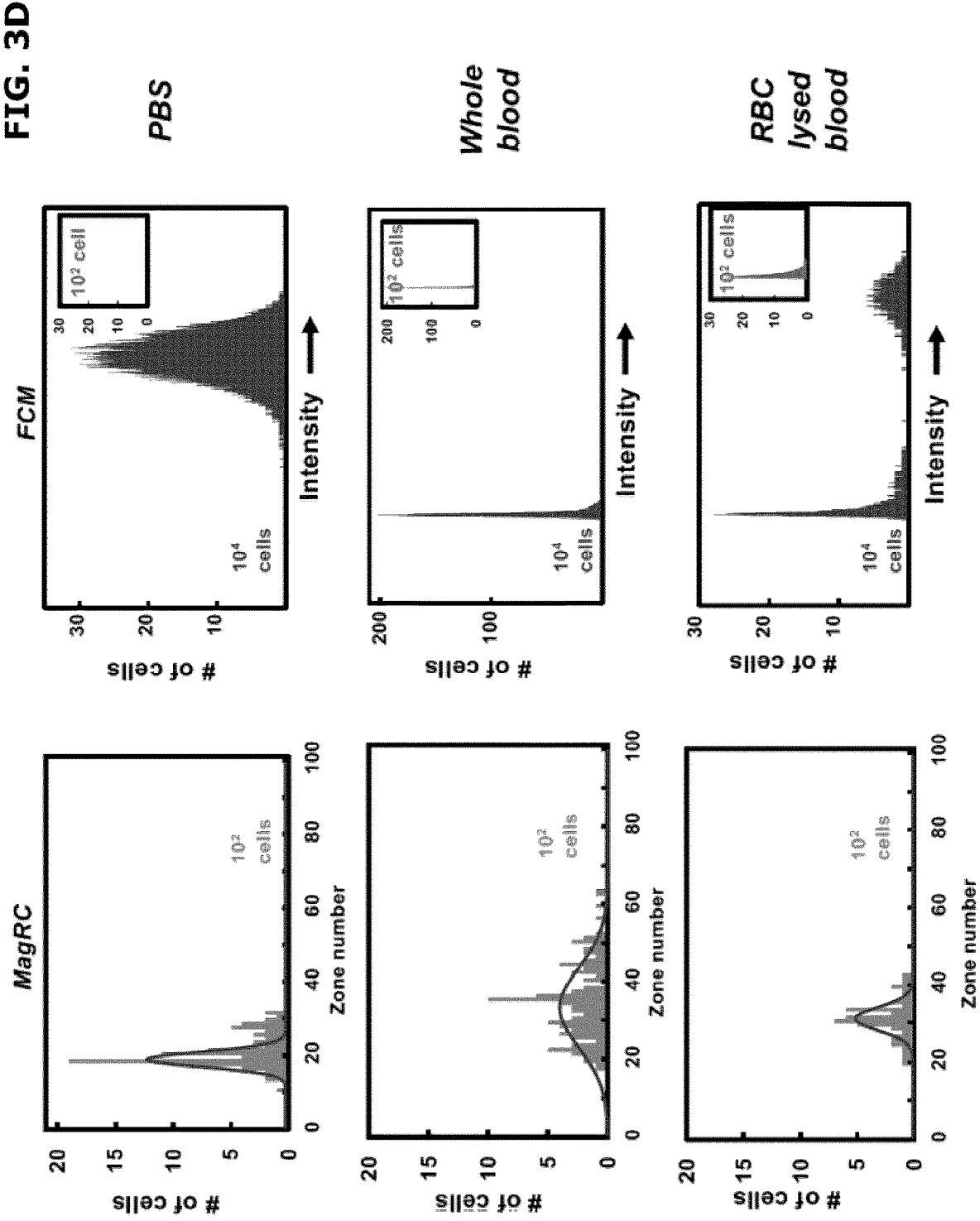
FIG. 3D shows charts illustrating example use of magnetic profiling for monitoring cells in buffered solution, whole blood and RBC-lysed blood samples, compared to flow cytometry.
Figure 12:
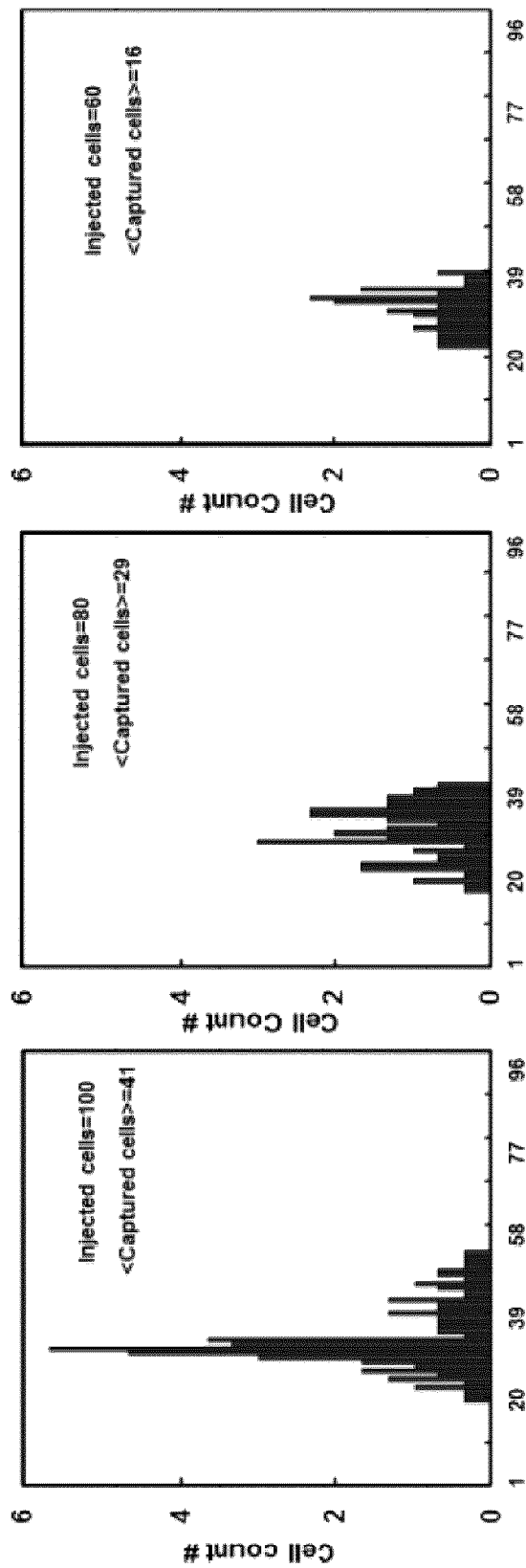
FIG. 12 shows charts demonstrating example results of profiling of SKBR3 cells in RBC-lysed blood in an example use of magnetic profiling.

Head-to-head studies of blood samples containing 100 cancer cells were performed where both MagRC (using the example device) and FCM were used for profiling. MagRC was found to be able to profile cells in the presence of normal blood cells. FIG. 3C illustrates example results using MagRC to count rare cells in unprocessed whole blood samples and RBC-lysed samples. Data collected with conventional FCM is shown for comparison. The charts of FIG. 3D show example results using flow cytometry and MagRC to monitor cells in PBS, whole blood, and RBC-lysed blood. The results demonstrate that MagRC was able to accurately profile cells in all three solutions. However, the background signal for whole blood samples overwhelmed the signals collected via FCM; only cells in PBS and RBC-lysed blood samples were accurately measured using the technique. Due to the inability of FCM to accurately count low (~100) numbers of spiked cells (inset), samples with a higher level of SKBR3 cells ($10^4$) were measured and counted using FCM. Even in the presence of 10,000 cells spiked into blood, a specific signal was not obtained with FCM. Only after the blood was treated to lyse red blood cells could spiked cancer cells be visualized. After spiking blood with different numbers of SKBR3 cells, RBC lysis buffer was used to lyse RBCs. It was followed by several washing steps. This processing step eliminates over 50% of the cancer cells (e.g., during washing steps) as assessed using MagRC (see FIG. 12, showing example results of MagRC of SKBR3 cells in RBC-lysed blood) and therefore may introduce false negatives, since the numbers of captured cells were less than numbers of loaded cells.

The MagRC approach (e.g., using the disclosed device), however, was found to be able to return accurate profiling results even with very low levels of cancer cells in unprocessed blood, a requirement for the evaluation of CTCs. It is noteworthy that the exact shape of the profile returned with MagRC was found to be affected by the presence of blood cells (see FIG. 3D), but since it is consistently affected by the increased drag acting on the tumor cells that arises from interactions with the blood cells, it gives reproducible data for a given type of sample (e.g. whole blood).

To evaluate the utility of magnetic ranking cytometry (e.g., using the disclosed device) for the analysis of CTCs and their dynamic properties, blood from mice bearing xenografted tumors was analyzed as a function of tumor growth. To generate the model, MCF-7/Luc human breast cancer cells were implanted into the mammary fat pad of immunodeficient mice. In order to boost tumor growth in a subset of animals, one group of mice received an estrogen pellet prior to tumor implantation (E$^+$), as estrogen stimulates MCF-7 tumor growth. The other set of mice were not treated with estrogen prior to tumor implantation. After tumor cell injection, blood was collected from each mouse every 10 days and analyzed using MagRC. Immunostaining that was specific for the implanted human cancer cells was used to establish the MagRC profile, and tumor growth was visualized by imaging the bioluminescence generated by the luciferin-tagged MCF-7 cells.

Figure 4A:
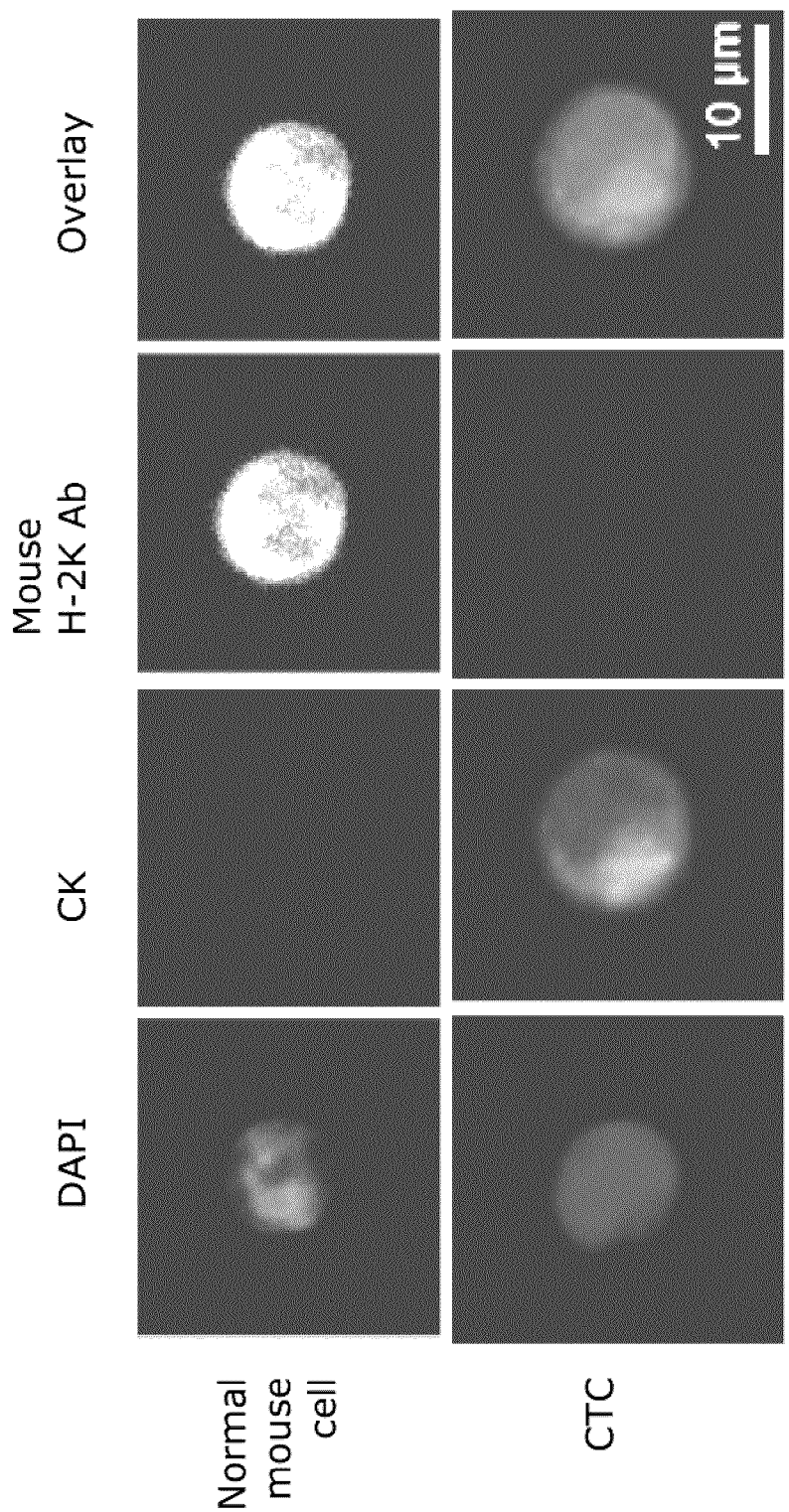
FIG. 4A shows images of an example captured CTC compared to an example normal mouse cell.
Figure 4B:
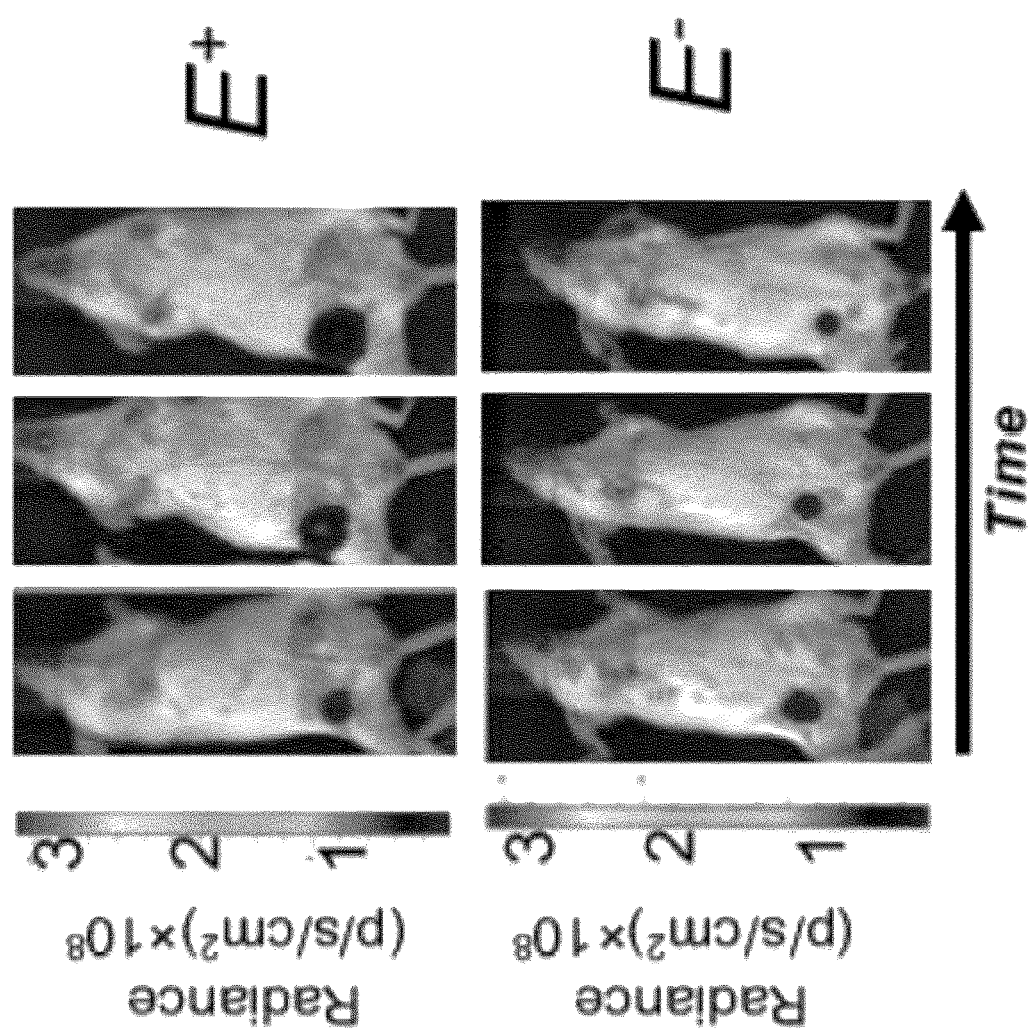
FIG. 4B shows bioluminescence images of example mice implanted with tumors, in estrogen positive and estrogen negative groups.

FIG. 4A shows representative images of a captured CTC and a normal mouse cell. Nuclei are stained with DAPI (blue), CTCs are stained for CK (red), and mouse cells for mouse H-2k (green). FIG. 4B show bioluminescence images of mice implanted with MCF-7 tumors in estrogen positive (E$^+$) and estrogen negative (E$^-$) groups during the course of tumor progression.

Figure 13A:
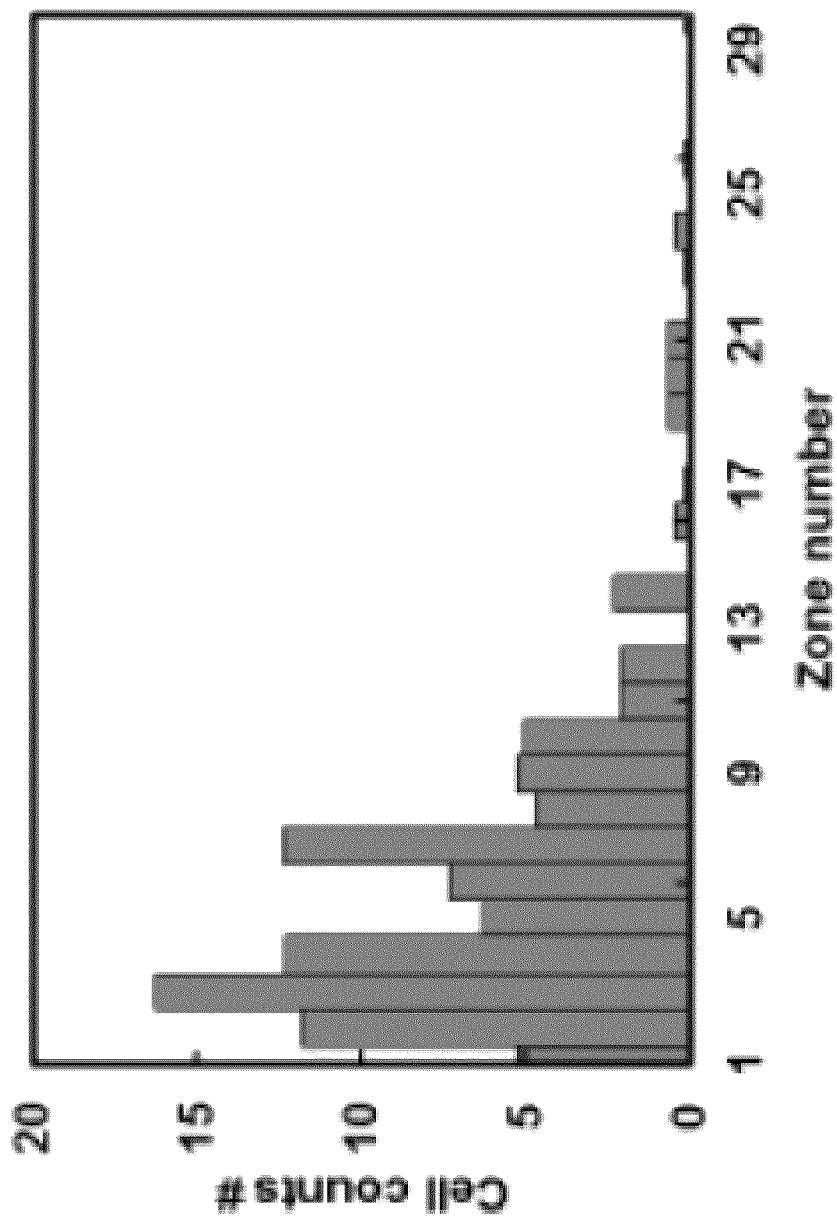
FIGS. 13A and 13B are charts showing example results of profiling of MCF-7 cells in buffer and whole blood samples, respectively.
Figure 13B:
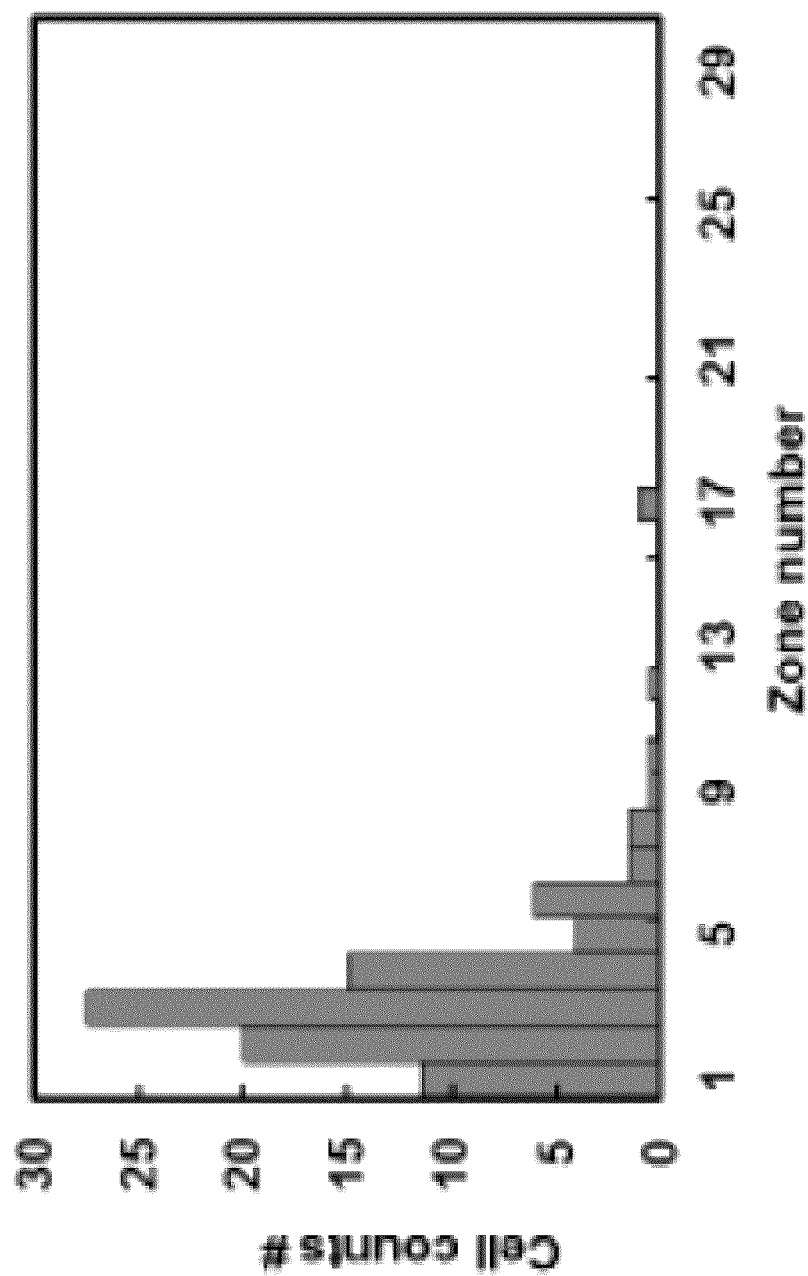

As tumor growth progressed in the xenografted animals, a marked change was visualized in the CTCs detected. In both the estrogen positive and negative animal groups, CTC levels rose as the study progressed. In the estrogen positive group, as expected, the CTCs levels increased to a much higher level than in the estrogen negative group. However, in addition to increasing in number, a marked phenotypic shift could be visualized in the more aggressive cancer model. The CTCs profiled in these mice shifted to later zones within the example device relative to early CTCs and cultured MCF-7 cells (see FIG. 13A for results in PBS and FIG. 13B for results in whole blood), indicating that their phenotypes were changing and EpCAM levels were decreasing. The profiles of the CTCs from the estrogen negative mice remained static.

Figure 4C:
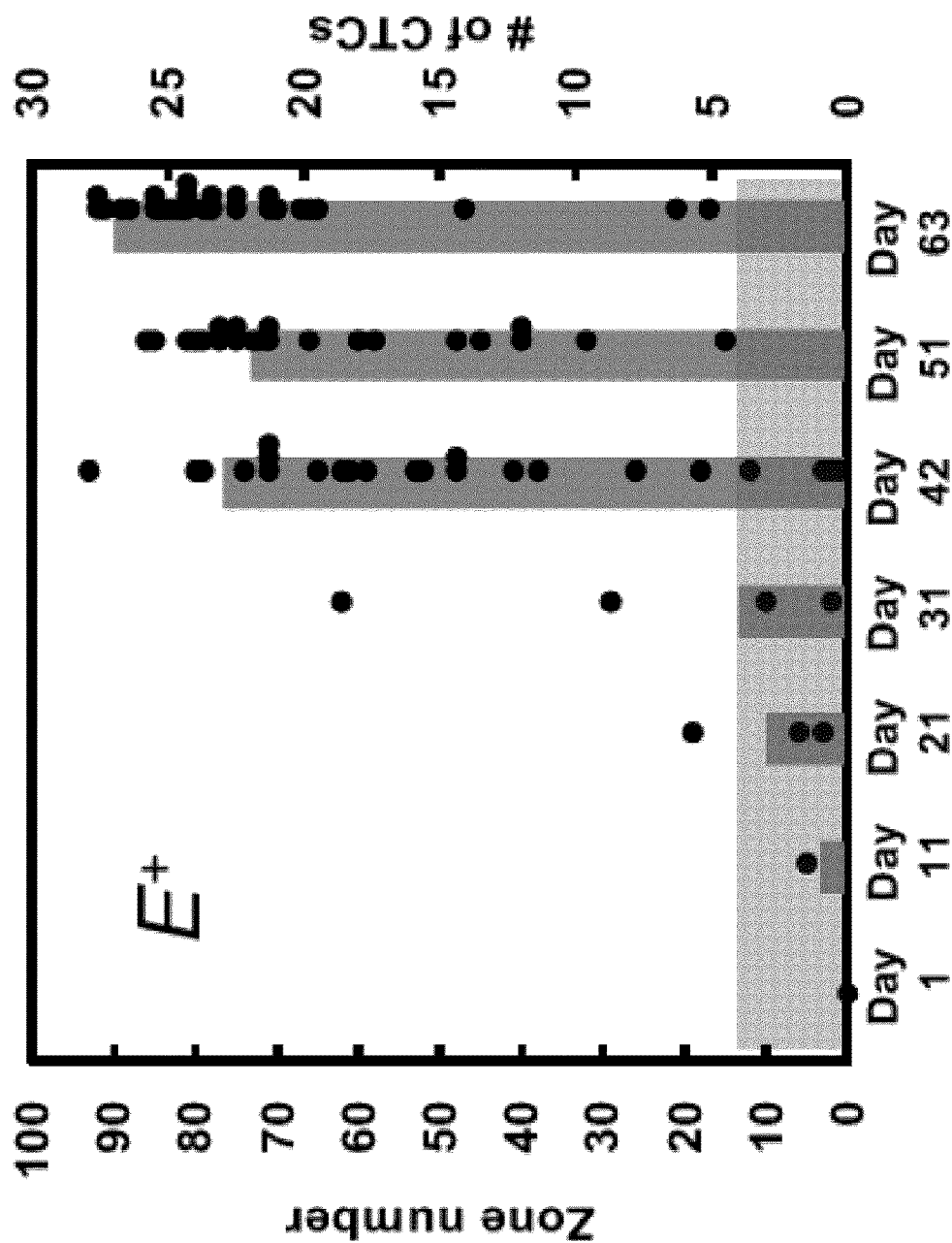
FIGS. 4C and 4D are charts showing example distribution profiles of CTCs found in mice implanted with tumors, in estrogen positive and estrogen negative groups, respectively.
Figure 4D:
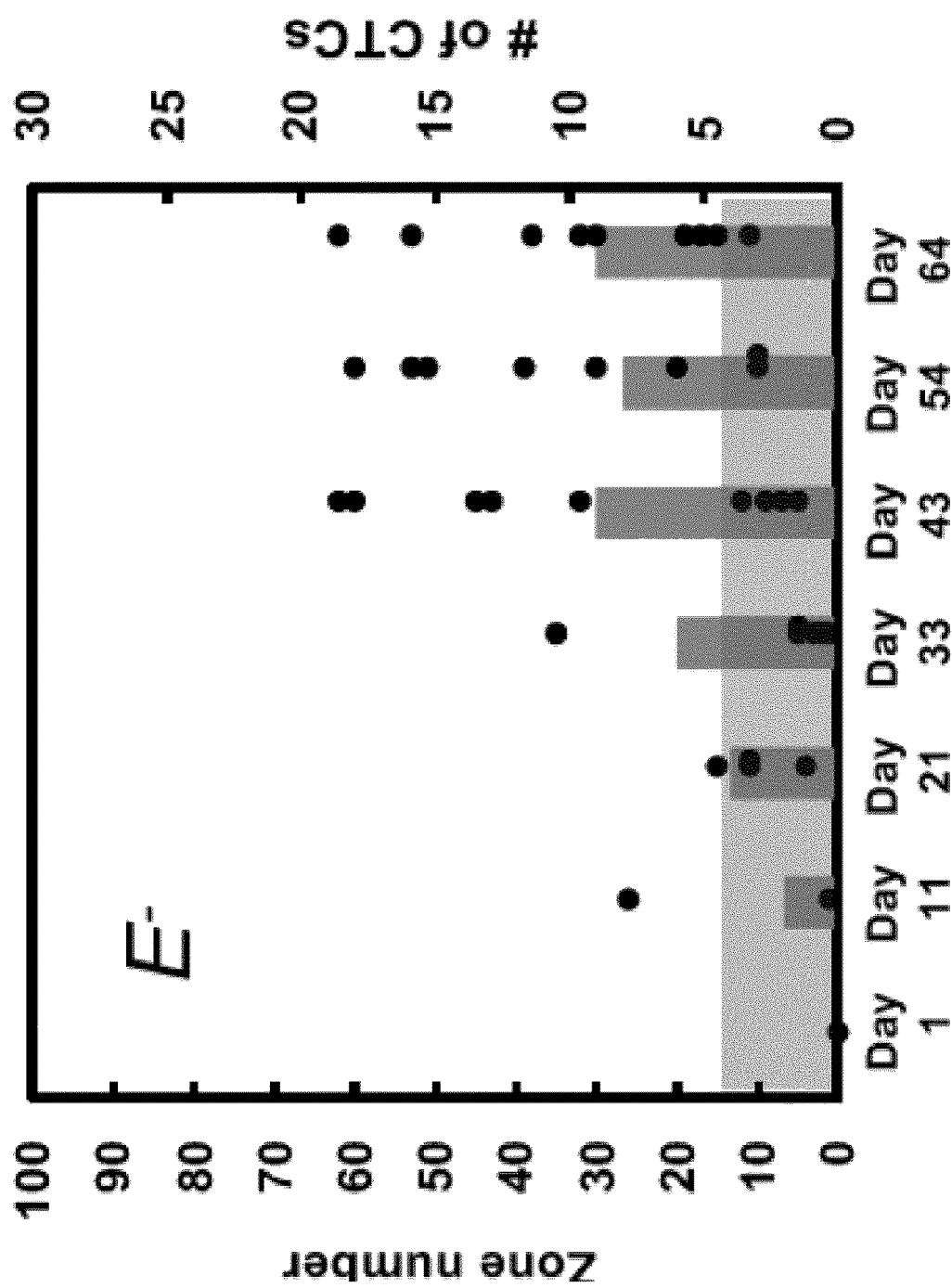
Figure 4E:
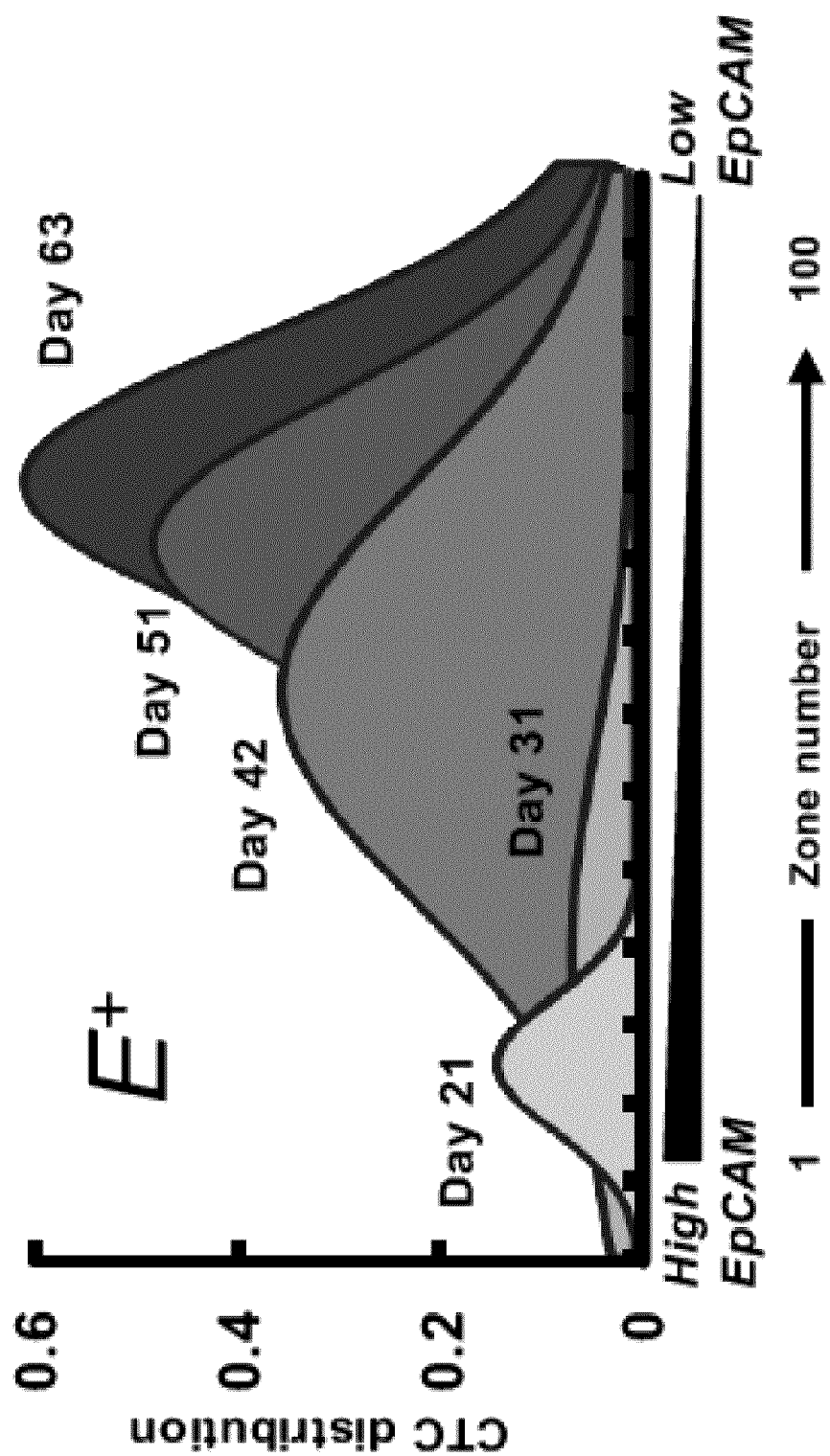
FIGS. 4E and 4F are charts illustrating scaled normal distribution profiles of CTCs extracted at various time points from mice implanted with tumors, in estrogen positive and estrogen negative groups, respectively.
Figure 4F:
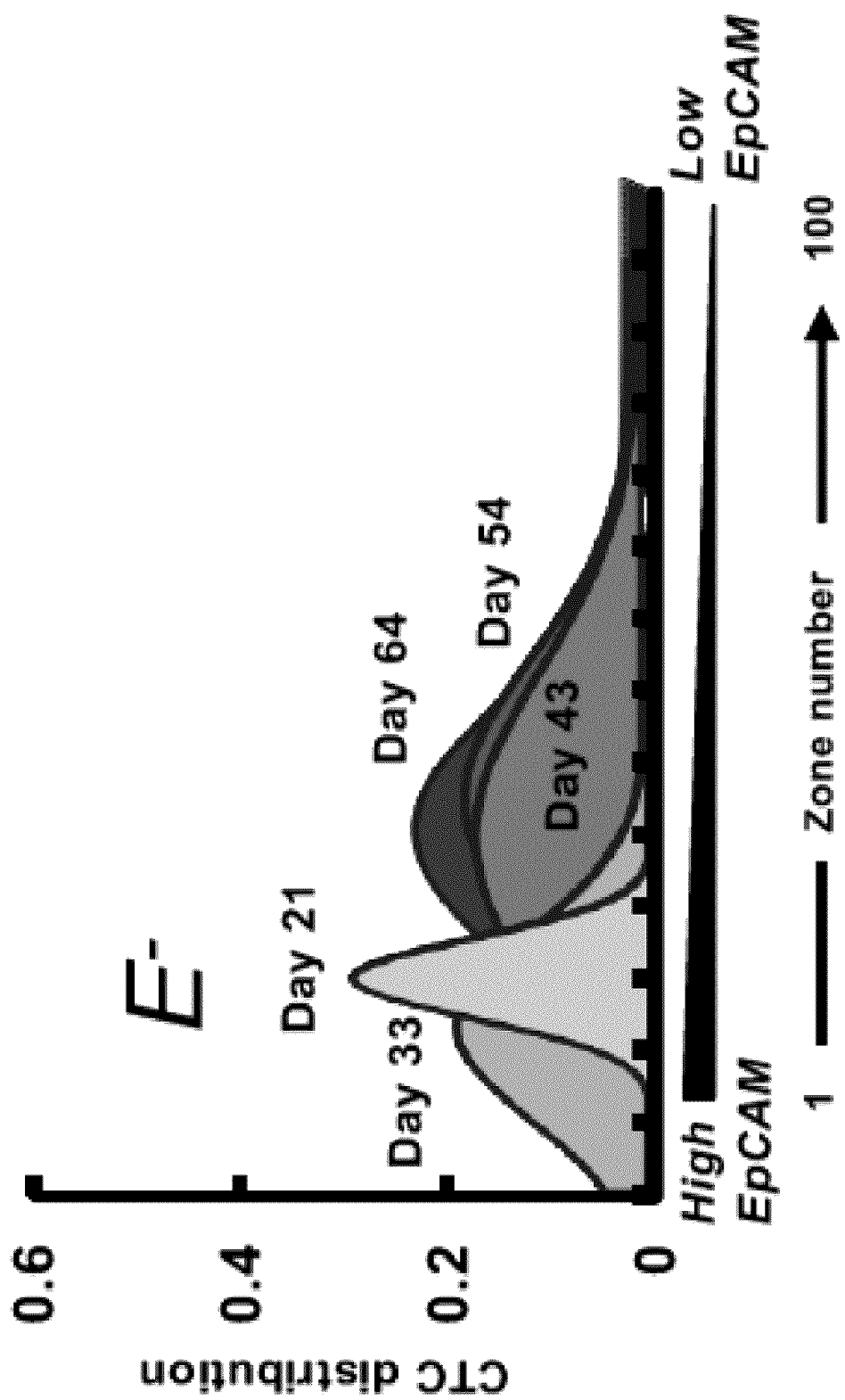
Figure 14A:
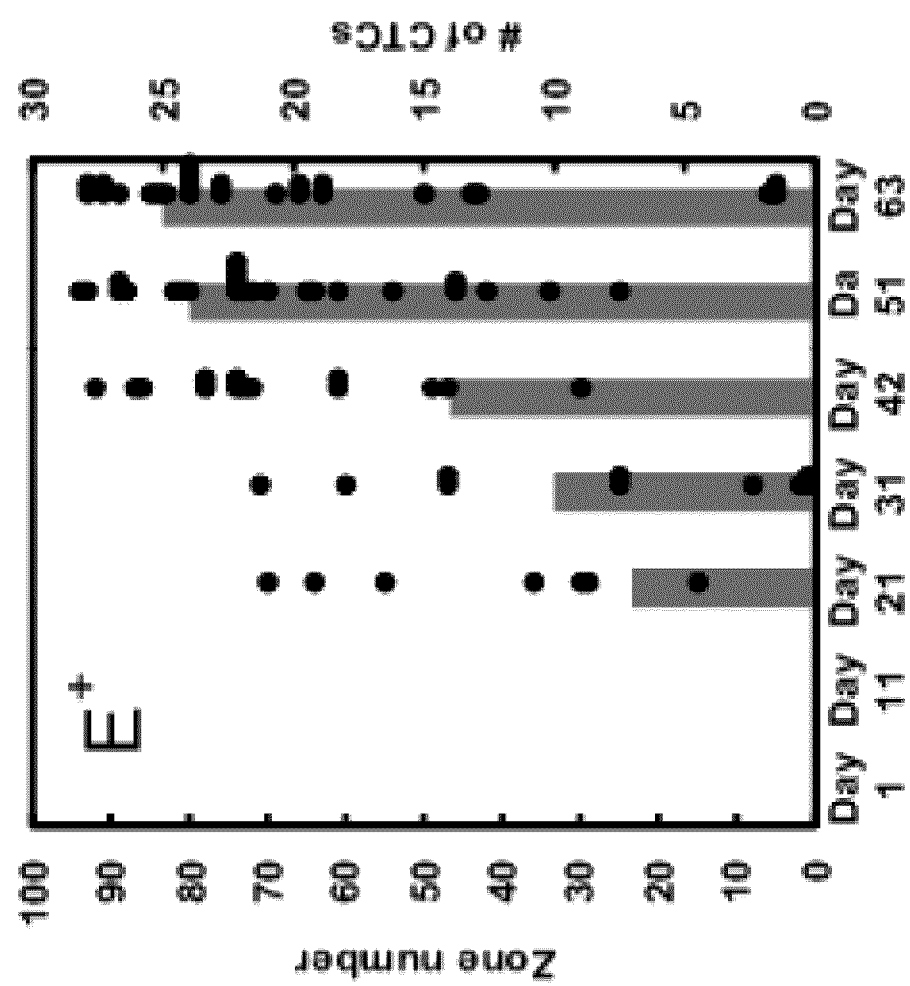
FIGS. 14A and 14B are charts showing example CTC distribution profiles obtained in example uses of magnetic profiling.
Figure 14B:
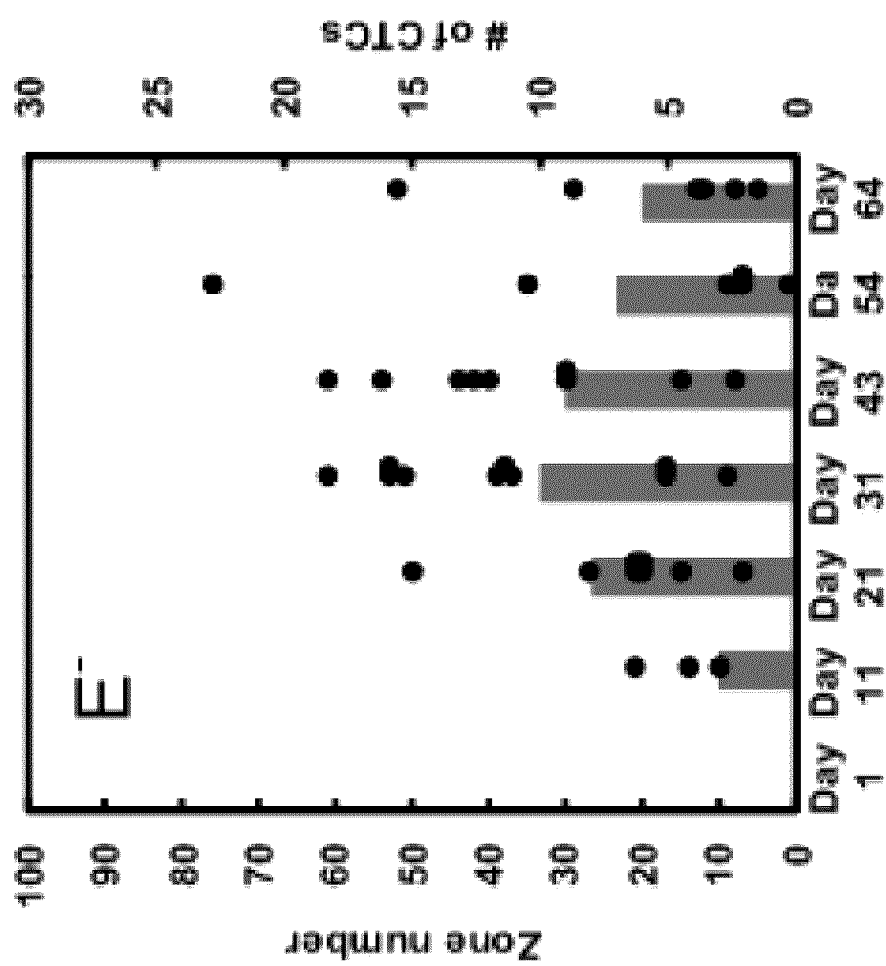
Figure 14C:
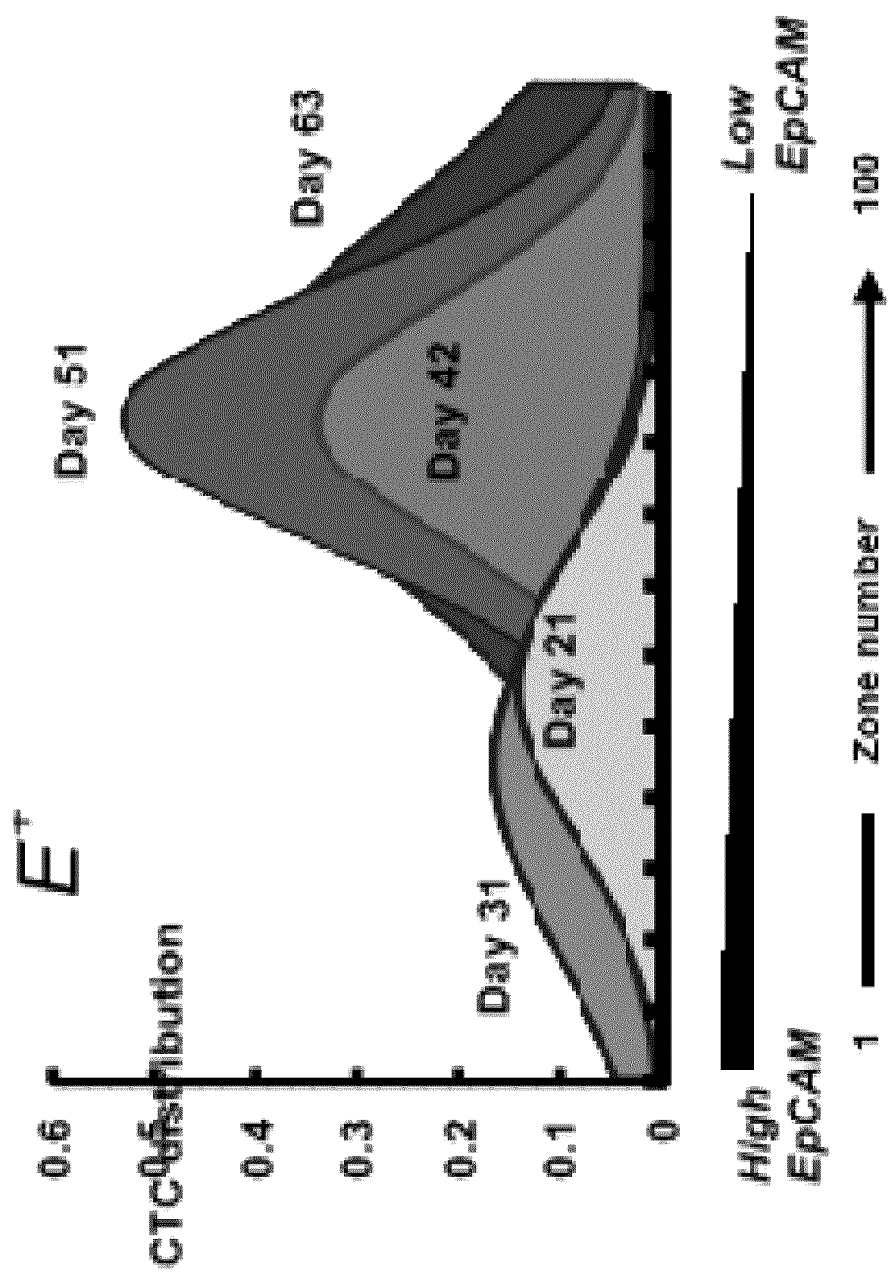
FIGS. 14C and 14D are charts showing example distribution profiles of CTCs at different time points, in example uses of magnetic profiling.
Figure 14D:
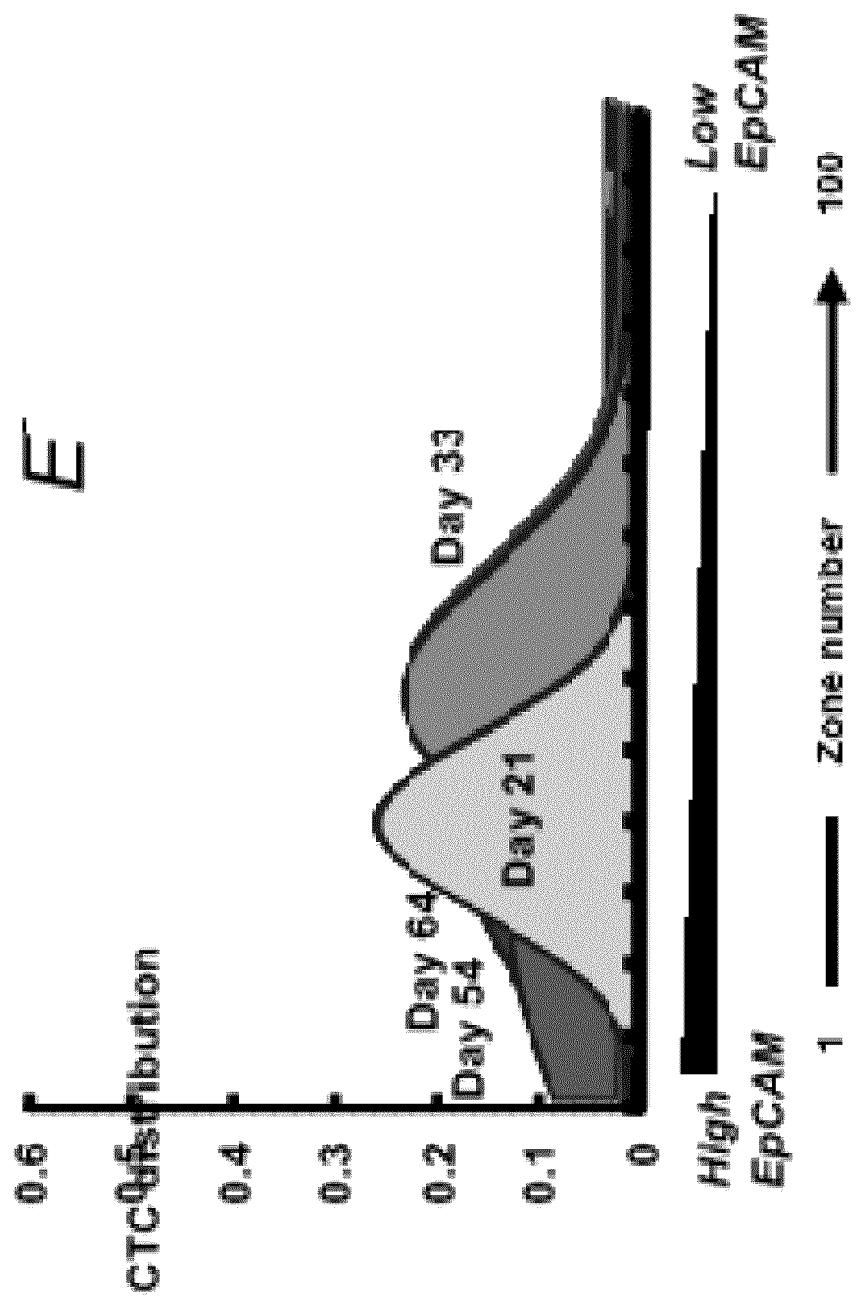

FIGS. 4C and 4D show example CTC distribution profiles of mice in E$^+$ and E groups. Bar graphs show the total number of CTCs found in each day. Each black circle denotes one CTC. The red zone represents the distribution area for cultured MCF-7 cells (See FIGS. 13A and 13B). FIGS. 4E and 4F show example scaled normal distribution profiles of CTCs extracted at each time point, centered at the median CTC zonal position. CTC profiles in the E$^+$ model show a shift toward less epithelial phenotypes at the later stages of the disease (FIG. 4E), however, this shift is not observed in E$^-$ model (FIG. 4F). FIGS. 14A-14D shows additional example data collected from mice with implanted tumors. FIGS. 14A and 14B show example CTC distribution profiles of mice in invasive and non-invasive groups. Bar graphs show the total number of CTCs found in each day. Each black circle represents one CTC. FIGS. 14C and 14D show example distribution profiles of CTCs extracted for each day. Each profile is a normal distribution, centered at the median CTC zonal position. The area under each curve is scaled to reflect the relative total CTC count.

Figure 4G:
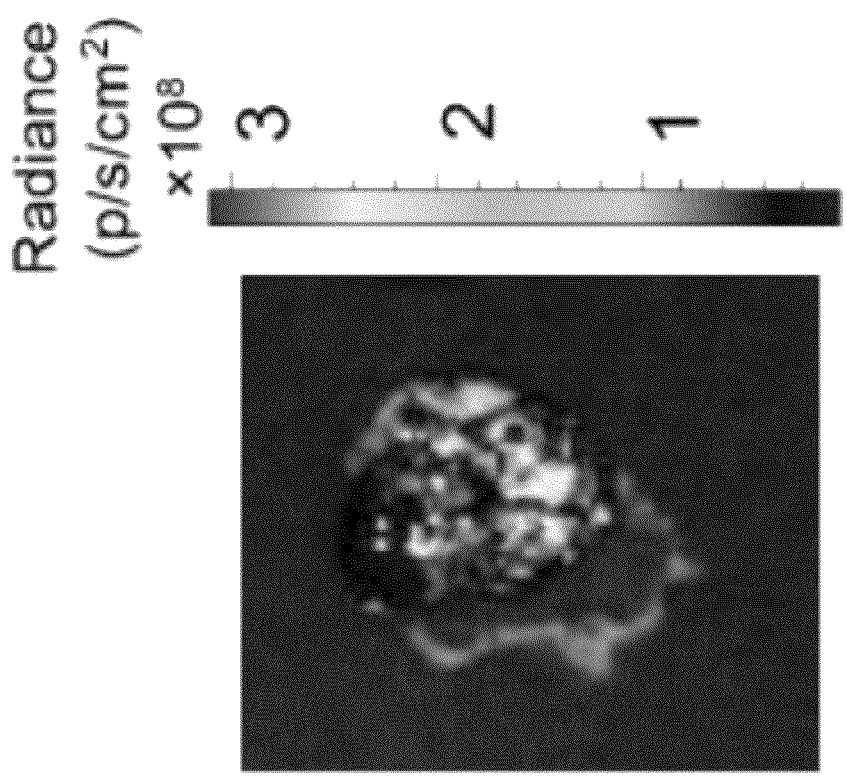
FIG. 4G is a bioluminescence image of an example lung of a mouse in the estrogen positive group, where visible luminescence indicates the presence of metastases in the lung.

To compare invasiveness of the tumors in the two groups, mouse lungs were extracted and sent for histopathology at the end of the study, and sections were scanned for micrometastases. Micrometastases were found in lungs of the E$^+$ group; however, there were no micrometastases in the E$^-$ group. The presence of the metastases along with the altered CTC profile observed by MagRC is consistent with the idea that the CTCs produced by the estrogen-positive tumor possess a more metastatic profile. FIG. 4G is an example bioluminescence image of whole lung of a mouse in the E$^+$ group. Visible luminescence indicates the presence of metastases in lung. FIG. 4H is an example histopathology image of lung section of a mouse from the E$^+$ group confirming the presence of micrometastases.

Figure 15A:
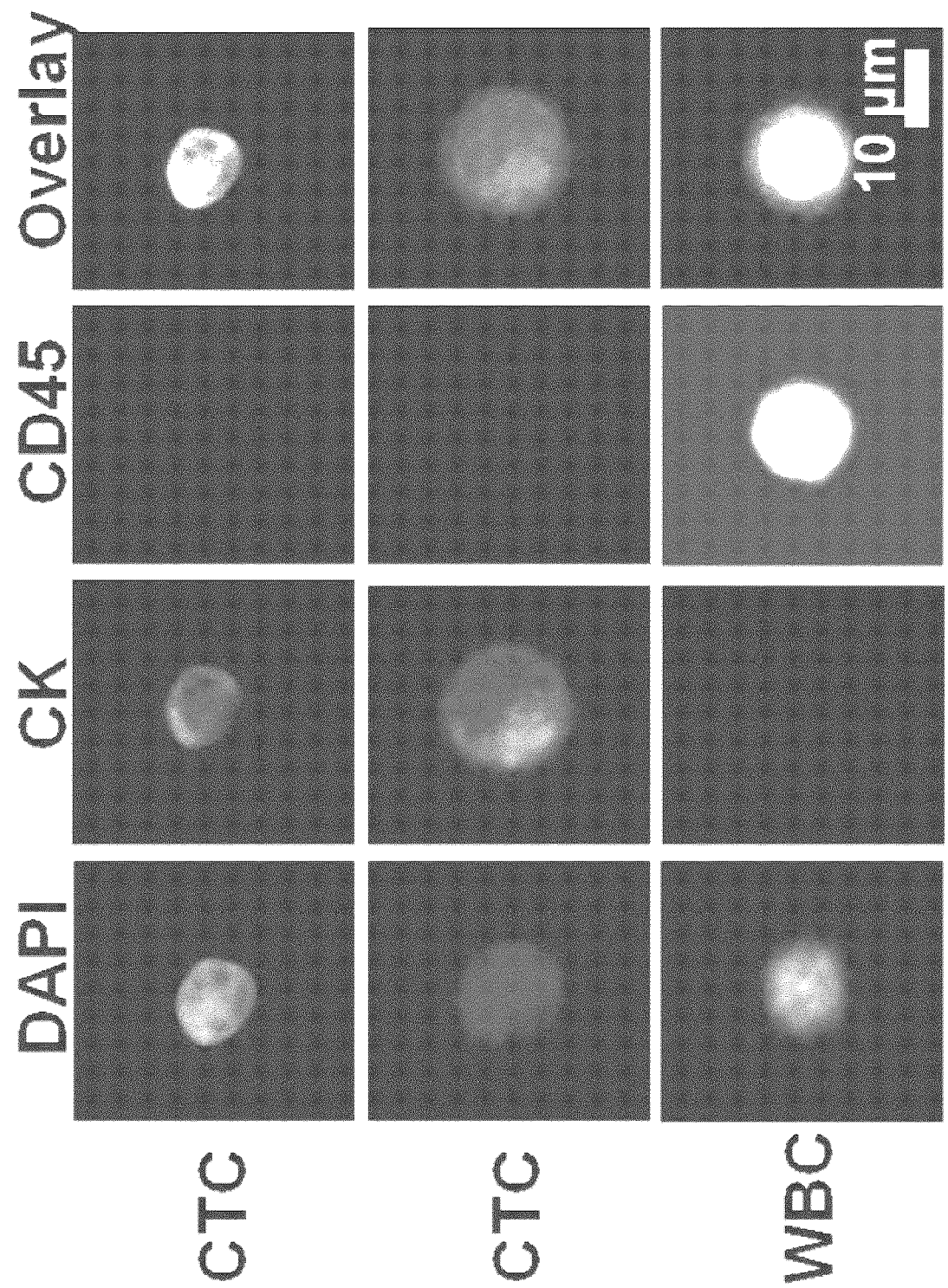
FIG. 15A shows example images of CTCs captured from prostate cancer patient samples, compared to a white blood cell.

In another example study, MagRC was used to profile CTCs in clinical samples. Samples were collected from patients exhibiting metastatic castration-resistant prostate cancer (mCRPC, n=10) and localized prostate cancer, (n=14). Immunostaining was used to distinguish between CTCs and WBCs. FIG. 15A shows example images of CTCs captured from prostate cancer patient samples compared to a white blood cell. The nuclei were stained with DAPI, CTCs were stained for CK and white blood cells were stained for CD45. The blood collected from 9 healthy donors was also analyzed. The tables below show data collected from these samples:

TABLE I

Counts of $CK^+/DAPI^+/CD45^-$ cells in blood collected from healthy donors. These cells are randomly scattered within the fluidic device.

| Healthy donor | Count |
|---|---|
| HD1 | 2 |
| HD2 | 0 |
| HD3 | 3 |
| HD4 | 1 |
| HD5 | 2 |
| HD6 | 0 |
| HD7 | 0 |
| HD8 | 6 |
| HD9 | 5 |

TABLE II

CTC counts and clinical data for patients with localized prostate cancer

| Patient number | Age | Gleason Score | PSA | CTC count by MagRC/ml |
|---|---|---|---|---|
| L-P1 | 66 | G6 | 1.5 | 27 |
| L-P2 | 70 | G6 | 14 | 36 |
| L-P3 | 66 | G6 | 1.3 | 48 |
| L-P4 | 65 | G7 | 9.1 | 16 |
| L-P5 | 80 | G7 | 23 | 29 |
| L-P6 | 68 | G7 | 4.1 | 31 |
| L-P7 | 50 | G7 | 2 | 39 |
| L-P8 | 66 | G7 | 6.3 | 41 |
| L-P9 | 64 | G7 | 2.2 | 51 |
| L-P10 | 65 | G8 | 4.4 | 19 |
| L-P11 | 74 | G8 | 24 | 37 |
| L-P12 | 54 | G9 | 36 | 20 |
| L-P13 | 73 | G9 | 6.2 | 45 |
| L-P14 | 64 | G9 | 1600 | 95 | score 7, and Gleason score 8 and 9. The median values for the G6 patients have a statistically-significant difference from the G8/G9 patients, with a p value of 0.03. The G7 patients have highly variable mean values. FIGS. 15F and 15G are boxplots that show the CTC profile distribution of individual patients with localized (FIG. 15F) and metastatic (FIG. 15G) prostate cancer.

The profiles collected from the different patients exhibited an interesting series of trends. Overall, the MagRC profiles for the mCRPC patients were similar to one another (see FIG. 15B). The CTCs from these patients appeared in the later (i.e., further downstream) zones of the device, consistent with the idea that these were low-EpCAM CTCs in later stages of EMT. In the case of localized prostate cancer patients, there was an appreciably greater diversity in the MagRC profiles (see FIG. 15C). The profiles were analyzed according to the Gleason score of the tumours biopsied in these patients. Three, six, and five patients with tumours with Gleason score of 6 (P1-P3), Gleason score 7 (P4-P9), and Gleason scores 8 and 9 (P10-P14) were analyzed, respectively. The zone distribution profiles for these patients were measured, and it was found that G6 patient CTCs were captured in earlier zones (median zone=40) relative to the CTCs captured from samples from patient with G8/G9 tumours (median zone=64) (see FIG. 15E). The boxplot presented in FIG. 15D also demonstrated the CTC profile distribution in patients with different types of prostate cancer tumours. These results suggest that the patients with G7 tumours exhibited variable profiles compared to the other two groups. Statistical analysis was performed on the localized prostate cancer patient CTC zone distributions, and found that G8-G9 CTCs were statistically separated from G6 CTCs. The results are shown in the table below (P<0.05, paired t-test):

TABLE III

CTC counts and clinical data for patients with metastatic castration-resistant prostate cancer

| Patient number | Age | Gleason Score (at diagnosis) | PSA (at CTC count, ug/L) | ALP (at CTC count, U/L) | LDH (at CTC count, U/L) | CTC count by MagRC/ml | CellSearch CTC count |
|---|---|---|---|---|---|---|---|
| M-P1 | 56 | 7 | 45 | 71 | 185 | 9 | 1 |
| M-P2 | 72 | 9 | 2.7 | 69 | 276 | 10 | 1 |
| M-P3 | 79 | 7 | 8.5 | 206 | 216 | 18 | 1 |
| M-P4 | 79 | 6 | 21 | 73 | 180 | 17 | 2 |
| M-P5 | 68 | 9 | 0.16 | n.d. | n.d. | 19 | 0 |
| M-P6 | 72 | 9 | 9.4 | 116 | 280 | 28 | 1 |
| M-P7 | 79 | 7 | 46 | 62 | 254 | 23 | 2 |
| M-P8 | 77 | n.a. | 27 | 74 | 222 | 35 | 0 |
| M-P9 | 76 | n.a. | 39 | 53 | 187 | 34 | 2 |
| M-P10 | 64 | 9 | 1.7 | n.d. | n.d. | 48 | 5 |

Figure 15B:
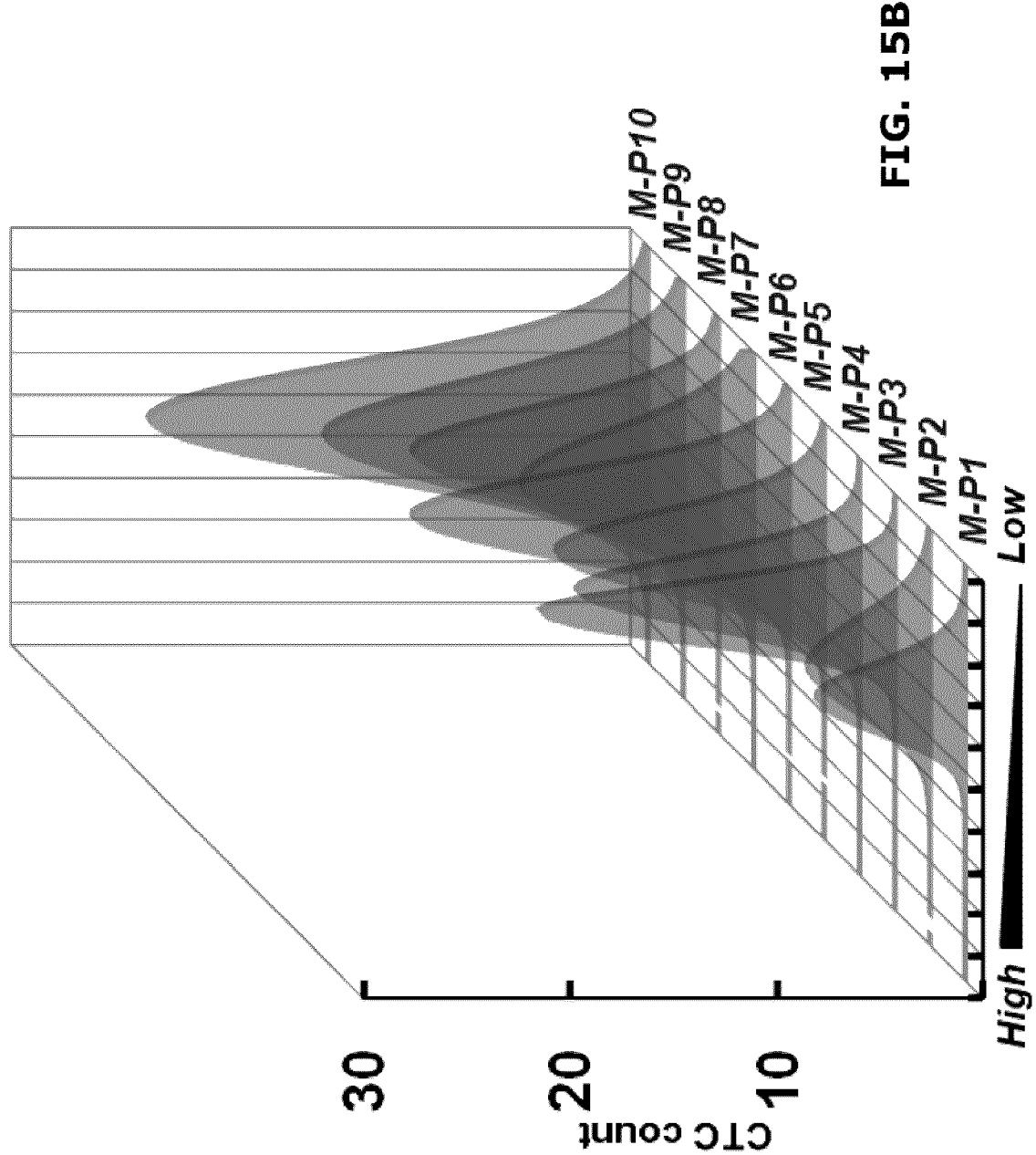
Figure 15D:
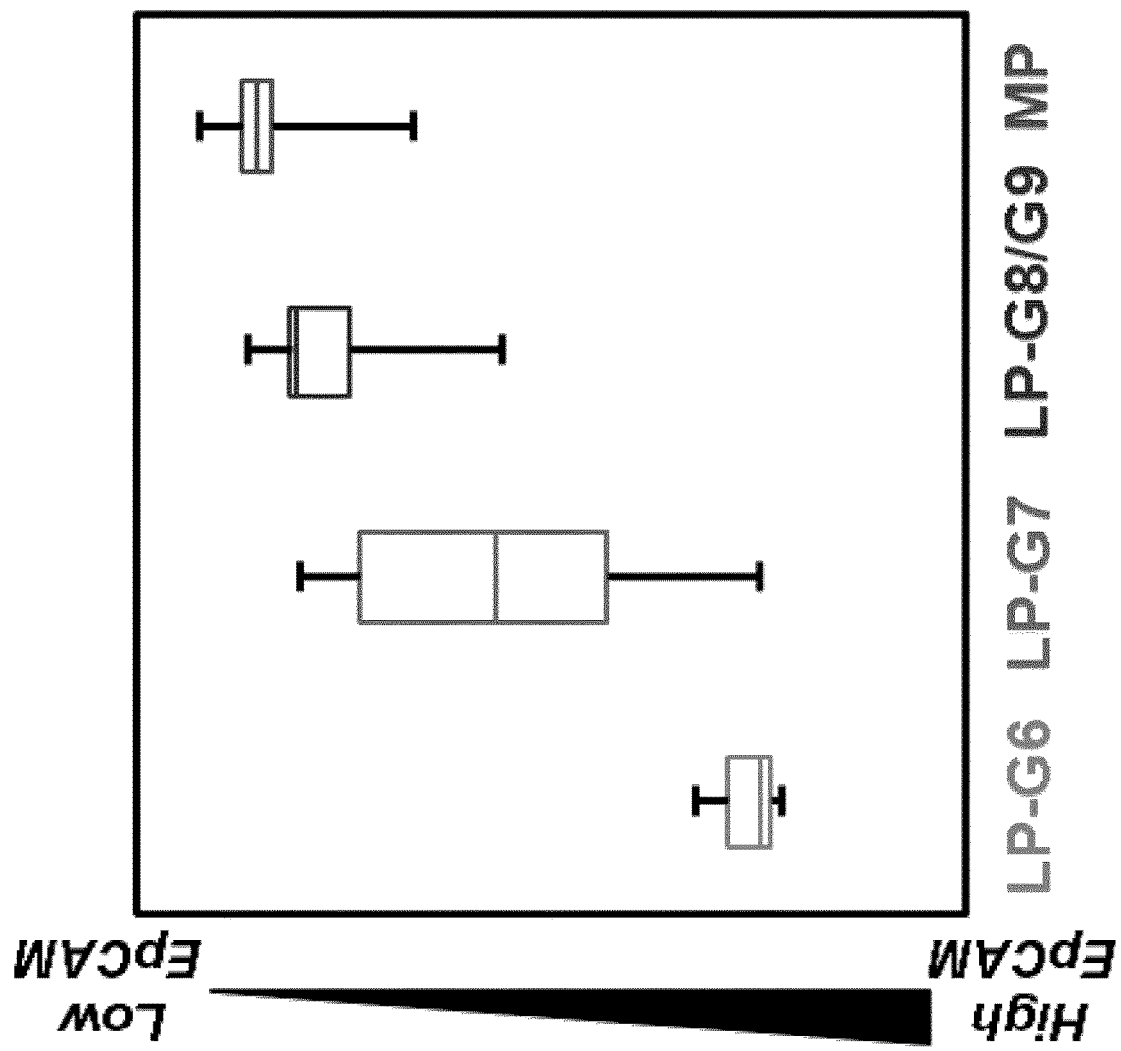
FIG. 15D is a boxplot showing CTC profile distribution in samples from patients with localized and metastatic prostate cancer.
Figure 15E:
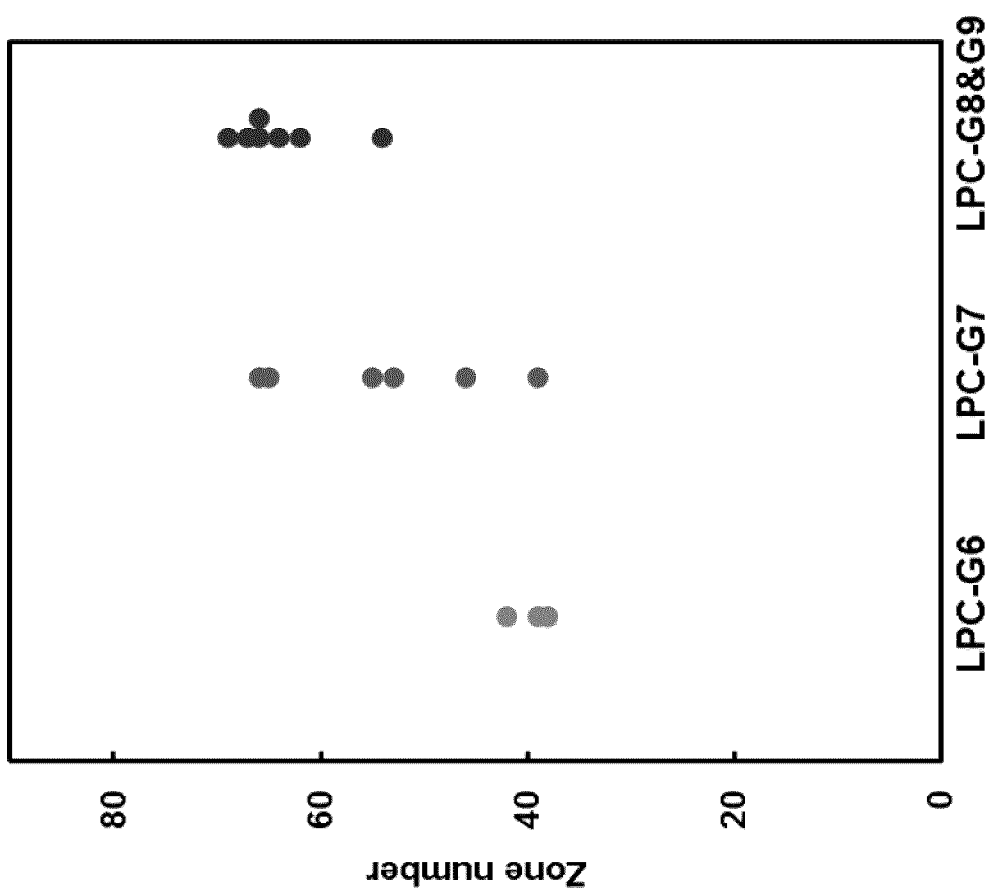
FIG. 15E is a charting showing the medians of capture profiles of samples from prostate cancer patients.
Figure 15F:
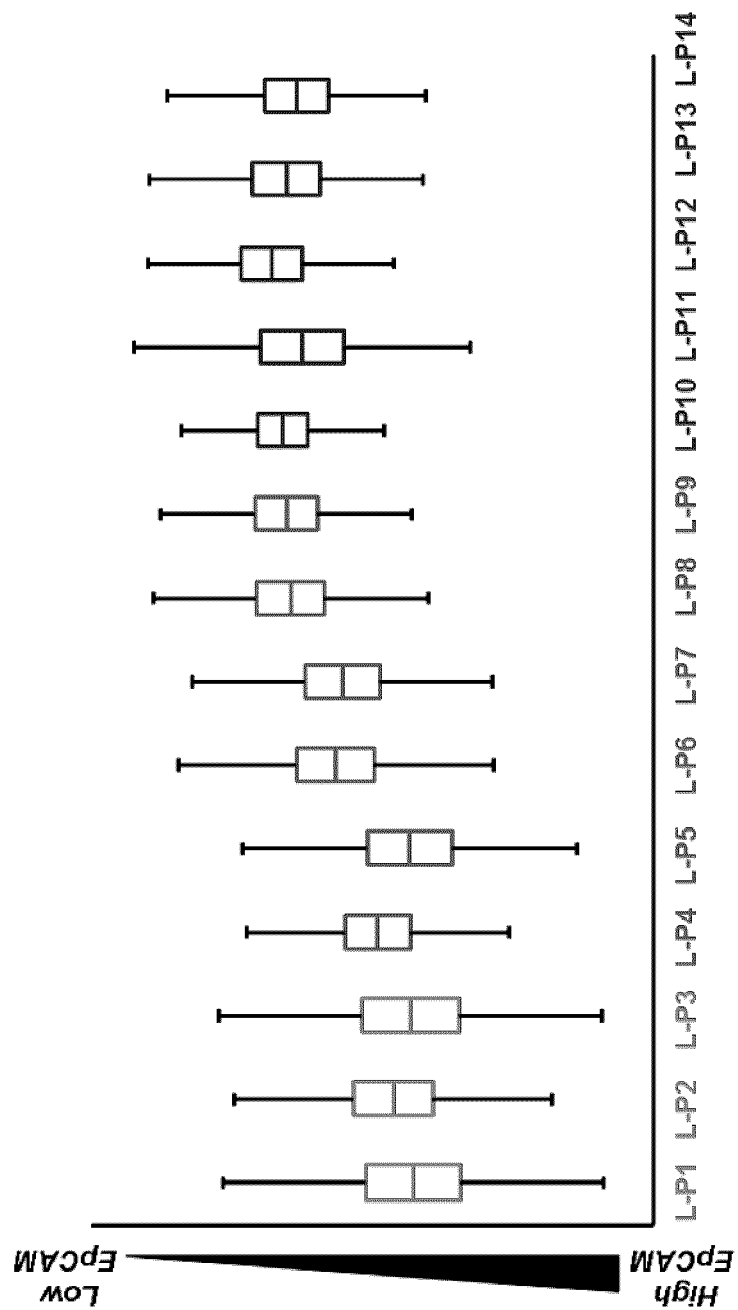
FIGS. 15F and 15G are boxplots showing the CTC profile distribution of samples from patients with localized and metastatic prostate cancer, respectively.
Figure 15G:
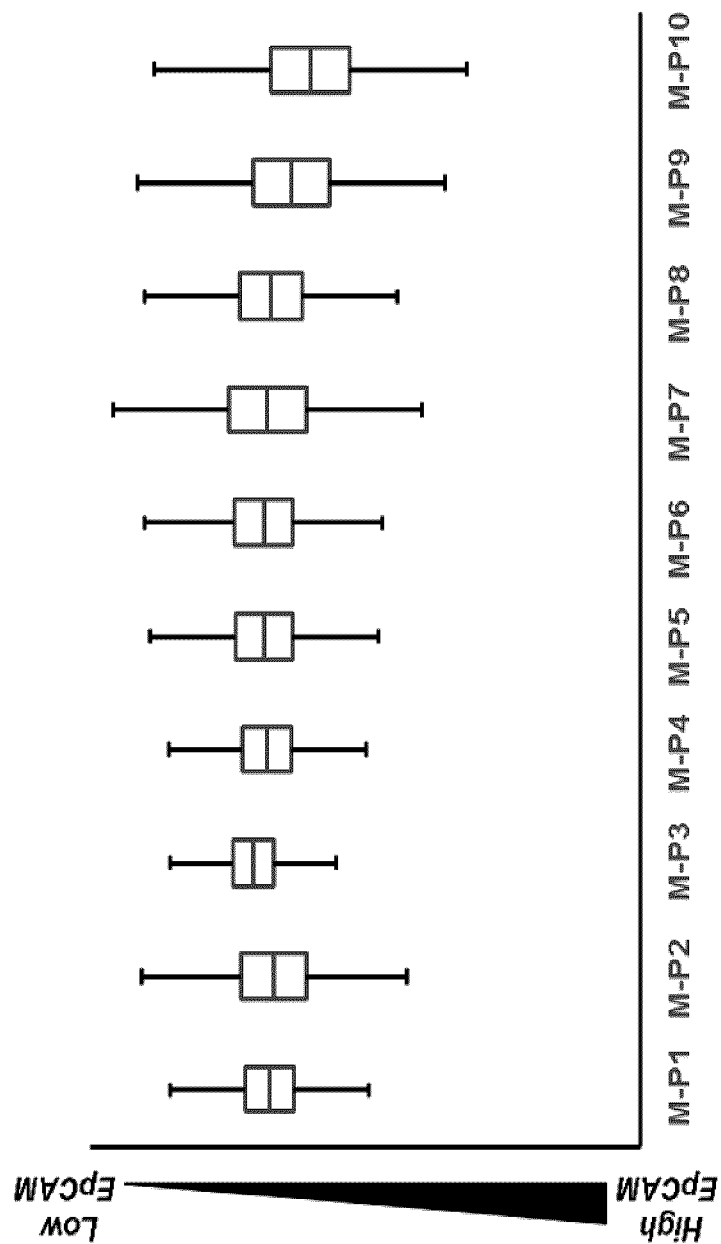

FIG. 15B shows EpCAM profiles for CTCs captured from samples from patients with metastatic, castration-resistant prostate cancer (n=10). FIG. 15C shows EpCAM profiles for CTCs captured from samples from patients with localized prostate cancer (n=14). FIG. 15D is a boxplot that summarizes the CTC profile distribution in patients with localized and metastatic prostate cancer. FIG. 15E shows the medians of MagRC capture profiles of localized prostate cancer patients with tumour with Gleason scores of 6, Gleason

TABLE IV

T-test analysis results for the capture profiles of localized prostate cancer patients with G6-8 and G9 tumours

| Paired t test | Groups Analyzed G6-G8/G9 |
|---|---|
| P value | 0.03 |
| Mean of differences | 22.7 |

TABLE IV-continued

T-test analysis results for the capture profiles of localized
prostate cancer patients with G6-8 and G9 tumours

| Paired t test | Groups Analyzed<br>G6-G8/G9 |
|---|---|
| Are means significant different? (P < 0.05) | Yes |
| One- or two-tailed P value? | Two-tailed |
| t, df | t = 5.8 df = 2 |
| Number of pairs | 3 |

The G7 tumour profile mean values did not exhibit statistical significance from the G6 or G8/G9 patients, indicating significant phenotypic heterogeneity for the G7 patients. This is an interesting finding because G7 patients have variable prognoses; while 50% of patients with G7 tumours do experience cancer recurrence, 50% do not. A much larger study may be performed to determine whether there is a correlation between the CTC phenotypic profiles measured and recurrence, but the analysis of CTC phenotypes for these patients may help elucidate the differences between tumours with similar staging data.

Figure 16A:
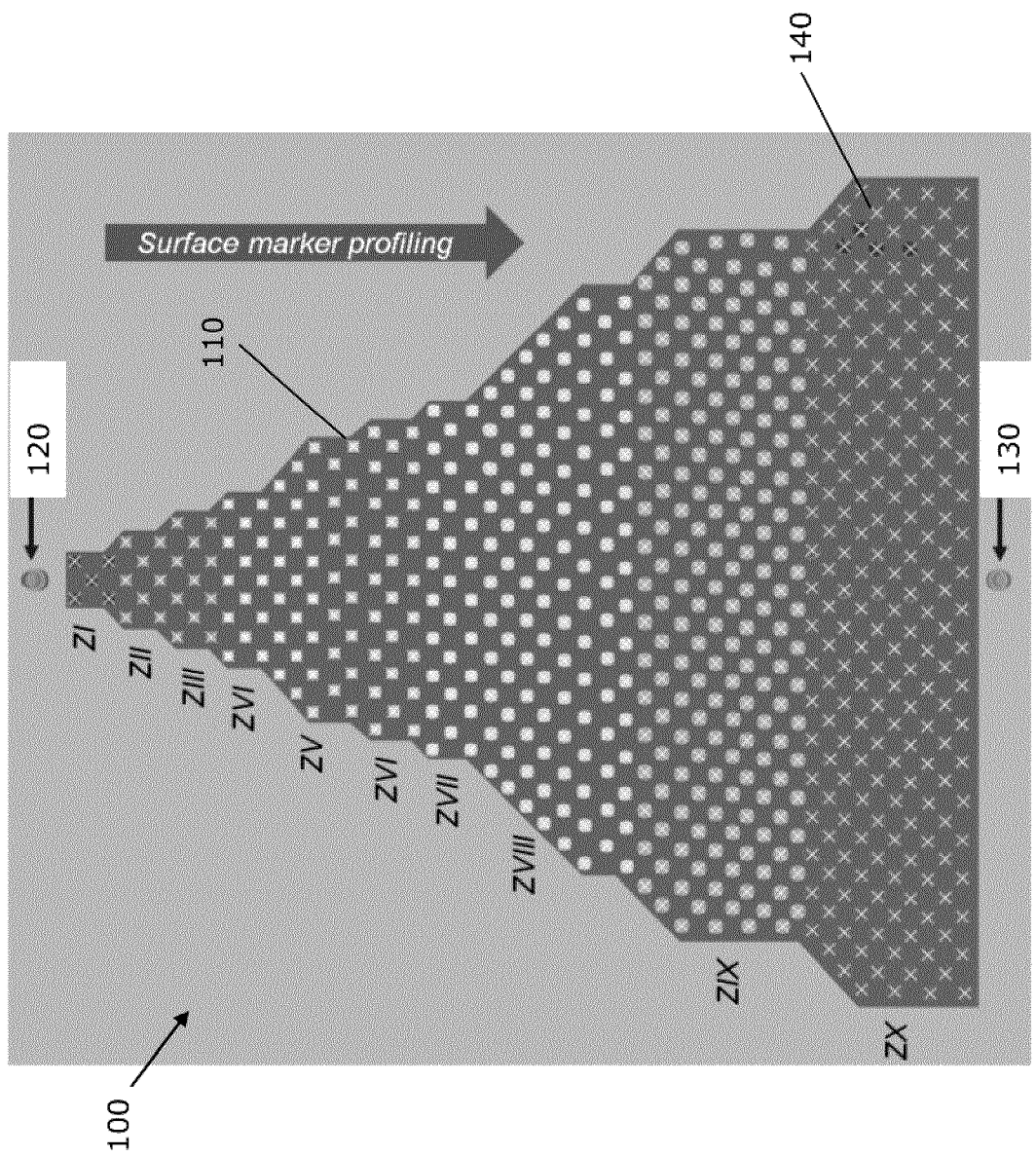
FIG. 16A is a schematic illustrating a example device for magnetic profiling, in which the flow chamber has varying width.

FIG. 16A is a schematic of an example device for magnetic profiling, in which the flow chamber has a varying width. This design may enable greater fabrication yield, for example compared to designs with constant-width flow chambers.

The example device of FIG. 16A enables immunomagnetic separation for profiling cells, based on the principle of operation discussed above. For example, rare cells may be profiled as a function of their surface marker expression. Circular nickel micro-magnets patterned within the flow chamber enhance the externally applied magnetic field. In designs where the flow chamber has constant or substantially equal width throughout, the flow chamber may need to have a relatively long length to enable sufficiently long residence times and the potential for cells to settle towards the bottom of the flow chamber. However, the long length of the device may reduce the rate of device fabrication. In order to increase the rate of device fabrication while ensuring sufficiently long residence times of cells in the flow chamber, the design shown in FIG. 16A has a steady increase in width of the flow chamber, which in turn could reduce the length of device by half.

In the example device 100 of FIG. 16A, the flow chamber 110 has been defined into 10 distinct sections (labeled as ZI to ZX, where section ZI is located closest to the flow inlet 120 and section ZX is located closest to the flow outlet 130), each section differing in width (where width of the flow chamber is measured as in the direction transverse to the direction from flow inlet 120 to flow outlet 130). As illustrated, the width of the flow chamber 110 generally increases from section ZI to section ZX, in the direction of flow. Further, the width within a given section ZI to ZX may or may not be substantially constant; for example, section ZVIII exhibits increasing width in the direction of flow, while section ZI has substantially constant width. As the width of the flow chamber 110 increases, the linear rate of flow decreases.

Each of the sections ZI to ZX includes flow rate-reducing structures 140 (in this case, X-shaped structures) each with a nickel micro-magnet. In this example, the radii of the micro-magnets (and hence the strength of the localized magnetic attractive force associated with each rate-reducing structure) increase from section ZI to section ZX, for example by 10 µm sequentially in each section, from r=145 µm to r=235 µm. On the other hand, increasing the width of the flow chamber 110 in the later sections of the device 100 reduces the drag force acting on cells, allowing the efficient capture of cells with low levels of surface marker expression. In other examples, the size of the micro-magnets may be unchanging, or may vary in a manner not corresponding to the flow chamber sections ZI to ZX (e.g., sections ZI to ZV may all have micro-magnets of one size, while the other sections ZVI to ZX may all have micro-magnets of a second size).

Figure 16B:
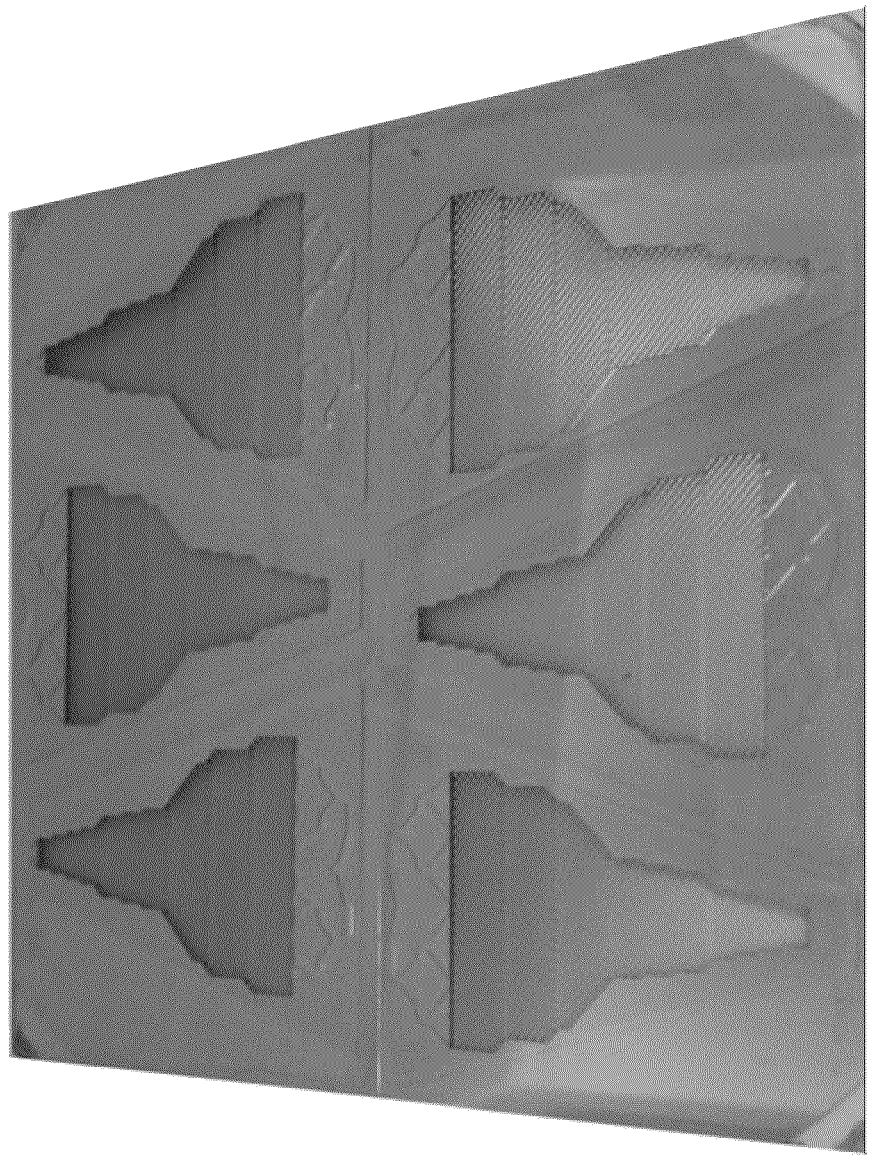
FIG. 16B is an image of a template for fabricating the example device of FIG. 16A.

The variable-width design was found to enable fabrication of six such devices per one 4"×4" nickel slide (see FIG. 16B), compared to fabrication of two equivalent constant width devices in the same amount of time.

Figure 17:
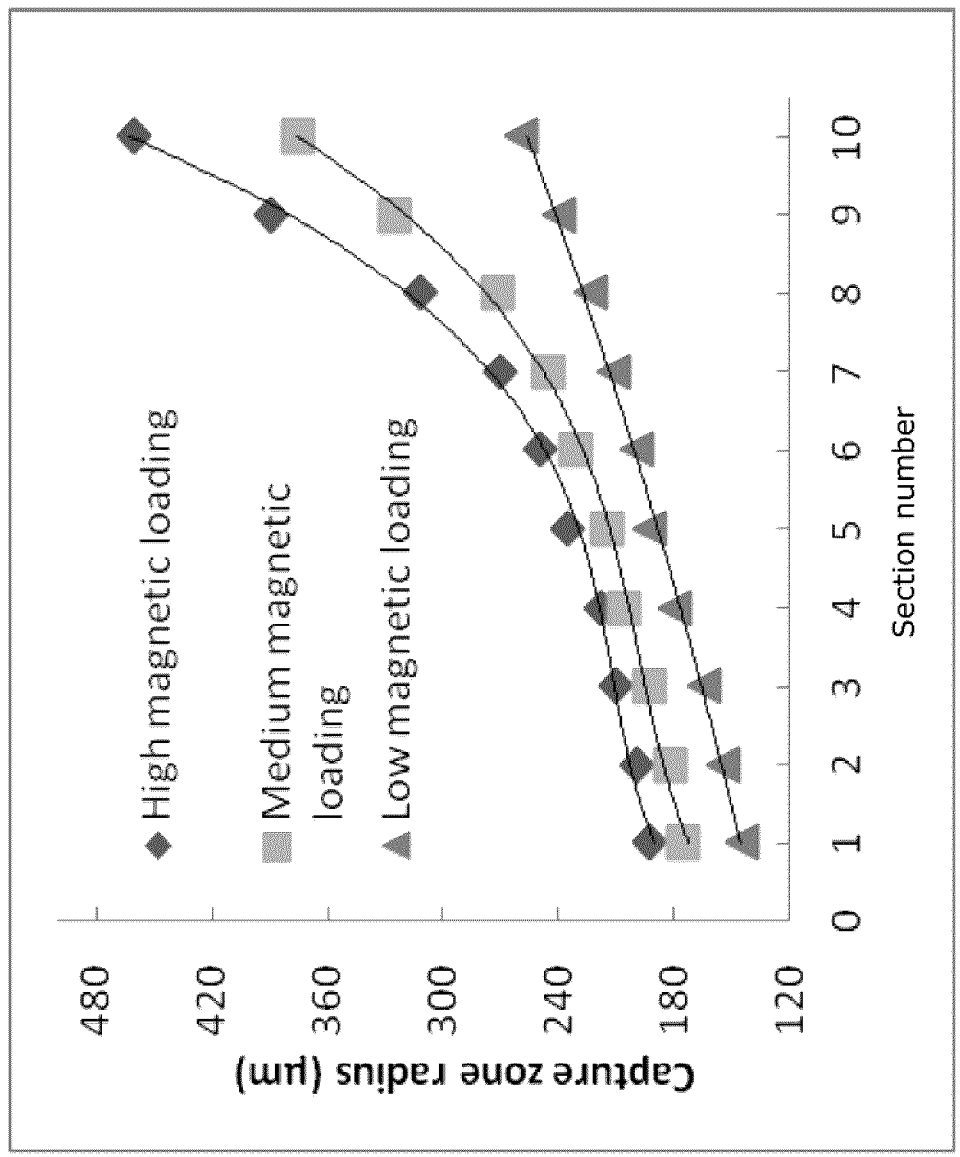
FIG. 17 is a chart illustrating example calculation of the capture zone radius for cells with different levels of magnetic loading in the example device of FIG. 16A.

Increasing the size of the micro-magnets along with the flow chamber width increment increases the area of regions subjected to high magnetic force and low drag force, which subsequently leads to efficient rare cell capture. As discussed above, a capture zone is defined as the region where the magnitudes of the magnetic and drag forces are comparable, meaning that any cells that pass through a capture zone are expected to be captured. For a cell coated with many magnetic nanoparticles, the capture zone generated by small micro-magnet in regions with high linear velocity is sufficiently large to ensure capture in earlier sections of the flow chamber 110. Therefore, cells having high magnetic loadings are captured in earlier sections, near the flow inlet 120, where the small micro-magnets are positioned in sections having smaller width. However, cells coated with a low number of magnetic nanoparticles are deflected only if they are close enough to the bottom of the flow chamber 110 and the edges of the micro-magnets, where the magnetic force acting on the nanoparticles is highest. At the final sections of the flow chamber 110, large micro-magnets and slow flow create large enough capture zones for capturing of cells with low levels of surface marker expression. In order to determine the size of a capture zone for the cells having relative high, medium, low levels of magnetic loading, the radius (measured from the center of the 'X'-structure) of the capture zone was measured at the height of 10 µm along the length of the flow chamber 110. FIG. 17 is a chart plotting calculated capture zone radius for high, medium and low levels of magnetic loading, for each of sections ZI to ZX.

In a first set of experiments to study the performance of this variable-width configuration, the profiling capabilities of the variable-width design was studied using three cancer cell lines. EpCAM was selected as an initial profiling marker, since it is a well-characterized marker present on the surface of many different types of cancer cells. Three different cell lines, VCaP (a human prostate cancer cell line), SKBR3 (a breast adenocarcinoma cell line), and MDA-MB-231 (a breast cancer cell line with mesenchymal characteristics) were incubated with anti-EpCAM antibodies functionalized with magnetic nanoparticles and analyzed using the variable-width device. One hundred cells suspended in 100 µL of buffered solution were introduced into the device at a flow rate of 400 µL/hr, captured, and stained using a nuclear marker. Profiling experiments for each cell line were repeated three times each.

Figure 18A:
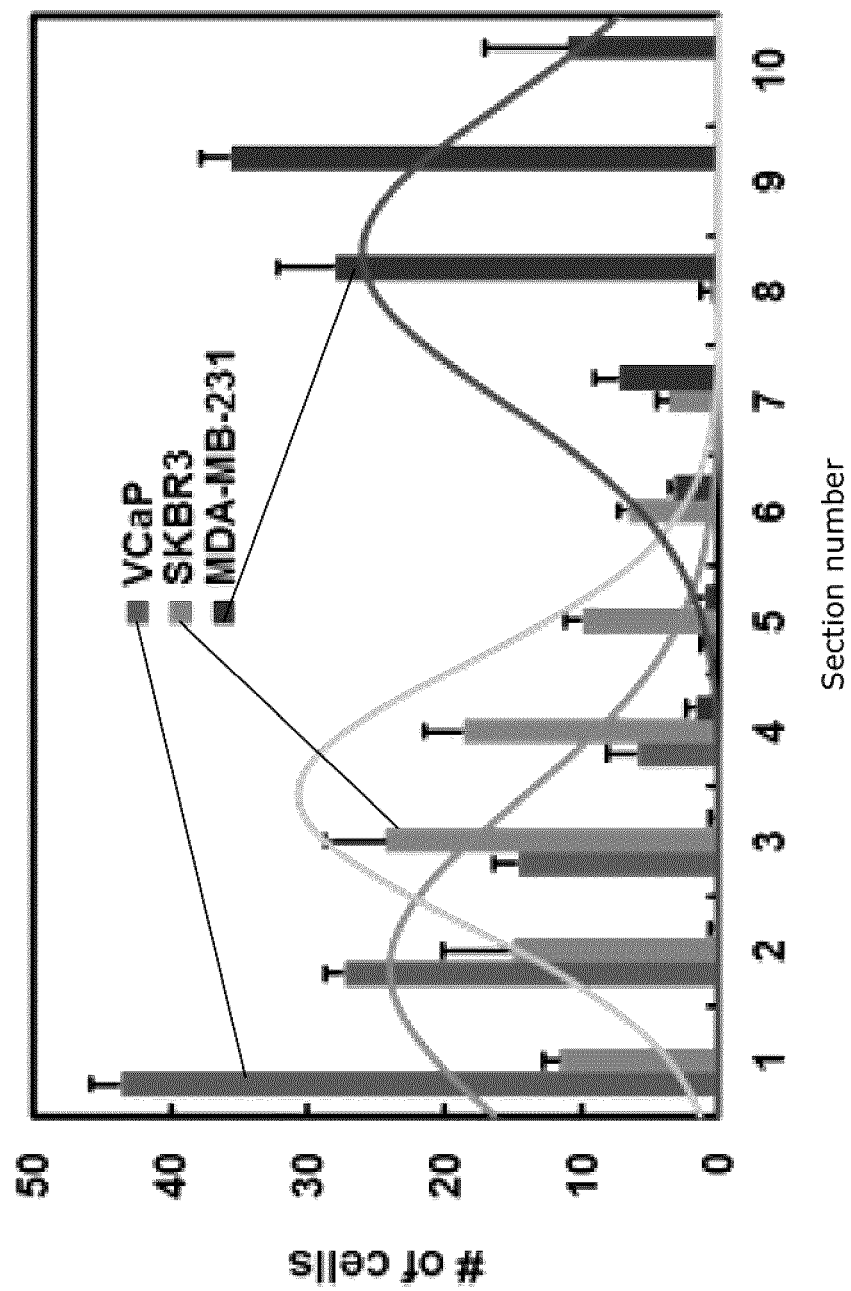
FIG. 18A is a chart illustrating example results using the device of FIG. 16A for magnetic profiling.
Figure 18B:
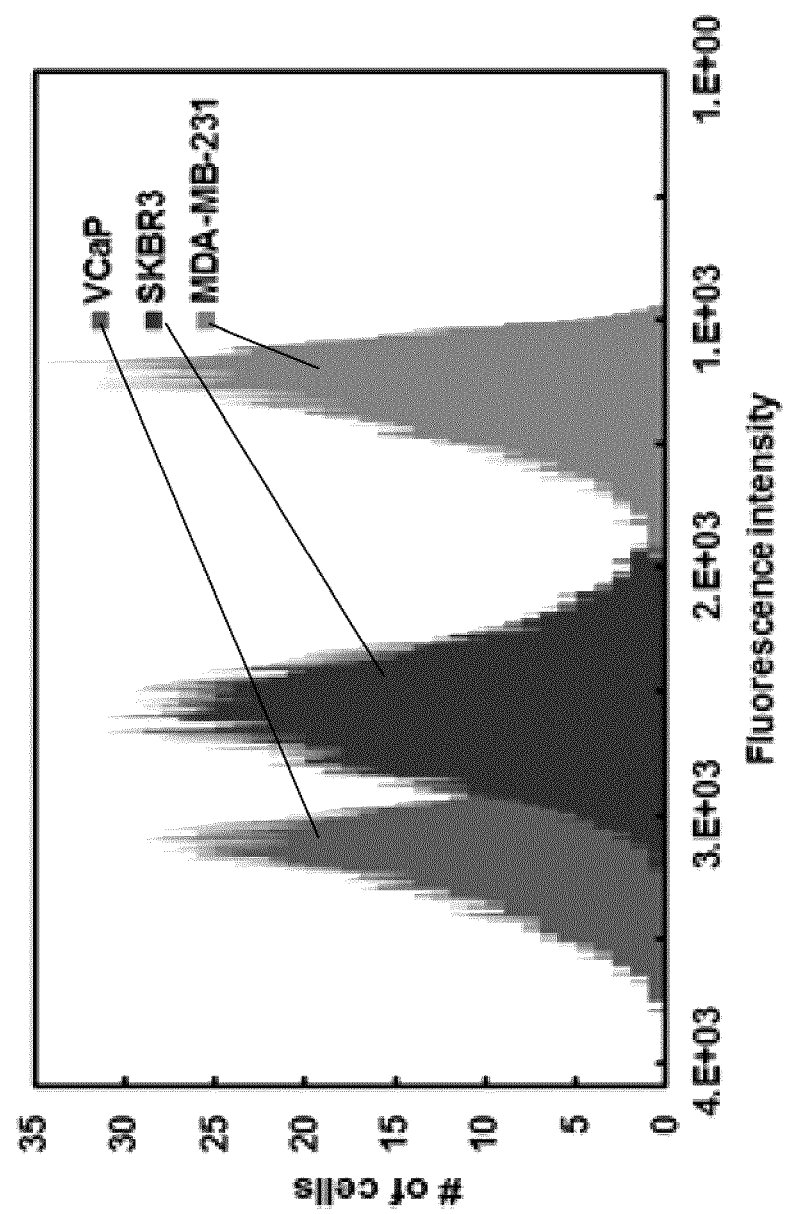
FIG. 18B is a chart demonstrating the EpCAM expression measured by flow cytometry for three different cell lines.

The cells trapped in different sections were then enumerated using fluorescence microscopy. The three different cell lines exhibited markedly different distributions within the device, as illustrated by the results shown in FIG. 18A. High recoveries of the cells injected into the device were achieved (VCaP=93±2%, SKBR3=91±5%, MDA-MB-231=89±2%). VCaP cells, which have the highest level of EpCAM expression, were found primarily in the earlier sections of the flow chamber. However, MDA-MB-231 cells which have the lowest level of EpCAM expression were only captured after they were slow enough and encountered the large micro-magnets in the later sections of the flow chamber near the flow outlet. The relative levels of EpCAM expression of the cell lines were confirmed via flow cytometry, the results of which are shown in FIG. 18B. These results indicate that the variable-width device, as shown in FIG. 16A, is able to sort cells according to the expression level of a targeted surface marker. Moreover, the device was found to efficiently capture cells exhibiting even low levels of a targeted surface marker.

Figure 19A:
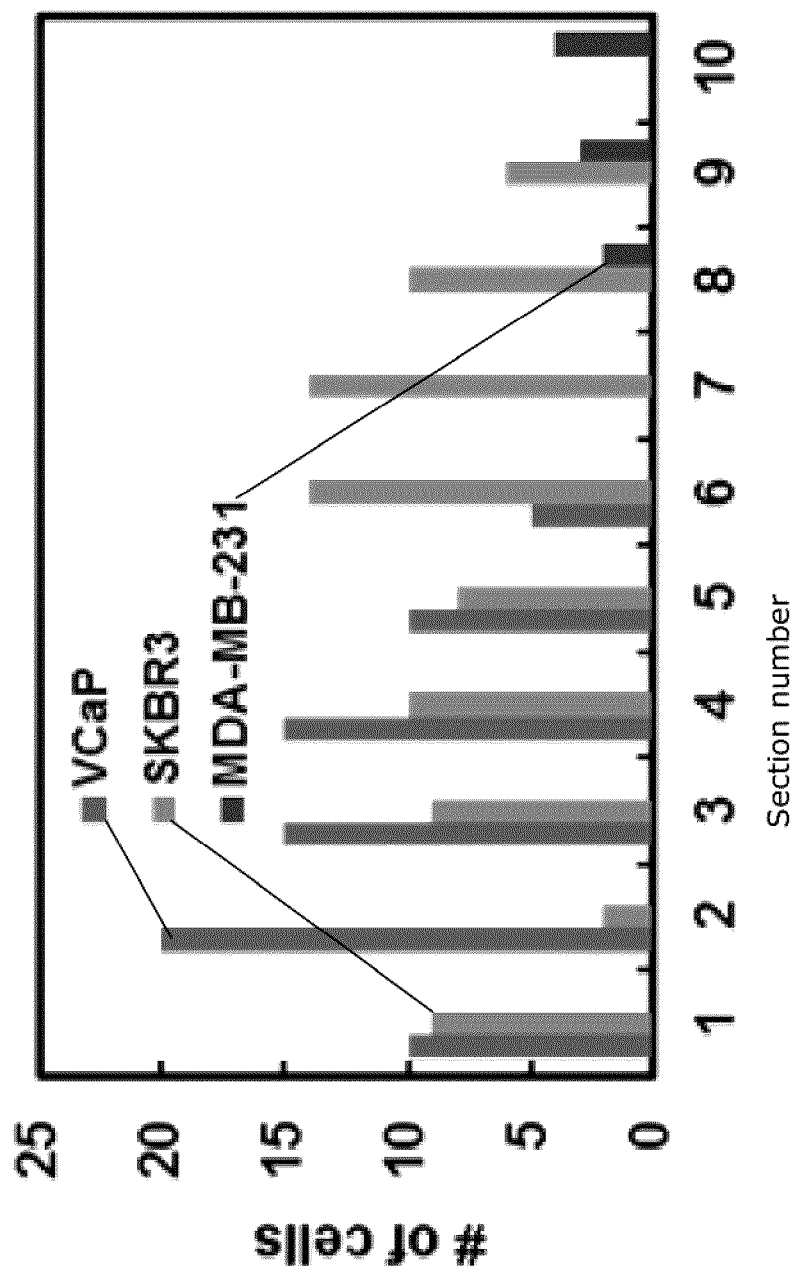
FIGS. 19A and 19B are charts illustrating example results of control experiments.
Figure 19B:
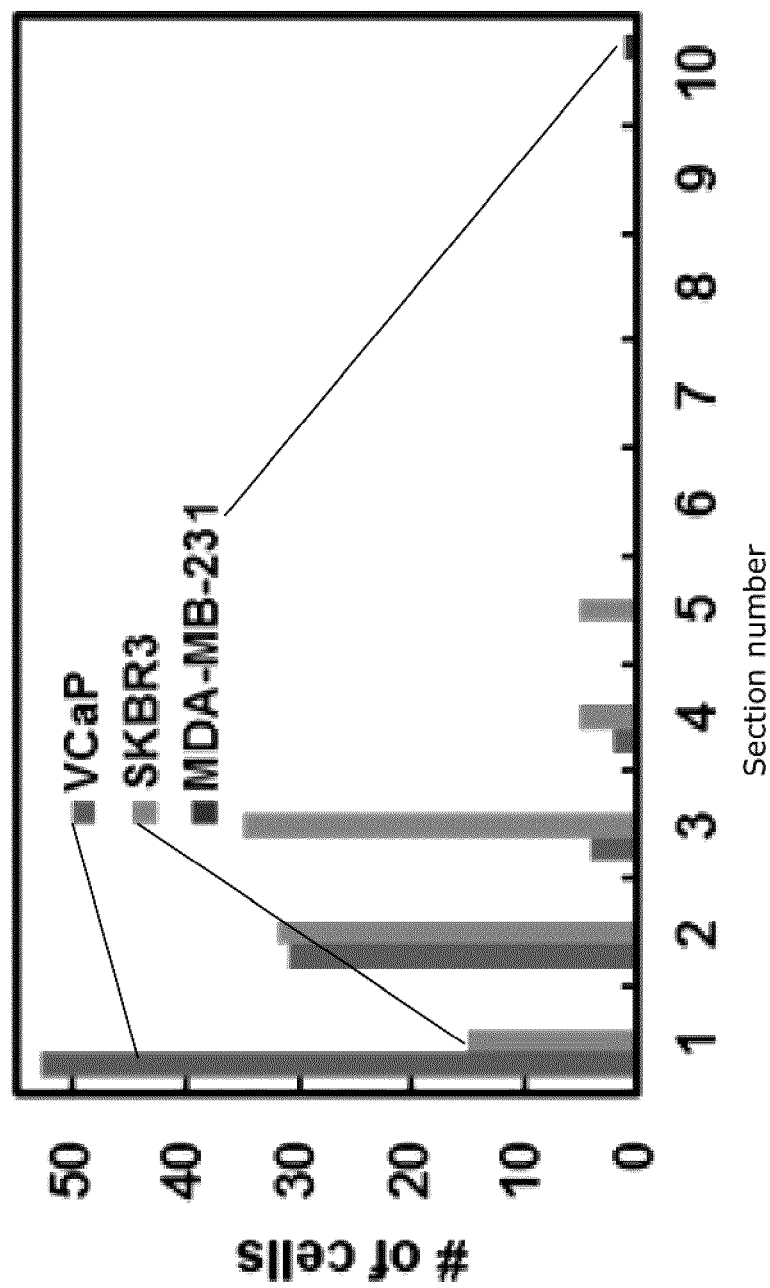

Control experiments were performed to investigate the effect of both flow chamber width increment and use of micro-magnets for capturing cells with varied levels of EpCAM expression. A first control experiment studied the capture capabilities of a variable-width device lacking nickel micro-magnets. One hundred of VCaP, SKBR3, and MDA-MB-231 cells were suspended in 100 µL of buffered solution and introduced into a 10-section variable-width device lacking micro-magnets. Results are shown in FIG. 19A. Capture experiments without the use of micro-magnets illustrate that VCaP cells that have the highest level of magnetic loading were captured at earlier sections of the flow chamber (i.e., closer to the flow inlet) regardless of using micro-magnets. However, SKBR3 (medium magnetic loading) cells were distributed randomly along the device. The capture efficiency of MDA-MB-231 cells that have the lowest level of EpCAM expression was very low (9%) without incorporating micro-magnets.

Control experiment using a device with a flow chamber of fixed width (width=13.6 mm) yielded less useful profiling information (results are shown in FIG. 19A), highlighting the role of the flow chamber width increment for capturing low EpCAM cells. A width of 13.6 mm was found to be large enough for VCaP and SKBR3 cell capture, and the use of nickel micro-magnets resulted in an efficient capture of cells having high and medium magnetic loadings. However, longer residence time is required for settling of MDA-MB-231 cells, indicating the usefulness of flow chamber width increment for efficient recovery of cells with the low levels of magnetic loading.

A quantitative model was developed to explore the capture efficiency of cells exhibiting varied expression levels. The capture probability at a given flow chamber section can be calculated as:

$$P_{capture} = j \times \frac{A_{F_m > F_d}}{\dot{Q}} \times \alpha$$

Where j is the number of rows of capture structures in each zone, $\dot{Q}$ is the flow rate (µL/hr) at each zone, $A_{F_m > F_d}$ is the average percentage of area surrounding a flow rate-reducing structure in which magnetic force and the drag force are comparable, and α is an experimentally determined proportionality constant with unit set to ensure $P_{capture}$ is unit-less (unit of α is hr/µL).

The capture efficiency in the ith section can be calculated as:

$$E_i = P_i[N - (E_1 + E_2 + \ldots + E_{i-1})] \quad i=1,2,\ldots,10$$

In this equation, $E_i$ and $P_i$ are defined as capture efficiency and capture probability, respectively, in the ith section, and N is the total number of loaded cells. Capture efficiency of each section can be calculated by substituting the capture efficiency terms of the prior sections. In the following, capture efficiencies of sections 1, 2, and 3 have been written as an example:

$$E_1 = NP_1$$

$$E_2 = P_2[N - NP_1] = NP_2[1 - P_1]$$

$$E_3 = NP_3[1 - P_1 - P_2 + P_1 P_2]$$

The total capture efficiency is the sum of capture efficiencies in each individual zone:

$$E_T = E_1 + E_2 + E_3 + \ldots + E_{10}$$

By substituting capture efficiency terms of sections, this becomes:

$$E_T = N[P_1 + P_2 \ldots + P_{10} - P_1 P_2 - P_1 P_3 - \ldots + P_1 P_2 P_3 + \ldots]$$

Using the capture zone radius calculation (e.g., as shown in FIG. 17), the average percentage of area surrounding a capture structure in which the magnetic force and the drag force are comparable was calculated for cells having high, medium and low levels of magnetic loading. The spatial distributions of net force acting on a cell was simulated and COMSOL was used to calculate the capture zone radii and $A_{F_m > F_d}$. The table below summarizes this percentage for VCaP, SKBR3, and MDA-MB-231 cells at different zones.

TABLE V

Calculation of the average percentage of area surrounding a capture structure in which the magnetic force exceeds the drag as a function of cell line

| | Section number | | | | | | | | | |
|---|---|---|---|---|---|---|---|---|---|---|
| | 1 | 2 | 3 | 4 | 5 | 6 | 7 | 8 | 9 | 10 |
| $A_{F_m > F_d}$ (VCaP) | 7.81 | 7.84 | 8.81 | 9.03 | 11.38 | 13.44 | 19.1 | 35.5 | 73.9 | 93.1 |
| $A_{F_m > F_d}$ (SKBR3) | 4.52 | 4.47 | 4.89 | 6.14 | 6.39 | 8.57 | 10 | 17.6 | 39 | 62.9 |
| $A_{F_m > F_d}$ (MDA-MB-231) | 0 | 0 | 0 | 0.89 | 1.47 | 1.12 | 1.57 | 2.05 | 3.74 | 7.81 |

The initial flow rate in the device is set to 400 µL/hr. The flow rates $\dot{Q}$ in the successive sections have been calculated according to the width of each section, presented in the table below.

TABLE VI

Calculation of the flow rates in different sections of the flow chamber

| | Section number | | | | | | | | | |
|---|---|---|---|---|---|---|---|---|---|---|
| | 1 | 2 | 3 | 4 | 5 | 6 | 7 | 8 | 9 | 10 |
| Flow rate (µL/hr) | 400 | 311 | 255 | 219 | 151 | 136 | 125 | 88 | 57 | 51 |

The data was fit to the VCaP capture efficiency data, and the model was found to best fit the data using a proportionality constant α of 0.48. For SKBR3 and MDA-MB-231, the model was found to best fit the data using a proportionality constant α of 0.56 and 0.95, respectively.

TABLE VII

Model parameters used to validate capture efficiency as a function of cell line

| Cell line | Model parameter (α) | Predicted capture Efficiency ($E_{model}$) | Experimentally measured capture efficiency ($E_{experimental}$) |
|---|---|---|---|
| VCaP | 0.48 | 75% | 93% |
| SKBR3 | 0.56 | 74% | 91% |
| MDA-MB-231 | 0.95 | 86% | 89% |

This variable-width design was found to increase the fabrication rate threefold (compared to an equivalent constant-width design), which may make it more suitable for different research projects and clinical studies.

The above example described a variable-width design where the width of the flow chamber was varied over 10 sections. In other examples, the width of the flow chamber may be varied over a different number of sections. For example, there may be 100 different sections, with the width of the flow chamber increasing successively through the sections. In various experiments, a design with 10 sections of different width (e.g., as described above) was found to be sufficient to provide a satisfactory resolution for profiling.

In some examples, the disclosed methods and devices may be used for sorting or distinguishing between two or more types of target particles (e.g., two or more different types of cells, such as distinguishing between VCaP, SKBR3, and MDA-MB-231 cells (see FIG. 2B, for example), between HER2, EpCAM, and N-Cadherin cells (see FIG. 2C, for example), or between cells treated to induce EMT and untreated cells (see FIG. 2D, for example). In general, the disclosed methods and devices may be used for distinguishing between two or more types of target particles where each type of target particle has a different magnetic susceptibility (e.g., different magnetic loading). For example, the device may define two or more regions in the flow chamber, where each region has flow rate-reducing structures of a different size and having a different magnetic field profile. The regions of the flow chamber may be arranged in series or in parallel, for example. A first type of particles may be captured in a first region due to the magnetic attractive force in the first region exceeding the drag force on the particles, while a second type of particles may not be captured and may instead flow through the first region. The second type of particles may instead be captured in a second region (e.g., which may have a larger capture zone).

In various examples, the present disclosure describes methods of magnetic ranking cytometry and devices for implementing magnetic ranking cytometry. Use of the disclosed methods and devices may provide accurate profiles of low levels of CTCs in unprocessed blood samples. In example studies, the disclosed methods and devices were found to provide similar information obtained with a gold standard method, flow cytometry, but also compatible with much lower cell numbers and not affected by normal blood cells.

The high level of sensitivity obtained and compatibility with whole blood may make the disclosed methods and devices useful for the analysis of rare circulating tumor cells. In example studies, CTCs collected from mice with xenografted tumors were monitored as a function of tumor growth, and an emerging phenotypic profile was acquired for these cells.

It may be noted that examples of the disclosed methods may be implemented using standard syringe pumps and fluorescence imaging interfaced with an example of the disclosed devices that may be relatively straightforward to fabricate; no custom instrumentation may be required.

Using the disclosed methods and devices, CTC profiles may be more concretely connected with the progression of cancer and the formation of metastatic lesions.

Although the present disclosure describes the disclosed methods and devices for CTC profiling, allowing the heterogeneity and evolving phenotypes of CTCs to be monitored, the disclosed methods and devices may be used for magnetic profiling of other particles, including other cells, for other purposes.

The embodiments of the present disclosure described above are intended to be examples only. The present disclosure may be embodied in other specific forms. Alterations, modifications and variations to the disclosure may be made without departing from the intended scope of the present disclosure. While the systems, devices and processes disclosed and shown herein may comprise a specific number of elements/components, the systems, devices and assemblies could be modified to include additional or fewer of such elements/components. For example, while any of the elements/components disclosed may be referenced as being singular, the embodiments disclosed herein could be modified to include a plurality of such elements/components. Selected features from one or more of the above-described embodiments may be combined to create alternative embodiments not explicitly described. All values and subranges within disclosed ranges are also disclosed. The subject matter described herein intends to cover and embrace all suitable changes in technology. All references mentioned are hereby incorporated by reference in their entirety.

REFERENCES

1. C. L. Chaffer, R. A. Weinberg, A perspective on cancer cell metastasis. *Science* 331, 1559-1564 (2011).
2. V. Plaks, C. D. Koopman, Z. Werb, Cancer. Circulating tumor cells. *Science* 341, 1186-1188 (2013).
3. C. Alix-Panabieres, K. Pantel, Challenges in circulating tumour cell research. *Nat. Rev. Cancer* 14, 623-631 (2014).
4. J. M. Lang, B. P. Casavant, D. J. Beebe, Circulating tumor cells: getting more from less. *Sci. Transl. Med.* 4, 141ps113 (2012).

5. M. Yu et al., Circulating breast tumor cells exhibit dynamic changes in epithelial and mesenchymal composition. *Science* 339, 580-584 (2013).
6. I. Y. Wong et al., Collective and individual migration following the epithelial-mesenchymal transition. *Nat. Mater.* 13, 1063-1071 (2014).
7. X. Hu et al., Marker-specific sorting of rare cells using dielectrophoresis. *Proc. Natl. Acad. Sci., U.S.A.* 102, 15757-15761 (2005).
8. S. Nagrath et al., Isolation of rare circulating tumour cells in cancer patients by microchip technology. *Nature* 450, 1235-1239 (2007).
9. A. A. Adams et al., Highly efficient circulating tumor cell isolation from whole blood and label-free enumeration using polymer-based microfluidics with an integrated conductivity sensor. *J. Am. Chem. Soc.* 130, 8633-8641 (2008).
10. A. H. Talasaz et al., Isolating highly enriched populations of circulating epithelial cells and other rare cells from blood using a magnetic sweeper device. *Proc. Natl. Acad. Sci., U.S.A.* 106, 3970-3975 (2009).
11. S. L. Stott et al., Isolation of circulating tumor cells using a microvortex-generating herringbone-chip. *Proc. Natl. Acad. Sci., U.S.A.* 107, 18392-18397 (2010).
12. S. Wang et al., Highly efficient capture of circulating tumor cells by using nanostructured silicon substrates with integrated chaotic micromixers. *Angew. Chem. Intl. Ed.* 50, 3084-3088 (2011).
13. P. G. Schiro et al., Sensitive and high-throughput isolation of rare cells from peripheral blood with ensemble-decision aliquot ranking. *Angew. Chem. Intl. Ed.* 51, 4618-4622 (2012).
14. W. Zhao et al., Bioinspired multivalent DNA network for capture and release of cells. *Proc. Natl. Acad. Sci., U.S.A.* 109, 19626-19631 (2012).
15. E. Ozkumur et al., Inertial focusing for tumor antigen-dependent and -independent sorting of rare circulating tumor cells. *Sci. Transl. Med.* 5, 179ra147 (2013).
16. H. J. Yoon et al., Sensitive capture of circulating tumour cells by functionalized graphene oxide nanosheets. *Nat. Nanotechnol.* 8, 735-741 (2013).
17. E. Sollier et al., Size-selective collection of circulating tumor cells using Vortex technology. *Lab Chip* 14, 63-77 (2014).
18. E. Reategui et al., Tunable nanostructured coating for the capture and selective release of viable circulating tumor cells. *Adv. Mater.* 27, 1593-1599 (2015).
19. B. P. Casavant et al., A negative selection methodology using a microfluidic platform for the isolation and enumeration of circulating tumor cells. *Methods* 64, 137-143 (2013).
20. D. Issadore et al., Ultrasensitive clinical enumeration of rare cells ex vivo using a micro-hall detector. *Sci. Transl. Med.* 4, 141ra192 (2012).
21. T. L. Halo et al., NanoFlares for the detection, isolation, and culture of live tumor cells from human blood. *Proc. Natl. Acad. Sci., U.S.A.* 111, 17104-17109 (2014).
22. S. C. Bendall et al., Single-cell mass cytometry of differential immune and drug responses across a human hematopoietic continuum. *Science* 332, 687-696 (2011).
23. J. D. Besant et al., Velocity valleys enable efficient capture and spatial sorting of nanoparticle-bound cancer cells. *Nanoscale* 7, 6278-6285 (2015).
24. R. M. Mohamadi et al., Nanoparticle-mediated binning and profiling of heterogeneous circulating tumor cell subpopulations. *Angew. Chem. Intl. Ed. Engl.* 54, 139-143 (2015).
25. P. Chen et al., Microscale Magnetic Field Modulation for Enhanced Capture and Distribution of Rare Circulating Tumor Cells. *Sci. Rep.* 5, 8745-8753 (2015).
26. Y. B. Zhang et al., The effects of $CoCl_2$ on HIF-1α protein under experimental conditions of autoprogressive hypoxia using mouse models. *Int. J. Mol. Sci.* 15, 10999-1012 (2014).
27. D. L. Jaye et al., Translational applications of flow cytometry in clinical practice. *J. Immunol.* 188, 4715-4719 (2012).
28. Z. Wang, J. M. Belovich, A simple apparatus for measuring cell settling velocity. *Biotechnol. Prog.* 26, 1361-1366 (2010).

The invention claimed is:

1. A device for magnetic profiling of target particles in a flow, the device comprising:
   a flow chamber; and
   a plurality of flow rate-reducing structures in the flow chamber, each structure comprising a trapping surface shaped to reduce flow rate in a vicinity of the trapping surface;
   each flow rate-reducing structure being provided with a respective micro-magnet to produce a localized magnetic attractive force, the localized magnetic attractive force associated with each flow rate-reducing structure defining a respective capture zone in the vicinity of each of the flow rate-reducing structure;
   wherein the magnetic attractive force, in the capture zone, is sufficiently high to overcome drag force on a given subset of the target particles to promote capture of any particles belonging to the subset of the target particles in the capture zone;
   at least a first and a second flow rate-reducing structure being provided with respective first and second micro-magnets having different characteristics to produce different localized magnetic attractive forces, thereby defining respective first and second capture zones of different sizes in the respective vicinities of the first and second flow rate-reducing structures; and
   wherein different target particles having different magnetic susceptibility are captured in different capture zones.

2. The device of claim 1 wherein each respective the micro-magnet is a nickel micro-magnet, and the first and second micro-magnets provided for the respective first and second flow rate-reducing structures have differences in size to thereby give rise to the different sizes of the respective first and second capture zones.

3. The device of claim 1, further comprising an external arrangement of magnets to apply an external magnetic field gradient over the flow chamber.

4. The device of claim 1, wherein the trapping surface of at least one flow rate-reducing structure includes at least one concave surface, the concave surface being concave towards a direction of flow.

5. The device of claim 1, wherein the trapping surface of at least one flow rate-reducing structure is defined by two joined arms defining an angle.

6. The device of claim 1, wherein the flow rate-reducing structures comprise at least one X-shaped structure or cross-shaped structure, wherein the trapping surface is defined by two arms of the X-shaped or cross-shaped structure.

7. The device of claim 1, wherein the localized magnetic attractive force associated with each flow rate-reducing structure progressively increases in a flow direction.

8. The device of claim 1, wherein the flow chamber progressively increases in width in a flow direction.

9. The device of claim 8, wherein the flow chamber is defined into ten sections, each section increasing in width compared to an upstream section.

10. The device of claim 1, wherein the device is configured for magnetic profiling of magnetically labeled circulating tumor cells (CTCs) in a sample.

11. The device of claim 10 wherein the sample is a whole blood sample.

12. A method for magnetic profiling of target particles in a flow, the method comprising:
   introducing the sample containing the target particles to the device of claim 1, the target particles being susceptible to a magnetic attraction force;
   washing the device of any uncaptured particles; and
   obtaining an image of captured particles within the device.

13. The method of claim 12, wherein the target particles are labeled with magnetically susceptible nanobeads.

14. The method of claim 13, wherein the target particles are magnetically labeled cancer cells in a blood sample.

15. The device of claim 12 wherein obtaining an image of captured particles comprises immunostaining the washed device.

\* \* \* \* \*